US009023767B2

(12) United States Patent
Shelton et al.

(10) Patent No.: US 9,023,767 B2
(45) Date of Patent: May 5, 2015

(54) γ-SECRETASE SUBSTRATES AND METHODS OF USE

(75) Inventors: Christopher Chad Shelton, Alexandria, VA (US); Yuan Tian, New York, NY (US); Yueming Li, New York, NY (US)

(73) Assignee: Memorial Sloan-Kettering Cancer Center, New York, NY (US)

( * ) Notice: Subject to any disclaimer, the term of this patent is extended or adjusted under 35 U.S.C. 154(b) by 782 days.

(21) Appl. No.: 12/776,141

(22) Filed: May 7, 2010

(65) Prior Publication Data

US 2010/0285988 A1  Nov. 11, 2010
US 2011/0143954 A2  Jun. 16, 2011
US 2011/0257027 A2  Oct. 20, 2011

Related U.S. Application Data

(60) Provisional application No. 61/176,333, filed on May 7, 2009.

(51) Int. Cl.
C40B 30/04 (2006.01)
C07K 14/47 (2006.01)
G01N 33/542 (2006.01)
G01N 33/573 (2006.01)

(52) U.S. Cl.
CPC .......... *C07K 14/4711* (2013.01); *G01N 33/542* (2013.01); *G01N 33/573* (2013.01); *G01N 2500/02* (2013.01); *G01N 2800/2814* (2013.01)

(58) Field of Classification Search
None
See application file for complete search history.

(56) References Cited

U.S. PATENT DOCUMENTS

| 4,816,567 | A | 3/1989 | Cabilly et al. |
| 4,873,316 | A | 10/1989 | Meade et al. |
| 4,946,778 | A | 8/1990 | Ladner et al. |
| 5,723,584 | A | 3/1998 | Schatz |
| 5,874,239 | A | 2/1999 | Schatz |

(Continued)

FOREIGN PATENT DOCUMENTS

EP  0264166 A1  4/1988
WO  01/83811 A1  11/2001

(Continued)

OTHER PUBLICATIONS

Adams et al., "The c-myc oncogene driven by immunoglobulin enhancers induces lymphoid malignancy in transgenic mice," Dec. 12, 1985, *Nature*, 318:533-538.

(Continued)

*Primary Examiner* — Christian Boesen
(74) *Attorney, Agent, or Firm* — Mueting, Raasch & Gebhardt, P.A.

(57) ABSTRACT

Polypeptide substrates based on modifications or fragments of the various APP isoforms, assay methods based on the use of these substrates, and screening methods directed toward identifying inhibitors of γ-secretase activity. The assay methods and the screening methods are adapted for use in high throughput multi-well plate assay apparatuses. In many embodiments the substrate polypeptides are labeled for ease of detection, and/or may bind specific ligands that themselves are labeled. Generally the labels promote high specificity as well as high sensitivity of detection. These features render the assay and screening methods that employ the labeled substrates especially suited for use in high throughput assay formats. This disclosure further identifies small polypeptides based on a subsequence motif of Aβ that are shown herein to be potent inhibitors of the activity of γ-secretase.

19 Claims, 19 Drawing Sheets

(56) References Cited

U.S. PATENT DOCUMENTS

Figure 1:
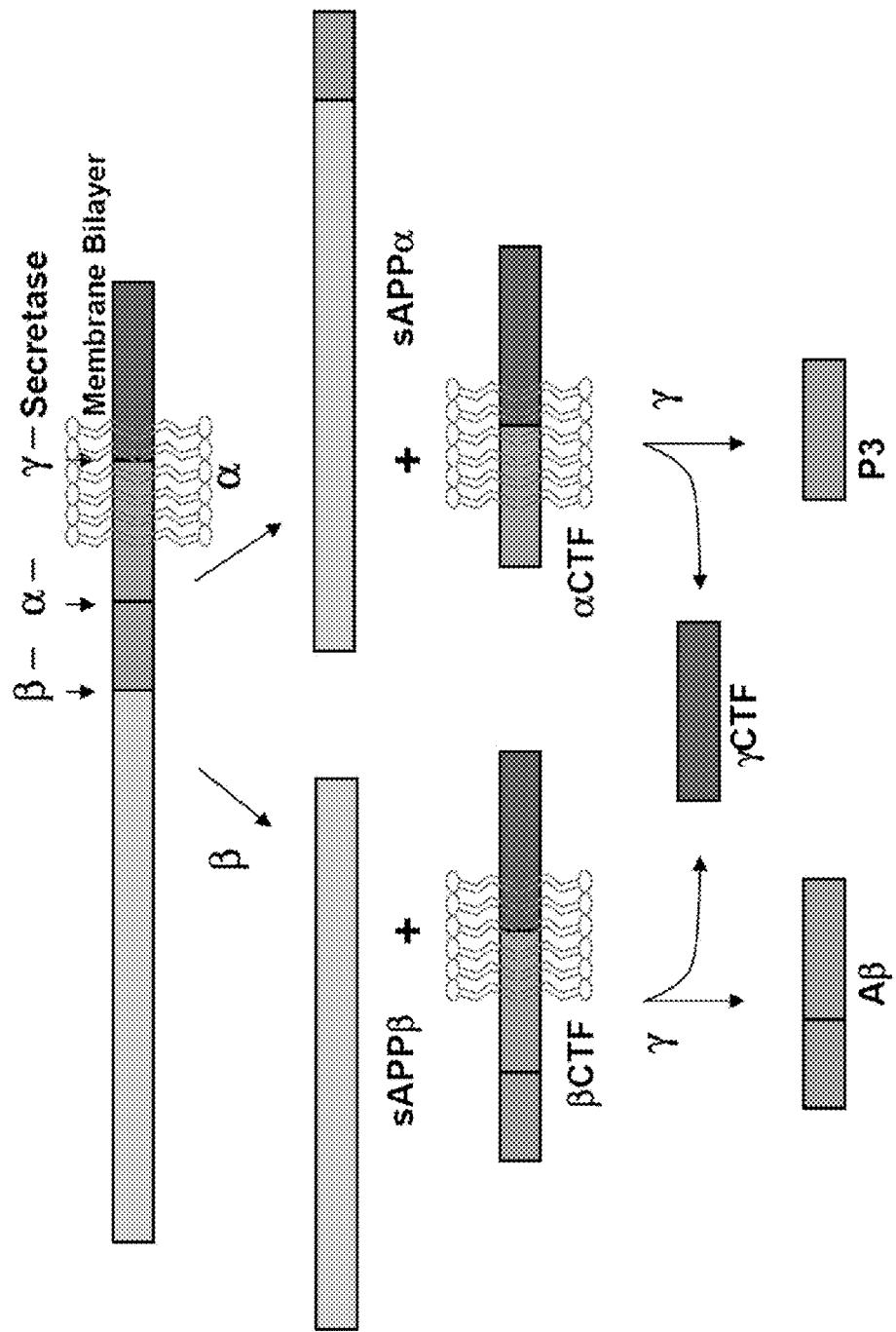

| | | | |
|---|---|---|---|
| 5,932,433 | A | 8/1999 | Schatz |
| 6,625,546 | B2 | 9/2003 | Sepetov et al. |
| 6,800,444 | B1 | 10/2004 | Cook et al. |
| 6,936,477 | B2 | 8/2005 | Still et al. |
| 7,083,812 | B2 | 8/2006 | Choi et al. |
| 7,378,511 | B2 | 5/2008 | Gurney et al. |
| 7,498,324 | B2 | 3/2009 | Han et al. |
| 2002/0098173 | A1* | 7/2002 | Findeis et al. ............... 424/94.3 |
| 2002/0115717 | A1* | 8/2002 | Gervais et al. ................ 514/553 |
| 2004/0121411 | A1* | 6/2004 | Roberts et al. ................. 435/7.2 |
| 2004/0132114 | A1* | 7/2004 | Beher ............................ 435/7.2 |
| 2005/0169925 | A1* | 8/2005 | Bardroff et al. ............ 424/146.1 |
| 2006/0036077 | A1 | 2/2006 | Li et al. |
| 2006/0275856 | A1 | 12/2006 | Okochi et al. |
| 2007/0260058 | A1 | 11/2007 | Cheng et al. |
| 2007/0287666 | A1 | 12/2007 | Fraser et al. |
| 2008/0021056 | A1 | 1/2008 | Konradi et al. |
| 2008/0076752 | A1 | 3/2008 | Becker et al. |
| 2008/0085894 | A1 | 4/2008 | Parker et al. |
| 2008/0317764 | A1 | 12/2008 | Huber et al. |
| 2008/0317834 | A1* | 12/2008 | Green et al. .................. 424/450 |
| 2009/0005256 | A1 | 1/2009 | Bittker et al. |
| 2009/0163594 | A1 | 6/2009 | Shapiro et al. |
| 2009/0209041 | A1* | 8/2009 | Gazit .............................. 436/86 |
| 2011/0098227 | A1 | 4/2011 | Sharma et al. |
| 2011/0257027 | A2 | 10/2011 | Shelton et al. |

FOREIGN PATENT DOCUMENTS

| | | |
|---|---|---|
| WO | 03/008635 A2 | 1/2003 |
| WO | WO 2006/102542 A2 | 9/2006 |
| WO | WO 2006/102542 A3 | 4/2009 |

OTHER PUBLICATIONS

Alexander et al., "Expression of the c-myc oncogene under control of an immunoglobulin enhancer in E mu-myc transgenic mice," Apr. 1987 *Mol. Cell. Biol.* 7:1436-1444.

Antczak et al., "Development and validation of a high-density fluorescence polarization-based assay for the trypanosoma RNA triphosphatase TbCet1," Mar. 2009 *Comb. Chem. High Throughput Scrn.* 12:258-268.

Antczak et al., "High-throughput identification of inhibitors of human mitochondrial peptide deformylase," Jun. 2007 *J. Biomol. Scrn.* 12(4):521-535. Available online on Apr. 13, 2007.

Ausubel et al. (eds.), Current Protocols in Molecular Biology. John Wiley & Sons: city, state; copyright 1992. Cover page, publisher's page, and table of contents; 14 pages.

Beher et al., "Pharmacological knock-down of the presenilin 1 heterodimer by a novel gamma-secretase inhibitor: implications for presenilin biology," Nov. 30, 2001 *J. Biol. Chem.* 276(48):45394-45402. Available online on Sep. 26, 2001.

Benda et al., "Differentiated rat glial cell strain in tissue culture," Jul. 26, 1968 *Science* 161:370-371.

Benoist et al., "In vivo sequence requirements of the SV40 early promotor region," Mar. 26, 1981 *Nature* 290:304-310.

Bitter et al., "[33] Expression and secretion vectors for yeast," in *Methods in Enzymology vol. 153 Recombinant DNA Part D.* Academic Press, Inc.: Burlington, MA; Copyright 1987. Title page and pp. 516-544.

Blackburn et al., "Electrochemiluminescence Detection for Development of Immunoassays and DNA Probe Assays for Clinical Diagnostics," 1991 *Clin. Chem.* 37(9):1534-1539.

Bolin et al., "Survey of cell lines in the American Type Culture Collection for bovine viral diarrhea virus," Jul. 1994 *J. Virol. Meth.* 48:211-221.

Brinster et al., "Regulation of metallothionein—thymidine kinase fusion plasmids injected into mouse eggs," Mar. 4, 1982 *Nature* 296:39-42.

Brown et al., "Regulated intramembrane proteolysis: a control mechanism conserved from bacteria to humans," Feb. 18, 2000 *Cell* 100:391-398.

Buonassisi et al., "Hormone-producing cultures of adrenal and pituitary tumor origin," Jul. 15, 1962 *Proc. Natl. Acad. Sci. USA* 48:1184-1190.

Buxbaum et al., "Evidence that tumor necrosis factor alpha converting enzyme is involved in regulated alpha-secretase cleavage of the Alzheimer amyloid protein precursor," Oct. 23, 1998 *J. Biol. Chem.* 273(43):27765-27767.

Chen et al., "TMP21 is a presenilin complex component that modulates gamma-secretase but not epsilon-secretase activity," Apr. 27, 2006 *Nature* 440:1208-1212.

Colbère-Garapin et al., "A new dominant hybrid selective marker for higher eukaryotic cells," Jul. 25, 1981 *J. Mol. Biol.* 150:1-14.

Cooper et al., "Designed chemical libraries for hit/lead optimization," Jun. 2000 *Innovations in Pharmaceutical Technology*; pp. 46, 48, 50, and 52-53. Available online only at: www.iptonline.com/articles/public/IPTFIVE46NP.pdf; 5 pgs.

DeBoer et al., "A flow- and time-dependent index of ischemic injury after experimental coronary occlusion and reperfusion," Sep. 1983 *Proc. Natl. Acad. Sci. USA* 80:5784-5788.

DeJonghe et al., "Flemish and Dutch mutations in amyloid beta precursor protein have different effects on amyloid beta secretion," Oct. 5, 1998 *Neurobiol. Dis.* 5:281-286.

Deng et al., "Deletion of presenilin 1 hydrophilic loop sequence leads to impaired gamma-secretase activity and exacerbated amyloid pathology," Apr. 5, 2006 *J. Neurosci.* 26(14):3845-3854.

DeStrooper, "Aph-1, Pen-2, and Nicastrin with Presenilin generate an active gamma-Secretase complex," Apr. 10, 2003 *Neuron* 38:9-12.

Esler et al. "Transition-state analogue inhibitors of gamma-secretase bind directly to presenilin-1," Jul. 2000 *Nat. Cell Biol.* 2:428-434.

Fan et al., "Notch pathway inhibition depletes stem-like cells and blocks engraftment in embryonal brain tumors," Aug. 1, 2006 *Cancer Res.* 66(15):7445-7452.

Foster et al., "Glucocorticoids increase the responsiveness of cells in culture to prostaglandin $E_1$," Nov. 1977 *Proc. Natl. Acad. Sci. USA* 74(11):4816-4820.

Frame et al., "Interrelationship between differentiation and malignancy-associated properties in glioma," Mar. 1984 *Br. J. Cancer* 49:269-280.

Gao et al., "A dimeric Smac/diablo peptide directly relieves caspase-3 inhibition by XIAP. Dynamic and cooperative regulation of XIAP by Smac/Diablo," Oct. 19, 2007 *J. Biol. Chem.* 282(42):30718-30727. Available online on Aug. 27, 2007.

Gardner et al., "The complete nucleotide sequence of an infectious clone of cauliflower mosaic virus by M13mp7 shotgun sequencing," Jun. 25, 1981 *Nucleic Acid Res.* 9(12):2871-2888.

Gilbert et al., "Characterization and partial purification of the plasminogen activator from human neuroblastoma cell line, SK-N-SH. A comparison with human urokinase," Jun. 24, 1982 *Biochim. Biophys. Acta* 704:450-460.

Gilbert et al., "Useful proteins from recombinant bacteria," 1980 *Scientific American* 242(4):74-94.

Gomes et al., "Glial fibrillary acidic protein (GFAP): modulation by growth factors and its implication in astrocyte differentiation," May 1999 *Braz. J. Med. Biol. Res.* 32:619-631.

Gossen et al., "Tight control of gene expression in mammalian cells by tetracycline-responsive promoters," Jun. 15, 1992 *Proc. Natl. Acad. Sci. USA* 89:5547-5551.

Grosschedl et al., "Introduction of a μ immunoglobulin gene into the mouse germ line: specific expression in lymphoid cells and synthesis of functional antibody," Oct. 1984 *Cell* 38:647-658.

Haapala et al., "Isolation from cats of an endogenous type C virus with a novel envelope glycoprotein," Mar. 1985 *J. Virol.* 53(3):827-833.

Haass et al., "Mutations associated with a locus for familial Alzheimer's disease result in alternative processing of amyloid beta-protein precursor," Jul. 1, 1994 *J. Biol. Chem.* 269(26):17741-17748.

Hammer et al., "Diversity of alpha-fetoprotein gene expression in mice is generated by a combination of separate enhancer elements," Jan. 2, 1987 *Science* 235:53-58.

Hanahan, "Heritable formation of pancreatic beta-cell tumours in transgenic mice expressing recombinant insulin/simian virus 40 oncogenes," May 9, 1985 *Nature* 315:115-122.

(56) References Cited

OTHER PUBLICATIONS

Hardy et al., "The amyloid hypothesis of Alzheimer's disease: progress and problems on the road to therapeutics," Jul. 19, 2002 *Science* 297:353-356 and one page Erratum dated Sep. 27, 2002.
He et al., "Expression of $O^6$-methylguanine-DNA methyltransferase in six human medulloblastoma cell lines," Mar. 1, 1992 *Cancer Res.* 52:1144-1148.
He et al., "Notch and BCR signaling synergistically promote the proliferation of Raji B-lymphoma cells," Jun. 2009 *Leuk. Res.* 33:798-802. Available online on Oct. 19, 2008.
Herrera-Estrella et al., "Expression of chimaeric genes transferred into plant cells using a Ti-plasmid-derived vector," May 19, 1983 *Nature* 303:209-213.
Herrera-Estrella et al., "Light-inducible and chloroplast-associated expression of a chimaeric gene introduced into *Nicotiana tabacum* using a Ti plasmid vector," Jul. 12, 1984 *Nature* 310:115-120.
Hubmann et al., "Notch2 is involved in the overexpression of CD23 in B-cell chronic lymphocytic leukemia," May 15, 2002 *Blood* 99:3742-3747.
Ida et al., "Analysis of heterogeneous βA4 peptides in human cerebrospinal fluid and blood by a newly developed sensitive Western blot assay," Sep. 13, 1996 *J. Biol. Chem.* 271(37):22908-22914.
Ikeuchi et al., "The Notch ligands Delta1 and Jagged2 are substrates for presenilin-dependent 'gamma-secretase' cleavage," Mar. 7, 2003 *J. Biol. Chem.* 278(10):7751-7754. Available online on Jan. 24, 2003.
Jarrett et al., "The carboxy terminus of the beta amyloid protein is critical for the seeding of amyloid formation: implications for the pathogenesis of Alzheimer's disease," May 11, 1993 *Biochem.* 32(18):4693-4697.
Kang et al., "The precursor of Alzheimer's disease amyloid A4 protein resembles a cell-surface receptor," Feb. 19, 1987 *Nature* 325:733-736.
Kelsey et al., "Species- and tissue-specific expression of human alpha$_1$-antitrypsin in transgenic mice," Apr. 1987 *Genes Dev.* 1:161-171.
Khorkova et al., "Modulation of amyloid precursor protein processing by compounds with various mechanisms of action: detection by liquid phase electrochemiluminescent system," Aug. 1, 1998 *J. Neurosci. Meth.* 82:159-166.
Kitaguchi et al., "Novel precursor of Alzheimer's disease amyloid protein shows protease inhibitory activity," Feb. 11, 1988 *Nature* 331:530-532.
Kogoshi et al., "Gamma-secretase inhibitors suppress the growth of leukemia and lymphoma cells," Jul. 2007 *Oncol. Rep.* 18:77-80.
Kojro et al., "The non-amyloidogenic pathway: structure and function of alpha-secretases," 2005 *Subcell. Biochem.* 38:105-127.
Kollias et al., "Regulated expression of human $^A$gamma-, beta-, and hybrid gamma/beta-globin genes in transgenic mice: manipulation of the developmental expression patterns," Jul. 4, 1986 *Cell* 46:89-94.
Kopan et al., "A common enzyme connects Notch signaling and Alzheimer's disease," Nov. 15, 2000 *Genes. Dev.* 14:2799-2806.
Kounnas et al., "Modulation of gamma-secretase reduces beta-amyloid deposition in a transgenic mouse model of Alzheimer's disease," Sep. 9, 2010 *Neuron* 67:769-780.
Krumlauf et al., "Developmental regulation of alpha-fetoprotein genes in transgenic mice," Jul. 1985 *Mol. Cell. Biol.* 5(7):1639-1648.
Kruse et al., "Characterization of a continuous human glioma cell line DBTRG-05MG: growth kinetics, karyotype, receptor expression, and tumor suppressor gene analyses," Sep.-Oct. 1992 *In Vitro Cell. Dev. Biol.* 28A:609-614.
Kuo et al., "Water-soluble Abeta (N-40, N-42) oligomers in normal and Alzheimer disease brains," Feb. 23, 1996 *J. Biol. Chem.* 271(8):4077-4081.
Lai et al., "Presenilin-1 and presenilin-2 exhibit distinct yet overlapping gamma-secretase activities," Jun. 20, 2003 *J. Biol. Chem.* 278(25):22475-22481. Available online on Apr. 8, 2003.
Lammich et al., "Presenilin-dependent intramembrane proteolysis of CD44 leads to the liberation of its intracellular domain and the secretion of an Abeta-like peptide," Nov. 22, 2002 *J. Biol. Chem.* 277(47):44754-44759. Available online on Sep. 9, 2002.

Leder et al., "Consequences of widespread deregulation of the c-myc gene in transgenic mice: multiple neoplasms and normal development," May 23, 1986 *Cell* 45:485-495.
Lei et al., "Soluble oligomers of the intramembrane serine protease YqgP are catalytically active in the absence of detergents," Nov. 18, 2008 *Biochem.* 47:11920-11929. Available online on Oct. 21, 2008.
Li et al., "Photoactivated γ-secretase inhibitors directed to the active site covalently label presenilin 1," Jun. 8, 2000 *Nature* 405:689-694.
Li et al., "Presenilin 1 is linked with γ-secretase activity in the detergent solubilized state," May 23, 2000 *Proc. Natl. Acad. Sci. USA* 97(11):6183-6143.
Li, Yueming, "Regulation and Function of Gamma-Secretase," Grant Abstract, Grant No. AG026660 [online]. National Institute on Aging, National Institutes of Health, project dates Aug. 1, 2005 to Jul. 31, 2011 [retrieved on Jan. 7, 2011]. Retrieved from the Internet: <http://projectreporter.nih.gov/pr_Prj_info_desc_dtls.cfm?aid=7663911&icde=6610158&print=yes>; 2 pgs.
Lichtenthaler et al., "Mutations in the transmembrane domain of APP altering γ-secretase specificity," Dec. 9, 1997 *Biochem.* 36:15396-15403.
Lichtenthaler et al., "A novel substrate for analyzing Alzheimer's disease gamma-secretase," Jun. 25, 1999 *FEBS Lett.* 453:288-292.
Logan et al., "Adenovirus tripartite leader sequence enhances translation of mRNAs late after infection," Jun. 1984 *Proc. Natl. Acad. Sci. USA* 81:3655-3659.
Lowy et al., "Isolation of transforming DNA: cloning the hamster aprt gene," Dec. 1980 *Cell* 22:817-823.
MacDonald, "Expression of the pancreatic elastase I gene in transgenic mice," Jan.-Feb. 1987 *Hepatology* 7(1):42S-51S.
Magram et al., "Developmental regulation of a cloned adult β-globin gene in transgenic mice," May 23, 1985 *Nature* 315:338-340.
Marciniszyn et al., "Mode of inhibition of acid proteases by pepstatin," Nov. 25, 1976 *J. Biol. Chem.* 251(22):7088-7094.
Mason et al., "The hypogonadal mouse: reproductive functions restored by gene therapy," Dec. 12, 1986 *Science* 234:1372-1378.
McCafferty et al., "Mutational Analysis of Potential Zinc-Binding Residues in the Active Site of the Enterococcal D-Ala-D-Ala Dipeptidase VanX," Aug. 26, 1997 *Biochem.* 36:10498-10505.
Morelli et al., "Neuronal and glial cell type-specific promoters within adenovirus recombinants restrict the expression of the apoptosis-inducing molecule Fas ligand to predetermined brain cell types, and abolish peripheral liver toxicity," Mar. 1999 *J. Gen. Virol.* 80:571-583.
Mulligan et al., "Selection for animal cells that express the *Escherichia coli* gene coding for xanthine-guanine phosphoribosyltransferase," Apr. 1981 *Proc. Natl. Acad. Sci. USA* 78(4):2072-2076.
National Center for Biotechnology Information, National Library of Medicine, National Institutes of Health, GenBank Locus AAC83813, Accession No. AAC83813, "maltose binding protein [Expression vector pMBP-parallel1]," [online]. Bethesda, MD [retrieved on Jan. 10, 2011]. Retrieved from the Internet: < http://www.ncbi.nlm.nih.gov/protein/3983122>; 1 pg.
National Center for Biotechnology Information, National Library of Medicine, National Institutes of Health, GenBank Locus NM_003183, Accession No. NM_003183, "*Homo sapiens* ADAM metallopeptidase domain 17 (ADAM17), mRNA," [online]. Bethesda, MD [retrieved on Jan. 10, 2011]. Retrieved from the Internet: < http://www.ncbi.nlm.nih.gov/nuccore/73747888>; 5 pgs.
National Center for Biotechnology Information, National Library of Medicine, National Institutes of Health, GenBank Locus Y00264, Accession No. Y00264, "Human mRNA for amyloid A4 precursor of Alzheimer's disease," [online]. Bethesda, MD [retrieved on Jan. 7, 2011]. Retrieved from the Internet: <http://www.ncbi.nlm.nih.gov/nuccore/28525>; 2 pgs.
Nilsberth et al., "The 'Arctic' APP mutation (E693G) causes Alzheimer's disease by enhanced Abeta protofibril formation," Sep. 2001 *Nat. Neurosci.* 4(9):887-893.
Nitsch et al., "Release of Alzheimer amyloid precursor derivatives stimulated by activation of muscarinic acetylcholine receptors," Oct. 9, 1992 *Science* 258:304-307.

(56) References Cited

OTHER PUBLICATIONS

O'Hare et al., "Transformation of mouse fibroblasts to methotrexate resistance by a recombinant plasmid expressing a prokaryotic dihydrofolate reductase," Mar. 1981 *Proc. Natl. Acad Sci. USA* 78(3):1527-1531.
Olmsted et al., "Isolation of microtubule protein from cultured mouse neuroblastoma cells," Jan. 1970 *Proc. Natl. Acad. Sci. USA* 65(1):129-136.
Olopade et al., "Molecular analysis of deletions of the short arm of chromosome 9 in human gliomas," May 1, 1992 *Cancer Res.* 52:2523-2529.
Ornitz et al., "Elastase I promoter directs expression of human growth hormone and SV40 T antigen genes to pancreatic acinar cells in transgenic mice," 1985 *Cold Spring Harbor Symp. Quant. Biol.* 50:399-409.
Pinkert et al., "An albumin enhancer located 10 kb upstream functions along with its promoter to direct efficient, liver-specific expression in transgenic mice," May 1987 *Genes Dev.* 1:268-276.
Placanica et al., "Characterization of an Atypical γ-Secretase Complex from Hematopoietic Origin," Apr. 6, 2010 *Biochem.* 49:2796-2804. Available online on Feb. 23, 2010.
Placanica et al., "Gender- and age-dependent gamma-secretase activity in mouse brain and its implication in sporadic Alzheimer disease," 2009 *PloS One* 4(4):e5088; 9 pgs. Available online on Apr. 7, 2009.
Placanica et al., "Pen2 and presenilin-1 modulate the dynamic equilibrium of presenilin-1 and presenilin-2 gamma-secretase complexes," Jan. 30, 2009 *J. Biol. Chem.* 284(5):2967-2977. Available online on Nov. 25, 2008.
Ponte et al., "A new A4 amyloid mRNA contains a domain homologous to serine proteinase inhibitors," Feb. 11, 1988 *Nature* 331:525-527.
Pontén et al., "Long term culture of normal and neoplastic human glia," 1968 *Acta Pathol. Microbiol. Scand.* 74:465-486.
Postina et al., "A disintegrin-metalloproteinase prevents amyloid plaque formation and hippocampal defects in an Alzheimer disease mouse model," May 2004 *J. Clin .Invest.* 113(10):1456-1464.
Postina et al., "Erratum: A disintegrin-metalloproteinase prevents amyloid plaque formation and hippocampal defects in an Alzheimer disease mouse model," Aug. 2004 *J. Clin .Invest.* 114(4):598-599.
Radany et al., "Directed establishment of rat brain cell lines with the phenotypic characteristics of type 1 astrocytes," Jul. 15, 1992 *Proc. Natl. Acad Sci. USA* 89:6467-6471.
Readhead et al., "Expression of a myelin basic protein gene in transgenic shiverer mice: correction of the dysmyelinating phenotype," Feb. 27, 1987 *Cell* 48:703-712.
Reed, "Molecular biology of chronic lymphocytic leukemia," Feb. 1998 *Semin. Oncol.* 25(1):11-18.
Santerre et al., "Expression of prokaryotic genes for hygromycin B and G418 resistance as dominant-selection markers in mouse L cells," Oct. 1984 *Gene* 30:147-156.
Schatz, "Use of Peptide Libraries to Map the Substrate Specificity of a Peptide-Modifying Enzyme: A 13 Residue Consensus Peptide Specifies Biotinylation in *Escherichia coli*," Oct. 1993 *Nat. Biotechnol.* 11:1138-1143.
Seiffert et al., "Presenilin-1 and -2 are molecular targets for gamma-secretase inhibitors," Nov. 3, 2000 *J. Biol. Chem.* 275(44):34086-34091.
Selkoe et al., "In search of gamma-secretase: presenilin at the cutting edge," May 23, 2000 *Proc. Natl. Acad. Sci. USA* 97:5690-5692.
Selkoe et al., "Notch and Presenilin: regulated intramembrane proteolysis links development and degeneration," 2003 *Ann. Rev. Neurosci.* 26:565-597. Available online on Apr. 18, 2003.
Selkoe, "Alzheimer's disease: genes, proteins, and therapy," Apr. 2001 *Physiol. Rev.* 81(2):741-766.
Selkoe, "The cell biology of beta-amyloid precursor protein and presenilin in Alzheimer's disease," Nov. 1998 *Trends Cell Bio.* 8:447-453.
Selkoe, "Translating cell biology into therapeutic advances in Alzheimer's disease," Jun. 24, 1999 *Nature* 399:A23-A31.

Shah et al., "Nicastrin functions as a gamma-secretase-substrate receptor," Aug. 12, 2005 *Cell* 122:435-447.
Shani, "Tissue-specific expression of rat myosin light-chain 2 gene in transgenic mice," Mar. 21, 1985 *Nature* 314:283-286.
Shearman et al., "L-685,458, an aspartyl protease transition state mimic, is a potent inhibitor of amyloid β-protein precursor γ-secretase activity," Aug. 1, 2000 *Biochem.* 39:8698-8704. Available online on Jul. 6, 2000.
Shelton et al., "A miniaturized 1536-well format gamma-secretase assay," Oct. 2009 *Assay Drug Dev. Technol.* 7(5):461-470.
Shelton et al., "Modulation of gamma-secretase specificity using small molecule allosteric inhibitors," Dec. 1, 2009 *Proc. Natl. Acad. Sci. USA* 106(48):20228-20233. Available online on Nov. 11, 2009.
Six et al., "The Notch ligand Delta1 is sequentially cleaved by an ADAM protease and gamma-secretase," Jun. 24, 2003 *Proc. Natl. Acad. Sci. USA* 100:7638-7643. Available online on Jun. 6, 2003.
Skovronsky et al., "Protein kinase C-dependent alpha-secretase competes with beta-secretase for cleavage of amyloid-beta precursor protein in the trans-golgi network," Jan. 28, 2000 *J. Biol. Chem.* 275(4):2568-2575.
Steinhilb et al., "ELISA analysis of beta-secretase cleavage of the Swedish amyloid precursor protein in the secretory and endocytic pathways," Mar. 2002 *J. Neurochem.* 80:1019-1028.
Stephens et al., "Metabolites of the beta-amyloid precursor protein generated by beta-secretase localise to the trans-Golgi network and late endosome in 293 cells," Oct. 15, 1996 *J. Neurosci. Res.* 46:211-225.
Struhl et al., "Requirements for presenilin-dependent cleavage of notch and other transmembrane proteins," Sep. 2000 *Mol. Cell.* 6:625-636.
Sugimoto et al., "Determination of cell surface membrane antigens common to both human neuroblastoma and leukemia-lymphoma cell lines by a panel of 38 monoclonal antibodies," Jul. 1984 *J. Natl. Can. Inst.* 73(1):51-57.
Swift et al., "Tissue-specific expression of the rat pancreatic elastase I gene in transgenic mice," Oct. 1984 *Cell* 38:639-646.
Szybalska et al., "Genetics of human cell lines, IV. DNA-mediated heritable transformation of a biochemical trait," Dec. 15, 1962 *Proc. Natl. Acad. Sci. USA* 48:2026-2034.
Tabuchi et al., "Inducibility of BDNF gene promoter I detected by calcium-phosphate-mediated DNA transfection is confined to neuronal but not to glial cells," Dec. 30, 1998 *Biochem. Biophys. Res. Comm.* 253:818-823.
Thinakaran et al., "Amyloid precursor protein trafficking, processing, and function," Oct. 31, 2008 *J. Biol. Chem.* 283(44):29615-29619. Available online on Jul. 23, 2008.
Tian et al., "An APP inhibitory domain containing the Flemish mutation residue modulates gamma-secretase activity for Abeta production," Feb. 2010 *Nat. Struct. Mol. Biol.* 17(2):151-158. Available online on Jan. 10, 2010.
Tian et al., "Dual role of alpha-secretase cleavage in the regulation of gamma-secretase activity for amyloid production," Oct. 15, 2010 *J. Biol. Chem.* 285(42):32549-32556. Available online on Jul. 30, 2010.
Trowbridge et al., "Establishment and characterization of ferret cells in culture," Nov. 1982 *In Vitro* 18(11):952-960.
Tumilowicz et al., "Definition of a continuous human cell line derived from neuroblastoma," Aug. 1970 *Cancer Res.* 30:2110-2118.
Universal Protein Resource (UniProt) Consortium, UniProt Knowledgebase (UniProtKB), UniProtKB/Swiss-Prot Ref. P05067 (A4_HUMAN), "Amyloid beta A4 protein," [online]. Washington, D.C. [retrieved on Jan. 7, 2011]. Retrieved from the Internet: <http://www.uniprot.org/uniprot/P05067>; 44 pgs.
Vassar et al., "β-secretase cleavage of Alzheimer's amyloid precursor protein by the transmembrane aspartic protease BACE," Oct. 22, 1999 *Science* 286:735-741.
Vetrivel et al., "Evidence that CD147 modulation of beta-amyloid (Abeta) levels is mediated by extracellular degradation of secreted Abeta," Jul. 11, 2008 *J. Biol. Chem.* 283(28):19489-19498. Available online on May 1, 2008.
Villa-Kamaroff et al., "A bacterial clone synthesizing proinsulin," Aug. 1978 *Proc. Natl. Acad. Sci. USA* 75(8):3727-3731.
Voet et al., *Biochemistry*, John Wiley & Sons: New York, NY; copyright 1990. Cover page, publisher's page, and p. 66-71.

(56) References Cited

OTHER PUBLICATIONS

Wagner et al., "Nucleotide sequence of the thymidine kinase gene of herpes simplex virus type 1," Mar. 1981 *Proc. Natl. Acad. Sci. USA* 78(3):1441-1445.
Weng et al., "Activating mutations of NOTCH1 in human T cell acute lymphoblastic leukemia," Oct. 2004 *Science* 306:269-271.
Wigler et al., "Transfer of purified herpes virus thymidine kinase gene to cultured mouse cells," May 1977 *Cell* 11:223-232.
Wigler et al., "Transformation of mammalian cells with an amplifiable dominant-acting gene," Jun. 1980 *Proc. Natl. Acad. Sci. USA* 77(6):3567-3570.
Wolfe et al., "Two transmembrane aspartates in presenilin-1 required for presenilin endoproteolysis and γ-secretase activity," Apr. 8, 1999 *Nature* 398:513-517.
Yamamoto et al., "Identification of a functional promoter in the long terminal repeat of *Rous sarcoma virus*," Dec. 1980 *Cell* 22:787-797.
Yang et al., "Electrochemiluminescence: A new diagnostic and research tool," Feb. 1994 *Nat. Biotechnol.* 12:193-194.
Yang et al., "In vivo manifestation of Notch related phenotypes in zebrafish treated with Alzheimer's amyloid reducing γ-secretase inhibitors," Jun. 2010 J. Neurochem. 113:1200-1209. Available online on Mar. 12, 2010.
Yang et al., "Stereo-controlled synthesis of novel photoreactive γ-secretase inhibitors," Feb. 1, 2009 *Bioorg. Med. Chem. Lett.* 19:922-925.
Yin et al., "γ-Secretase Substrate Concentration Modulates the Abeta42/Abeta40 Ratio: Implications for Alzheimer Disease," Aug. 10, 2007 *J. Biol. Chem.* 282(32):23639-23644. Available online on Jun. 7, 2007.
Zhang et al., "A simple statistical parameter for use in evaluation and validation of high throughput screening assays," Apr. 1999 *J. Biomol. Scrn.* 4(2):67-73.
Zhou et al., "CD147 is a regulatory subunit of the gamma-secretase complex in Alzheimer's disease amyloid beta-peptide production," May 24, 2005 *Proc. Natl. Acad. Sci. USA* 102(21):7499-7504. Available online on May 12, 2005.
Altschul et al, "Basic local alignment search tool," J. Molec. Biol., 1990; 215:403-410.
Amann et al., "Tightly regulated tac promoter vectors useful for the expression of unfused and fused proteins in *Escherichia coli*," *Gene*, Sep. 1988; 69:301-315.
U.S. Appl. No. 13/821,090, filed Mar. 6, 2013, Li et al.
Amtul et al., "A Presenilin 1 Mutation Associated with Familial Frontotemporal Dementia Inhibits γ-Secretase Cleavage of APP and Notch," *Neurobiology of Disease*, 2002; 9(2):269-273.
Artavanis-Tsakonas et al., "Notch Signaling: Cell Fate Control and Signal Integration in Development," *Science*, 1999; 284 (5415): 770-776.
Baldari et al. "A novel leader peptide which allows efficient secretion of a fragment of human interleukin 1 beta in *Saccharomyces cerevisiae*," *EMBO J.*, Jan. 1987; 6:229-234.
Banerji et al., "A lymphocyte-specific cellular enhancer is located downstream of the joining region in immunoglobulin heavy chain genes," *Cell*, Jul. 1983; 33:729-740.
Beel et al., "Substrate Specificity of γ-Secretase and Other Intramembrane Proteases," *Cell Mol Life Sci*, May 2008; 65(9):1311-1334.
Bentahir et al., "Presenilin clinical mutations can affect γ-secretase activity by different mechanisms," *Journal of Neurochemistry*, 2006; 96: 732-742.
Berezovska et al., "The Alzheimer-related gene presenilin 1 facilitates notch 1 in primary mammalian neurons," *Molecular Brain Research*, 1999; 69(2):273-280.
Borchelt et al., "Familial Alzheimer's Disease-Linked Presenilin 1 Variants, Elevate Aβ1-42/1-40 Ratio In Vitro and In Vivo," *Neuron*, 1996; 17:1005-1013.
Brou et al., "A Novel Proteolytic Cleavage Involved in Notch Signaling," *Mol. Cell*, 2000; 5(2):207-216.
Brodeur et al., *Monoclonal antibody Production Techniques and Applications*, Marcel Dekker, Inc., New York, NY, 1987: 51-63.

Byrne et al., "Multiplex gene regulation: A two-tiered approach to transgene regulation in transgenic mice," *PNAS USA*, Jul. 1989; 86:5473-5477.
Calame et al., "Transcriptional Controlling Elements in the Immunoglobulin and T Cell Receptor Loci," *Advances in Immunology*, 1988; 43:235-275.
Camper et al., "Postnatal repression of the alpha-fetoprotein gene is enhancer independent," *Genes & Development*,1989; 3:537-546.
Carrillo et al., "The Multiple Sequence Alignment Problem in Biology," *SIAM J. Applied Math.*, 1988; 48(5):1073.
Chan et al., "Roles for Proteolysis and Trafficking in Notch Maturation and Signal Transduction," *Cell*, 1998; 94:423-426.
Chau et al., "Familial Alzheimer's disease Presenilin-1 mutations alter the active site conformation of γ-secretase," *J. Biol. Chem.*, May 2012; 287:17288-17296.
Chen et al., "Protein Synthesis Post-Translation Modification and Degradation," *Journal of Biological Chemistry*, 2002; 277: 36521-36526.
Chun et al., "Stereoselective Synthesis of Photoreactive Peptidomimetic γ-Secretase Inhibitors," *Journal of Organic Chemistry*, 2004; 69:7344-7347.
Cravatt et al., "Activity-Based Protein Profiling: From Enzyme Chemistry to Proteomic Chemistry," *Annual Review of Biochemistry*, 2008; 77:383-414.
Devereux et al., "A comprehensive set of sequence analysis programs for the VAX," *Nucleic Acids Research*, 1984: 12(1): 387-395.
Duff et al., "Increased amyloid-β42(43) in brains of mice expressing mutant presenilin 1," *Nature*, 1996; 383:710-713.
Edlund et al., "Cell-specific expression of the rat insulin gene: evidence for role of two distinct 5' flanking elements," *Science*, Nov. 1985; 230(4728):912-916.
Esler et al., "Activity-dependent isolation of the presenilin-γ-secretase complex reveals nicastrin and a γ substrate," *PNAS*, 2002; 99(5): 2720-2725.
Gandy et al., "Alzheimer's presenilin 1 modulates sorting of APP and its carboxyl-terminal fragments in cerebral neurons in vivo," *Journal of Neurochemistry*, 2007; 102(3):619-626.
Goding, *Monoclonal Antibodies: Principles and Practice*, Academic Press; 1986:59-103.
Goeddel, *Gene Expression Technology: Methods in Enzymology 185*, Academic Press, San Diego, CA, 1990.
Golde et al., "Avoiding Unintended Toxicity," *Science*, May 2009; 324:603-604.
Gottesman, *Gene Expression Technology: Methods in Enzymology 185*, Academic Press, San Diego, CA, 1990:119-128.
Gribskov et al., eds, *Sequence Analysis Primer*, M Stockton Press, New York; 1991.
Griffin and Griffin, eds., *Computer Analysis of Sequence Data, Part I.*, Humana Press, New Jersey, 1994.
Henikoff, "Amino acid substitution matrices from protein blocks," *PNAS USA*, Nov. 1992; 89:10915-10919.
Hopp et al., "Prediction of protein antigenic determinants from amino acid sequences," *PNAS*, 1981; 78:3824-3828.
Huse et al., "Generation of a large combinatorial library of the immunoglobulin repertoire in phage lambda," *Nature*, Dec. 1989; 1275-1281.
International Preliminary Report on Patentability issued Mar. 12, 2013, in Switzerland for International Patent Application No. PCT/US2011/050688, filed Sep. 7, 2011.
International Search Report mailed Jun. 29, 2012, in Korea for International Patent Application No. PCT/US2011/050688, filed Sep. 7, 2011.
Kaufman et al., "Translational efficiency of polycistronic mRNAs and their utilization to express heterologous genes in mammalian cells," *EMBO J.*, 1987; 6:187-193.
Keller et al., "A Faster Migrating Variant Masquerades as NICD When Performing in Vitro γ-Secretase Assays with Bacterially Expressed Notch Substrates," *Biochemistry*, 2006; 45:5351-5358.
Kessel et al., "Murine developmental control genes," *Science*, Jul. 1990; 249:374-379.
Kohler et al., "Continuous cultures of fused cells secreting antibody of predefined specificity," *Nature*, 1975; 256:495-497.

(56) References Cited

OTHER PUBLICATIONS

Kopan et al., "Signal transduction by activated mNotch: Importance of proteolytic processing and its regulation by the extracellular domain," *PNAS*, 1996; 93:1683-1688.
Kozbor, "A human hybrid myeloma for production of human monoclonal antibodies," *J Immunol.*, 1984; 133:3001-5.
Kurjan et al. "Structure of a yeast pheromone gene (MFα): A putative α-factor precursor contains four tandem copies of mature α-factor," *Cell*, Oct. 1982; 30:933-943.
Kyte et al., "A simple method for displaying the hydropathic character of a protein," *Journal of Molecular Biology*, May 1982; 157:105-132.
Lee et al. "Hyperaccumulation of FAD-linked presenilin 1 variants in vivo," *Nature Medicine*, 1997; 3:756-760.
Lesk, A.M., ed., *Computational Molecular Biology*, Oxford University Press; New York, NY, 1988.
Levy-Lahad et al., "Candidate gene for the chromosome 1 familial Alzheimer's disease locus," *Science*, 1995; 269:973-977.
Luckow et al, "High level expression of nonfused foreign genes with *Autographa californica* nuclear polyhedrosis virus expression vectors," *Virology*, May 1989; 170:31-39.
Marambaud et al., "A presenilin-1/-secretase cleavage releases the E-cadherin intracellular domain and regulates disassembly of adherens junctions," *The EMBO Journal*, 2002; 21:1948-1956.
Marambaud et al., "A CBP Binding Transcriptional Repressor Produced by the PS1/e-Cleavage of N-Cadherin Is Inhibited by PS1 FAD Mutations," *Cell*, 2003; 114: 635-645.
Moehlmann et al., "Presenilin-1 mutations of leucine 166 equally affect the generation of the Notch and APP intracellular domains independent of their effect on Aβ42 production," *PNAS*; 2002; 99:8025-8030.
Morrison, "Success in Specification," *Nature*, Apr. 1994; 368:812-813.
Müller et al., "Physiological Functions of APP Family Proteins," *Cold Spring Harbor Perspectives in Medicine*, Feb. 2012; 2(2): a006288.
Munson et al., "LIGAND: A versatile computerized approach for characterization of ligan-binding systems," *Analytical Biochemistry*, 1980; 107:220-239.
Murayama et al., "Twenty-nine missense mutations linked with familial Alzheimer's disease alter the processing of presenilin 1," *Progress in Neuro-Psychopharmacology and Biological Psychiatry*, 1999; 23(5): 905-913.
Nakajima et al., "Notch-1 activation by familial Alzheimer's disease (FAD)-linked mutant forms of presenilin-1," *Journal of Neuroscience Research*, 2000; 62:311-317.
National Center for Biotechnology Information, National Library of Medicine, National Institutes of Health, GenBank Locus AF308602, Accession No. AF308602, "*Homo sapiens* NOTCH 1 (N1) mRNA, complete cds," [online]. Bethesda, MD [retrieved on Aug. 2, 2013]. Retrieved from the Internet: <http://www.ncbi.nlm.nih.gov/nuccore/af308602>; 3 pgs.
National Center for Biotechnology Information, National Library of Medicine, National Institutes of Health, GenBank Locus XP_002810439, Accession No. XP_002810439, "PREDICTED: synaptonemal complex protein 1 isoform 2 [*Pongo abelii*]," [online]. Bethesda, MD [retrieved on Aug. 2, 2013]. Retrieved from the Internet: <http://www.ncbi.nlm.nih.gov/protein/XP_002810439.1>; 1 pg.
Needleman et al., "Needleman-Wunsch Algorithm for Sequence Similarity Searches," *J. Mol. Biol.*, 1970; 48: 443-453.
Neet et al., "Thematic Minireview Series on the Molecular Basis of alzheimer Disease," *The Journal of Biological Chemistry*, Oct. 2008; 283(44):29613-29614.

Queen et al., "Immunoglobulin gene transcription is activated by downstream sequence elements," *Cell*, Jul. 1983; 33:741-748.
Redmond et al., "Nuclear Notch1 signaling and the regulation of dendritic development," *Nature Neuroscience*, 2000; 3:30-40.
Sambrook et al., *Molecular Cloning: A Laboratory Manual, 2nd Ed.*, Cold Spring Harbor Laboratory, Cold Spring Harbor Laboratory Press, Cold Spring Harbor, NY, 1989, Chapters 16 and 17.
Sato et al., "Enzyme Catalysis and Regulation," *Journal of Biological Chemistry*, 2003; 278:24294-24301.
Schechter et al., "On the size of the active site in proteases. I. Papain," *Biochemical and Biophysical Research Communications*, 1967; 27(2):157-162.
Schultz et al., "Expression and secretion in yeast of a 400-kda envelope glycoprotein derived from epstein-barr virus," *Gene*, 1987; 54:113-123.
Seed, "An LFA-3 cDNA encodes a phospholipid-linked membrane protein homologous to its receptor CD2," *Nature*, Oct. 1987; 329:840-842.
Serneels et al., "γ-Secretase Heterogeneity in the aph1 Subunit: Relevance for Alzheimer's Disease," *Science*, May 2009; 324:639-642.
Shelton et al., "An exo-cell assay for examining real-time γ-secretase activity and inhibition," *Molecular Neurodegeneration*, 2009; 4:22.
Sherrington et al., "Cloning of a gene bearing missense mutations in early-onset familial Alzheimer's disease," *Nature*, 1995; 375:754-760.
Smith et al., "Production of Human Beta Interferon in Insect Cells Infected with a Caculovirus Expression Vector," *Mol Cell Biol*, 1983; 3:2156-2165.
Smith et al., "Single-step purification of polypeptides expressed in *Escherichia coli* as fusions with glutathione S-transferase," *Gene*, Jul. 1988: 67:31-40.
Smith, D. W., ed., *Biocomputing: Informatics and Genome Projects*, Academic Press, New York, NY, 1993.
Song et al., "Proteolytic release and nuclear translocation of Notch-1 are induced by presenilin-1 and impaired by pathogenic presenilin-1 mutations," *PNAS*, 1999; 96 (12): 6959-6963.
Studier et al., *Gene Expression Technology: Methods in Enzymology 185*, Academic Press, San Diego, CA, 1990:60-89.
Takami et al., "γ-Secretase: Successive Tripeptide and Tetrapeptide Release from the Transmembrane Domain of β-Carboxyl Terminal Fragment," *Journal of Neuroscience*, 2009; 29(41):13042-13052.
van Tetering et al., "Metalloprotease ADAM10 Is Required for Notch 1 Site 2 Cleavage," *J. Biol. Chem.*, 2009; 284(45): 31018-31027.
von Heijne, G., *Sequence Analysis in Molecular Biology*, Academic Press, New York, 1987.
Wada et al., "Codon usage tabulated from the GenBank genetic sequence data," *Nucleic Acids Research*, May 1992; 20(Suppl):2111-2118.
Wang et al., "Presenilin 1 familial Alzheimer's disease mutation leads to defective associative learning and impaired adult neurogenesis," *Neuroscience*, 2004; 126(2):305-312.
Wang et al., "Wild-type Presenilin 1 Protects against Alzheimer Disease Mutation-induced Amyloid Pathology," *J. Biol. Chem.*, 2006; 281:15330-15336.
Wilkinson, "Ultimate Abs," *The Scientist*, Apr. 2000; 14(8): pp. 25-28.
Winoto et al., "A novel, inducible and T cell-specific enhancer located at the 3' end of the T cell receptor α locus," *EMBO J.*, 1989; 8(3):729-733.
Written Opinion mailed Jun. 29, 2012, in Korea for International Patent Application No. PCT/US2011/050688, filed Sep. 7, 2011.
Zheng et al., "The amyloid precursor protein: beyond amyloid," *Molecular Neurodegeneration*, Jul. 2006; 1:5.

* cited by examiner

E

PS1-NTF

F

US 9,023,767 B2

γ-SECRETASE SUBSTRATES AND METHODS OF USE

STATEMENT REGARDING FEDERALLY SPONSORED RESEARCH OR DEVELOPMENT

The disclosures of the present application were developed with support from the U.S. Government (NIH grant AG026660), and the Government has certain rights in any patents granted on such disclosures.

REFERENCE TO A SEQUENCE LISTING

Table 1, Table of Sequences, is placed at the beginning of Section 6, Detailed Description of the Invention. The Sequence List appears following the Abstract of this disclosure.

1. FIELD OF THE INVENTION

The present invention provides novel substrates and methods for measuring gamma-secretase ("γ-secretase") activity and assays for identifying modulators of gamma-secretase activity. Specifically, this disclosure describes newly designed substrates for use in high sensitivity assays for γ-secretase activity. In addition, γ-secretase substrates toward which γ-secretase has high activity comprising modifications in a domain identified herein as the γ-secretase inhibitory domain are disclosed, as are assays for their use in measuring γ-secretase activity. Because of their increased sensitivity to γ-secretase, γ-secretase substrates identified herein can be used in assays to identify γ-secretase inhibitors.

2. BACKGROUND OF THE INVENTION

Alzheimer's disease (AD) is the most prevalent form of dementia. It is a neurodegenerative disorder, clinically characterized by progressive loss of memory and general cognitive function, and pathologically characterized by the deposition of extracellular proteinaceous plaques in the cortical and associative brain regions of sufferers. These plaques mainly comprise fibrillar aggregates of beta-amyloid peptide (Aβ). Aβ is formed from amyloid precursor protein (APP). APP is a ubiquitous membrane-spanning (type 1) glycoprotein, of which three major isoforms (APP695, APP751, and APP770; SEQ ID NOS:1-3, respectively) are known, that undergoes a variety of proteolytic processing events (Selkoe, 1998, *Trends Cell Biol.* 8:447-453). APP in general is disposed with its N-terminal portion in the extracellular space or in the lumen of an intracellular organelle such as the Golgi or an endosome, a transmembrane portion, and its C-terminal portion extends into the cytosol (Thinakaran and Koo, 2008, *J. Biol. Chem.* 283:29615-19619).

Generation of Aβ from APP occurs via separate intracellular proteolytic events involving the enzymes beta-secretase and gamma-secretase. Beta-secretase (also called BACE1) first cleaves APP within the extracellular domain to shed the soluble N-terminal APP-sbeta or sAPPβ (SEQ ID NO:5), leaving the beta-CTF (C-terminal fragment; SEQ ID NO:8) membrane-bound. The latter is then further processed by gamma-secretase to release Aβ and gamma-CTF, or AICD (APP intracellular domain). Given that gamma-secretase cleaves beta-CTF, beta-CTF has widely been used to monitor gamma-secretase activity in cell based and in vitro assays. The gamma-secretase cleavage site of APP is situated within a transmembrane domain; indeed gamma secretase represents one of small number of proteases that act within a membrane milieu. (See FIG. 1 for a schematic diagram of proteolytic cleavages of APP leading to Aβ and other polypeptide products.) Variability in the site of gamma-secretase mediated proteolysis results in Aβ peptides of varying chain lengths comprising heterogeneous C-termini, e.g. Aβ (1-38, "Aβ38"; SEQ ID NO:15), Aβ (1-40, "Aβ40"; SEQ ID NO:16) and Aβ (1-42, "Aβ42"; SEQ ID NO:17). (See FIG. 9A for the portion of the APP sequence containing the cleavage sites of the various secretase activities.) After secretion into the extracellular medium, the initially-soluble Aβ forms soluble oligomeric aggregates, ultimately resulting in the insoluble deposits and dense neuritic plaques which are one of the pathological hallmarks of AD. Aβ42 is more prone to aggregation than Aβ40 and is the major component of amyloid plaque (Jarrett, et al., 1993, *Biochemistry* 32:4693-4697; Kuo, et al., 1996, *J. Biol. Chem.* 271:4077-4081).

Alternatively, APP can be sequentially cleaved by alpha-secretase and gamma-secretase to produce soluble APP-alpha, or sAPPα (SEQ ID NO:4), P3 and gamma-CTF (FIG. 1). Alpha-secretase cleavage occurs at a site distinct from the cleavage site of beta-secretase and precludes the formation of Aβ peptides.

Various interventions in the plaque-forming process have been proposed as therapeutic treatments for AD (see, e.g., Hardy and Selkoe, 2002, *Science* 297:353-356). One such method of treatment that has been proposed is that of blocking or attenuating the production of Aβ, for example, by inhibition of beta- or gamma-secretase. Other proposed methods of treatment include administering a compound(s) which blocks the aggregation of Aβ, or administering an antibody which selectively binds to Aβ. Activation of α-secretase is also an appealing strategy for the development of AD therapy, in that increased alpha-secretase cleavage might lend to lessened Aβ generation.

Gamma-secretase is a macromolecular proteolytic complex composed of at least four proteins: presenilin (PS), nicastrin (NCT), PEN-2 and APH-1 (De Strooper, 2003, *Neuron* 38:9-12). Recently, CD147 and TMP21 have been found to be associated with the gamma-secretase complex (Chen, et al., 2006, *Nature* 440:1208-1212; Zhou et al., 2005, *Proc. Natl. Acad. Sci. USA,* 102:7499-7504). Among these known components, PS is believed to contain the active site of gamma-secretase, recognized as an aspartyl protease (Esler et al., 2000, *Nat. Cell. Biol.,* 2:428:434; Li et al., 2000, *Nature* 405:689-694; Wolfe et al., 1999, *Nature* 398:513-517). Considerable effort has been made to understand the process of gamma-secretase substrate recognition and its catalytic machinery. A PS-dependent protease can process any single-pass transmembrane (TM) protein regardless of its primary sequence as long as the TM protein extracellular domain is smaller than 300 amino acids. Moreover, the size of the extracellular domain appears to determine the efficiency of substrate cleavage (Struhl and Adachi, 2000, *Mol. Cell.* 6:625-636).

The sequential cleavage of APP by two proteases (beta- or alpha-secretase followed gamma-secretase) is analogous to a recently defined signaling paradigm, known as regulated intramembrane proteolysis (RIP) (Brown et al., 2000, *Cell* 100:391-398). RIP generally requires two proteolytic steps to initiate its signaling cascade, whereby the second intramembrane cleavage is dependent on the first cleavage. Indeed, Notch, a type I transmembrane protein, employs RIP and is a substrate for gamma-secretase cleavage. It has been determined that γ-secretase cleaves a multitude of other substrates that include the Notch receptors (Kopan R, Goate A: A common enzyme connects Notch signaling and Alzheimer's disease. Genes Dev 2000, 14(22):2799-2806), ErbB-4 (Kopan R, Goate A: A common enzyme connects notch signaling and Alzheimer's disease. Genes Dev 2000, 14(22):2799-2806), CD44 (Lammich S, Okochi M, Takeda M, Kaether C, Capell A, Zimmer A K, Edbauer D, Walter J, Steiner H, Haass C: Presenilin-dependent intramembrane proteolysis of CD44 leads to the liberation of its intracellular domain and the secretion of an Abeta-like peptide. J Biol Chem 2002, 277 (47):44754-44759), as well as the Notch ligands Delta-1 and Jagged-2 (Six E, Ndiaye D, Laabi Y, Brou C, Gupta-Rossi N, Israel A, Logeat F: The Notch ligand Deltal is sequentially cleaved by an ADAM protease and gamma-secretase. Proc Natl Acad Sci USA 2003, 100(13):7638-7643; Ikeuchi T, Sisodia S S: The Notch ligands, Deltal and Jagged2, are substrates for presenilin-dependent "gamma-secretase" cleavage. J Biol Chem 2003, 278(10):7751-7754; and others). Deregulated Notch signaling has been associated with the development of various cancers, including T-cell Acute Lymphoblastic Leukemia (T-ALL) (Weng A P, Ferrando A A, Lee W, Morris J Pt, Silverman L B, Sanchez-Irizarry C, Blacklow S C, Look A T, Aster J C: Activating mutations of NOTCH1 in human T cell acute lymphoblastic leukemia. Science 2004, 306(5694):269-271). As such, inhibitors of gamma-secretase activity might not only have implications in the treatment of AD, but may also have benefit in treatment of all diseases in which gamma-secretase plays a role.

3. SUMMARY OF THE INVENTION

This disclosure presents polypeptide substrates based on modifications or fragments of the various APP isoforms, assay methods based on the use of these substrates, and screening methods directed toward identifying inhibitors of γ-secretase activity. In several cases, the assay methods and the screening methods are adapted for use in high throughput multi-well plate assay apparatuses. In many embodiments the substrate polypeptides are labeled for ease of detection, and/or may bind specific ligands that themselves are labeled. Generally the labels promote high specificity as well as high sensitivity of detection. These features render the assay and screening methods that employ the labeled substrates especially suited for use in high throughput assay formats. This disclosure further identifies small polypeptides based on a subsequence motif of Aβ that are shown herein to be potent inhibitors of the activity of γ-secretase.

In one aspect this disclosure presents a high sensitivity method of assaying the activity of γ-secretase that includes the steps of:
a) providing a container holding a composition suspected of containing γ-secretase activity;
b) adding to the container a polypeptide substrate for γ-secretase comprising at least a portion of an isoform of an APP polypeptide bound to a detectable label, wherein cleavage of the labeled substrate by γ-secretase provides a detectably labeled product;
c) contacting the labeled product with
   1) a first ligand bearing a first tag wherein the first ligand specifically binds the label, and
   2) a second ligand bearing a second tag wherein the second ligand specifically binds the product; and
d) determining the presence and/or the amount of the labeled product bound to the first ligand and to the second ligand.
In certain embodiments of the method the APP polypeptide is APP695 (SEQ ID NO:1), APP751 (SEQ ID NO:2), or APP770 (SEQ ID NO:3). In additional embodiments of the assay the portion contains amino acid residues 620-695 of APP695. In still further embodiments the label comprises biotin. In additional embodiments the first ligand includes an avidin and the first tag contains a detectable fluorescence acceptor, and in further embodiments the second ligand includes a first antibody that a) specifically binds a C-terminus of the product and that b) is bound to a second antibody bearing a fluorescence donor that excites the fluorescence acceptor tag bound to the first ligand.

An additional aspect the disclosure presents a high throughput method of assaying the activity of γ-secretase that includes the steps of:
a) providing a plurality of containers, each container containing a composition suspected of containing γ-secretase activity;
b) adding to each container a polypeptide substrate for γ-secretase comprising at least a portion of an isoform of an APP polypeptide bound to a detectable label, wherein cleavage of the labeled substrate by γ-secretase provides a detectably labeled product to each container;
c) contacting the labeled product with
   1) a first ligand bearing a first tag wherein the first ligand specifically binds the label, and
   2) a second ligand bearing a second tag wherein the second ligand specifically binds the product; and
d) determining the presence and/or the amount of the labeled product bound to the first ligand and to the second ligand.
In various embodiments of this method each container is a well in a multi-well assay plate. In various additional embodiments, a plate contains at least 96 wells, or at least 384 wells, or at least 1536 wells. In certain embodiments of the method the APP isoform is APP695 (SEQ ID NO:1), APP751 (SEQ ID NO:2), or APP770 (SEQ ID NO:3). In additional embodiments of the assay the portion contains amino acid residues 620-695 of APP695. In still further embodiments the label comprises biotin. In additional embodiments the first ligand includes an avidin and the first tag contains a detectable fluorescence acceptor, and in further embodiments the second ligand includes a first antibody that specifically binds a C-terminus of the product and a second antibody bearing a fluorescence donor that excites the fluorescence acceptor tag bound to the first ligand.

In an additional aspect a method is disclosed of assaying the activity of γ-secretase in a cell that includes the steps of:
a) providing a cell suspected of containing γ-secretase activity;
b) adding media comprising a polypeptide substrate for γ-secretase comprising at least a portion of an isoform of an APP polypeptide bearing a detectable label bound thereto, wherein cleavage of the labeled substrate by γ-secretase provides a labeled product;
c) separating the cells after a suitable incubation period to provide a supernatant; and
d) assaying the supernatant for the labeled product.
In this method the media may further include a detergent. Additionally, in many embodiments the label comprises biotin. In still other embodiments assaying for the labeled product comprises assaying for a detectable complex containing the product and one or more detectable probes, for example the complex includes a first specific binding member that contains a first detectable probe, wherein the first specific binding member specifically binds the product to form a binary complex. In specific embodiments the first probe comprises ruthenium such that the detection is conducted using electrochemiluminescence. In additional embodiments of the assaying further includes d) contacting the labeled product with
   1) a first ligand bearing a first tag wherein the first ligand specifically binds the label, and
   2) a second ligand bearing a second tag wherein the second ligand specifically binds the product; and
e) determining the presence and/or the amount of the labeled product bound to the first ligand and to the second ligand.

In the latter embodiments, the first ligand may include an avidin and the first tag contains a detectable fluorescence acceptor, and in addition the second ligand may include a first antibody that specifically binds a C-terminus of the product, wherein the first antibody is bound to a second antibody bearing a fluorescence donor that excites the fluorescence acceptor tag bound to the first ligand.

In an additional aspect this disclosure presents a high throughput method of assaying the activity of γ-secretase in a cell including the steps of:
a) providing a plurality of containers, each container including a cell suspected of containing γ-secretase activity;
b) adding media comprising a polypeptide substrate for γ-secretase comprising at least a portion of an isoform of an APP polypeptide bearing a detectable label bound thereto, wherein cleavage of the labeled substrate by γ-secretase provides a labeled product;
c) separating the cells after a suitable incubation period to provide a supernatant; and
d) assaying the soluble fraction of the supernatant for the labeled product.

In various embodiments each container is a well in a multi-well assay plate; and in particular further embodiments a plate comprises at least 96 wells, or at least 384 wells, or at least 1536 wells.

In an additional aspect this disclosure presents a method of screening for an inhibitor of γ-secretase activity including the steps of:
a) providing a container comprising a composition comprising γ-secretase activity;
b) contacting the composition with a mixture comprising a candidate compound and a polypeptide substrate for γ-secretase comprising at least a portion of an isoform of an APP polypeptide and a detectable label bound thereto, wherein cleavage of the labeled substrate by γ-secretase provides a labeled product that is detectable; and
c) determining whether the candidate compound inhibits formation of the labeled product of the γ-secretase-catalyzed cleavage of the substrate.

In certain embodiments of this screening method the substrate contains at least a portion of an APP isoform polypeptide; in additional embodiments the APP isoform is APP695 (SEQ ID NO:1), APP751 (SEQ ID NO:2), or APP770 (SEQ ID NO:3); and in a particular embodiment the portion of an APP isoform includes amino acid residues 620-695 of APP 695. In many embodiments of the method the label includes biotin. In other embodiments the assaying for the labeled product includes assaying for a detectable complex comprising the product and one or more detectable probes. In certain embodiments the complex contains a first specific binding member that includes a first detectable probe, wherein the first specific binding member specifically binds the product to form a binary complex, and in certain embodiments the first probe includes ruthenium such that the detection is conducted using electrochemiluminescence.

In additional embodiments of the method the determining further includes
d) contacting the labeled product with
   1) a first ligand bearing a first tag wherein the first ligand specifically binds the label, and
   2) a second ligand bearing a second tag wherein the second ligand specifically binds the product; and
e) determining the presence and/or the amount of the labeled product bound to the first ligand and to the second ligand.

In certain embodiments of this variation the first ligand includes an avidin and the first tag contains a detectable fluorescence acceptor. In further embodiments the second ligand includes a first antibody that specifically binds a C-terminus of the product bound to a second antibody bearing a fluorescence donor that excites the fluorescence acceptor tag bound to the first ligand.

In an additional aspect the disclosure provides a high throughput method of screening for an inhibitor of γ-secretase activity including the steps of:
a) providing a plurality of containers, each container containing a composition containing γ-secretase activity;
b) adding a composition comprising a candidate compound and a polypeptide substrate for γ-secretase comprising at least a portion of an isoform of an APP polypeptide and a detectable label bound thereto, wherein cleavage of the labeled substrate by γ-secretase provides a labeled product that is detectable with high sensitivity; and
c) determining whether the candidate compound inhibits formation of the labeled product of the γ-secretase-catalyzed cleavage of the substrate.

In various embodiments of this screening method each container is a well in a multi-well assay plate; and in particular embodiments of the screen a plate contains at least 96 wells, or at least 384 wells or at least 1536 wells.

Still a further aspect presented in this disclosure is a method of screening for an inhibitor of γ-secretase activity in a cell including the steps of:
a) providing a container that contains a cell comprising γ-secretase activity;
b) adding to the container media containing a candidate compound and a polypeptide substrate for γ-secretase comprising at least a portion of an isoform of an APP polypeptide and a detectable label bound thereto, wherein cleavage of the labeled substrate by γ-secretase provides a labeled product that is detectable with high sensitivity;
c) centrifuging the cells after a suitable incubation period to provide a supernatant; and
d) assaying the supernatant to determine whether the candidate compound inhibits formation of the labeled product.

In certain embodiments of this screening method the media further includes a detergent. In various additional embodiments the substrate includes at least a portion of an APP isoform polypeptide; in certain additional embodiments the APP isoform is APP695 (SEQ ID NO:1), APP751 (SEQ ID NO:2), or APP770 (SEQ ID NO:3); and in particular embodiments the portion of the APP isoform includes amino acid residues 620-695 of APP 695. In many embodiments of the method the label includes biotin. In other embodiments the assaying for the labeled product includes assaying for a detectable complex comprising the product and one or more detectable probes. In certain embodiments the complex contains a first specific binding member that includes a first detectable probe, wherein the first specific binding member specifically binds the product to form a binary complex, and in certain embodiments the first probe includes ruthenium such that the detection is conducted using electrochemiluminescence.

In additional embodiments of the method the determining further includes
   e) contacting the labeled product with
      1) a first ligand bearing a first tag wherein the first ligand specifically binds the label, and
      2) a second ligand bearing a second tag wherein the second ligand specifically binds the product; and
   f) determining the presence and/or the amount of the labeled product bound to the first ligand and to the second ligand.

In certain embodiments of this variation the first ligand includes an avidin and the first tag contains a detectable fluorescence acceptor. In further embodiments the second ligand includes a first antibody that specifically binds a C-terminus of the product bound to a second antibody bearing a fluorescence donor that excites the fluorescence acceptor tag bound to the first ligand.

In still an additional aspect the disclosure presents a high throughput method of screening for an inhibitor of γ-secretase activity in a cell that includes the steps of:
   a) providing a plurality of containers, each container containing a cell containing γ-secretase activity;
   b) to each container adding media comprising a candidate compound and a polypeptide substrate for γ-secretase comprising at least a portion of an isoform of an APP polypeptide and a detectable label bound thereto, wherein cleavage of the labeled substrate by γ-secretase provides a labeled product that is detectable with high sensitivity; and
   c) determining in each container whether the candidate compound inhibits formation of the labeled product of the γ-secretase-catalyzed cleavage of the substrate.

In various embodiments of this screening method each container is a well in a multi-well assay plate; in certain embodiments a plate contains at least 96 wells, or at least 384 wells, or at least 1536 wells.

In an additional aspect, this disclosure presents a polypeptide that includes at least a portion of a modified Aβ sequence, in which at least one of the amino acid residues corresponding to residues 17-21 of Aβ (SEQ ID NO:19) is modified. This polypeptide is constructed to serve as a substrate for γ-secretase activity. In many embodiments this polypeptide is an enhanced substrate for γ-secretase activity. In certain embodiments the polypeptide is at least 28 amino acid residues in length. In other embodiments at least one of the amino acid residues corresponding to amino acid residues 17-21 of Aβ is deleted. In still additional embodiments at least one of the amino acid residues corresponding to amino acid residues 17-21 of Aβ is substituted by another residue. In various embodiments the polypeptide is selected from the group consisting of S1 substrate (SEQ ID NO:9) of Table 2, S4 substrate (SEQ ID NO:12) of Table 2, S5 substrate (SEQ ID NO:13) of Table 2, S6 substrate (SEQ ID NO:14) of Table 2, β-CTFΔ substrate (SEQ ID NO:25), a modified APP695 substrate, the C100F19A substrate (mutated SEQ ID NO:28), the C100F20A substrate (mutated SEQ ID NO:28), and the C100F19AF20A substrate (mutated SEQ ID NO:28). In many embodiments, any of these substrate polypeptides includes a detectable label.

In a further aspect this disclosure presents a polynucleotide that contains a nucleotide sequence encoding a substrate polypeptide described in the preceding paragraph. Thus, in certain embodiments of a polynucleotide the sequence encodes a polypeptide in which the amino acid residues corresponding to residues 17-21 of Aβ are deleted; or in which at least the amino acid residues corresponding to residues 17-21 of Aβ are substituted by another amino acid residue. In additional embodiments the polynucleotide sequence encodes a polypeptide selected from the group consisting of the S1 substrate (SEQ ID NO:9) of Table 2, S4 substrate (SEQ ID NO:12) of Table 2, S5 substrate (SEQ ID NO:13) of Table 2, S6 substrate (SEQ ID NO:14) of Table 2, β-CTFΔ substrate (SEQ ID NO:25), a modified APP695 substrate, the C100F19A substrate (mutated SEQ ID NO:28), the C100F20A substrate (mutated SEQ ID NO:28), and the C100F19AF20A substrate (mutated SEQ ID NO:28). In still additional embodiments the polynucleotide encodes a labeled polypeptide wherein the label includes an amino acid sequence that can be modified to include a detectable moiety In a further aspect an expression vector is disclosed that includes the polynucleotide described in the preceding paragraph operably linked with a promoter that promotes expression of the polynucleotide. In an embodiment of the expression vector the polynucleotide encodes a polypeptide in which amino acid residues corresponding to residues 17-21 of Aβ are deleted or substituted. In other embodiments of the expression vector the polynucleotide encodes a polypeptide selected from the group consisting of the S1 substrate (SEQ ID NO:9) of Table 2, S4 substrate (SEQ ID NO:12) of Table 2, S5 substrate (SEQ ID NO:13) of Table 2, S6 substrate (SEQ ID NO:14) of Table 2, β-CTFΔ substrate (SEQ ID NO:25), a modified APP695 substrate, the C100F19A substrate (mutated SEQ ID NO:28), the C100F20A substrate (mutated SEQ ID NO:28), and the C100F19AF20A substrate (mutated SEQ ID NO:28).

In an additional aspect a cultured cell is disclosed that contains an expression vector described in the preceding paragraph.

In yet a further aspect this disclosure presents a method of expressing a polypeptide, including:
   a) transfecting a cell with a vector described two paragraphs above; and
   b) culturing the transfected cell under conditions suitable to express the polypeptide.

In still a further aspect this disclosure presents a method of synthesizing a polypeptide, comprising:
   a) identifying the sequence of a polypeptide comprising at least a portion of a modified Aβ sequence, wherein the amino acid residues corresponding to residues 17-21 of Aβ are modified; and
   b) chemically synthesizing a polypeptide having the identified sequence.

In an additional aspect a polypeptide is disclosed that includes amino acid residues 17-21 of Aβ such that the polypeptide is ten amino acid residues or less in length. This polypeptide inhibits the activity of γ-secretase. In various embodiments this polypeptide is 7 amino acid residues or less in length In still another aspect of this disclosure a method of inhibiting the activity of γ-secretase is disclosed that includes contacting a system that contains a composition having γ-secretase activity with a polypeptide that includes amino acid residues 17-21 of Aβ, the polypeptide being 10 amino acid residues in length or less; or in other embodiments, the polypeptide is 7 amino acid residues or less in length. In certain further embodiments of this method the substrate contains an APP or a fragment thereof or labeled derivative of any of them that is cleavable by γ-secretase. In alternative embodiments of this method the substrate includes a Notch polypeptide or a fragment thereof or labeled derivative of any of them that is cleavable by γ-secretase.

In still an additional aspect this disclosure presents a method of inhibiting the activity of γ-secretase that includes contacting a system containing a composition having γ-secretase activity with a ligand that forms a specific binding pair with a LVFFAE (amino acids 1-6 of SEQ ID NO:18) amino acid sequence of a γ-secretase substrate. In an embodiment of this method, the ligand includes an antibody that binds a LVFFAE amino acid sequence (amino acids 1-6 of SEQ ID NO:18). In a further embodiment the substrate contains an APP or a fragment thereof or a labeled derivative of any of them that is cleavable by γ-secretase. In an alternative embodiment the substrate contains a Notch polypeptide or a fragment thereof or a labeled derivative of any of them that is cleavable by γ-secretase.

In another aspect of the disclosure, a method of inhibiting the formation of an Aβ polypeptide in a cell is disclosed, in which the method includes promoting the activity of TACE (Tumor necrosis factor-α converting enzyme) or α-secretase in the cell.

An additional aspect of this disclosure presents a polypeptide substrate for γ-secretase that includes at least a portion of an isoform of an APP polypeptide and a detectable label bound thereto, in which cleavage of the labeled substrate by γ-secretase provides a labeled product that is detectable with high sensitivity. In certain embodiments of the polypeptide the APP isoform is APP695 (SEQ ID NO:1), APP751 (SEQ ID NO:2), or APP770 (SEQ ID NO:3). In particular embodiments the portion of the APP isoform contains amino acid residues 620-695 of APP695. In certain additional embodiments of the polypeptide the label contains a detectable peptide sequence bearing, or reactible to bear, a tag.

In yet a further aspect this disclosure presents a detectable complex that includes the detectable labeled product produced when γ-secretase cleaves the polypeptide described in the preceding paragraph and one or more detectable probes. In various embodiments the complex contains at least a first specific binding member that comprises a first detectable probe, wherein the first specific binding member specifically binds the γ-secretase cleavage product to form a binary complex. In certain additional embodiments, a complex containing a first specific binding member bearing its first detectable probe, further contains a second specific binding member that includes a second detectable probe. In yet a further embodiment a complex is detectable only when the complex comprises both the first detectable probe and the second detectable probe.

In still a further aspect this disclosure presents a polypeptide that includes a retro-inverso Aβ (17-23) sequence, such as SEQ ID NO:24. A retro-inverso polypeptide is composed of D-amino acids assembled in the reverse order from the reference peptide containing naturally-occurring L-amino acids, and possesses similar topographies as the original L-peptide, yet is more resistant to proteolysis.

In still an additional aspect, a method of inhibiting γ-secretase activity in a cell is disclosed, wherein the method includes contacting the cell with a polypeptide that includes a retro-inverso Aβ (17-23) sequence such as SEQ ID NO:24

4. DESCRIPTION OF THE DRAWINGS

FIG. 1. The proteolysis of APP by α-, β- and γ-secretases. Two pathways (β/γ and α/γ) of APP processing have been established. APP can be cleaved by either β- or α-secretase, and is then followed by γ-secretase cleavage. γ-Secretase is incapable of processing APP without β- or α-secretase cleavage that removes the large fragments of the extracellular domain. The designation of substrates and products are depicted.

Figure 2:
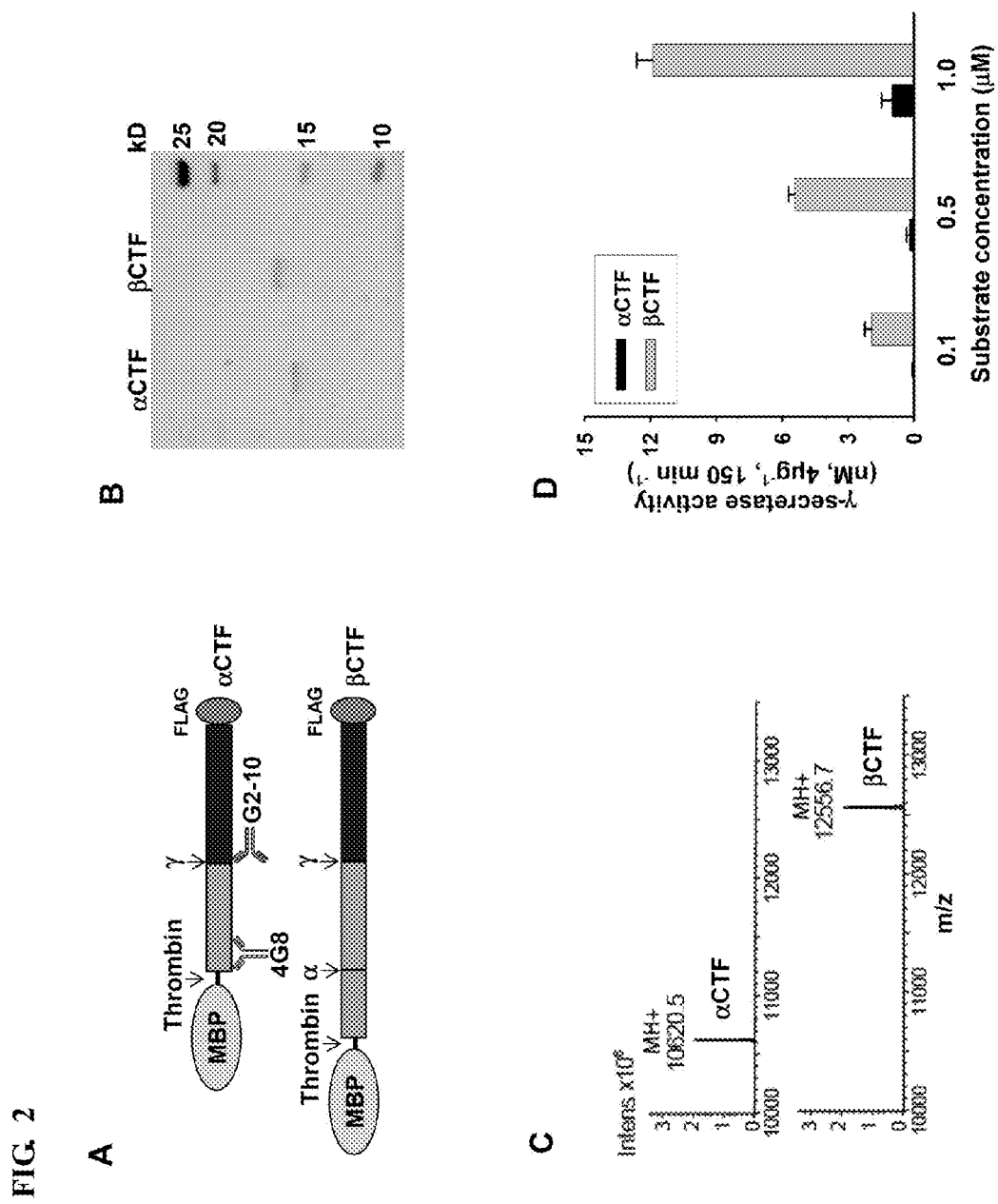

FIG. 2. In vitro γ-secretase activity for proteolysis of αCTF (SEQ ID NO:7) and βCTF (SEQ ID NO:8). (A) Schematic representation of MBP-βCTF and MBP-αCTF synthetic substrates. The N- and C-termini of αCTF and βCTF are tagged with maltose binding protein (MBP) and FLAG, respectively. There is a thrombin cleavage site between MBP and the APP polypeptides. The cleavage sites of thrombin, α- and γ-secretase are indicated by arrows. The recognition epitope of antibodies that have been used in the assay of FIG. 2D are indicated by the "Y"-shaped cartoon symbols. (B) and (C) Analyses of αCTF and βCTF. Purified proteins were separated by SDS-PAGE and stained by Coomassie Blue (Panel B). The protein masses were determined by Electrospray LC-MS (Panel C). The molecular mass of αCTF and βCTF were calculated through deconvolution of mass-to-charge ratio (m/z). (D) In-vitro γ-secretase activity for production of X40 (the product resulting from γ-secretase cleavage of βCTF between the positions corresponding to Aβ40 and Aβ41; see FIG. 1) from αCTF and βCTF substrates. Each substrate at 0.1, 0.5 and 1 μM was incubated with HeLa membrane (4 μg) in the presence of 0.25% CHAPSO. After 2.5 hrs incubation, the reaction was stopped by adding RIPA buffer and the product X40 was assayed with biotinylated 4G8 and ruthenylated G2-10 antibodies by ECL (mean±SEM; n>3). The amount of X40 was determined using synthetic Aβ40 and P3 (see FIG. 1) peptides as standards. Note: in all figures, the assay background was defined in the presence of 1 μM or 2 μM L-685,458 for in vitro and cell based assays, respectively. γ-Secretase activity was calculated by subtracting the assay background from the signal that was detected in the absence of inhibitor (DMSO only).

Figure 3:
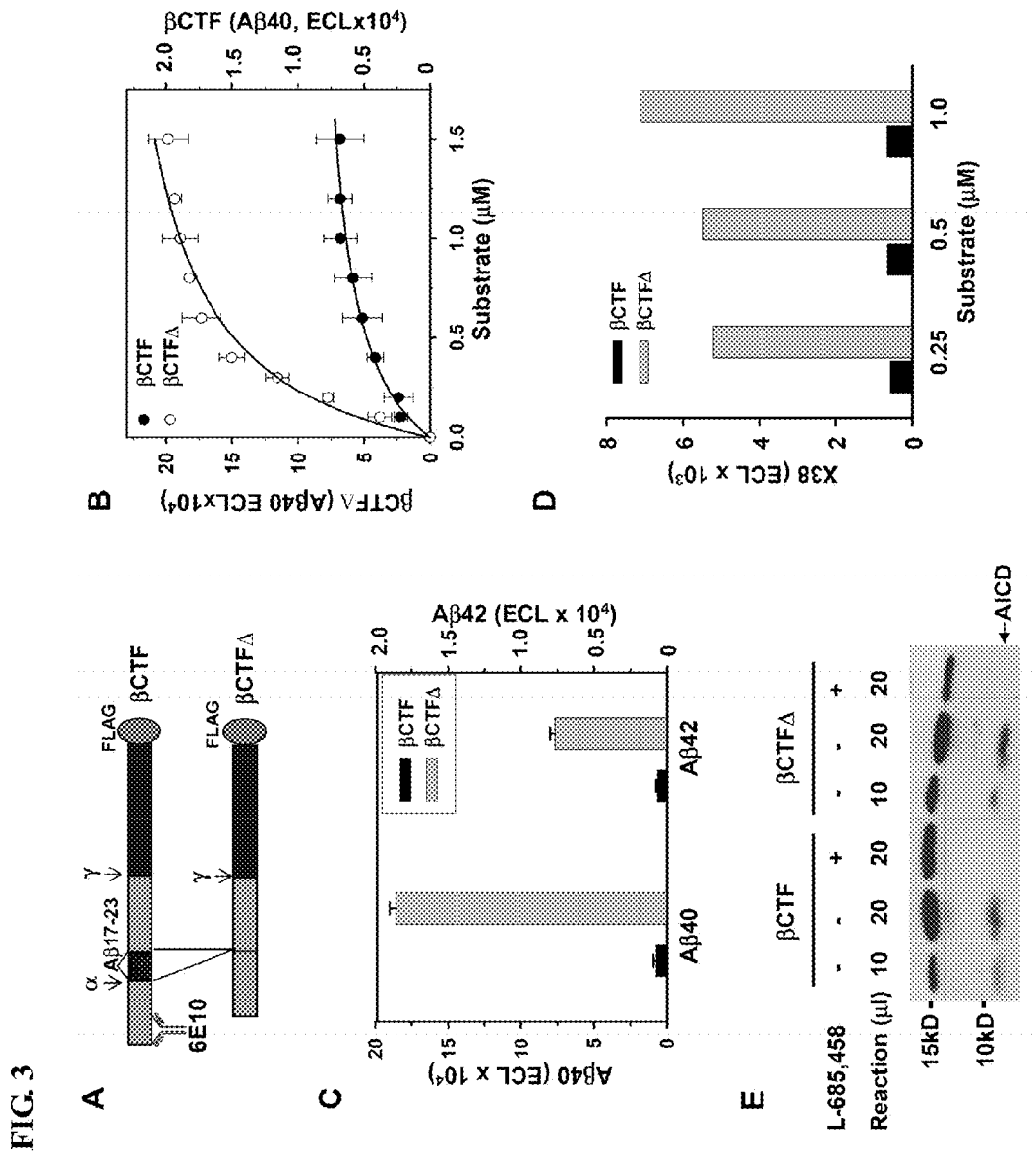

FIG. 3. Effect of the inhibitory domain on in vitro γ-secretase activity. (A) Schematic representation of βCTF (SEQ ID NO:8) and the Aβ17-23 deleted form of βCTF (βCTFΔ; SEQ ID NO:25). The γ-secretase cleavage site is indicated by an arrow between orange and blue shades. The Aβ17-23 region is marked by dotted square. (B) The kinetic analyses of γ-secretase reactivity with βCTF and βCTFΔ substrates. Various concentrations of substrate (βCTF or βCTFΔ) were incubated with HeLa membrane in the presence of 0.25% CHAPSO. The product Aβ40 was assayed with biotinylated 6E10 and ruthenylated G2-10 antibodies by ECL. The Km and Vmax were calculated using the Michaelis-Menten equation (mean±SEM; n>3). Note: There is a 10-fold difference between left Y-axis that is for the βCTFΔ substrate and right Y-axis for the βCTF substrate. (C) In vitro γ-secretase activity from mouse brain using βCTF and βCTFΔ substrates. βCTF or βCTFΔ was incubated with mouse brain membrane, and Aβ40 (SEQ ID NO:16) and Aβ42 (SEQ ID NO:17) were detected by biotinylated 6E10 paired with ruthenylated G2-10 or G2-11 antibodies, respectively (mean±SEM; n>3). Note: There is a 10-fold difference between left Y-axis that is for Aβ40 and right Y-axis for Aβ42. (D) The effect of an inhibitory domain on γ-secretase activity for Aβ38 production. βCTF or βCTFΔ at 0.25, 0.5 and 1 μM was incubated with HeLa membrane in the presence of 0.25% CHAPSO. The product Aβ38 was assayed with biotinylated 6E10 and ruthenylated Aβ38 antibodies (purchased from Dr. Pankaj D. Methta) (data represent the mean of duplicates with variance<10%). (E) The effect of an inhibitory domain on γ-secretase activity for ACID production. HEK293 cell membrane was prepared from cells that have been transfected with βCTF (SPA4CT) (Lichtenthaler et al., 1999) and βCTFΔ (SPA4CTΔ) constructs for 48 hours. Cell membranes (2 mg/ml) were incubated in the absence and presence of 2 μM L-685,458 and then analyzed by Western blotting with CT-15 antibody (Chen et al., 2002).

Figure 4:
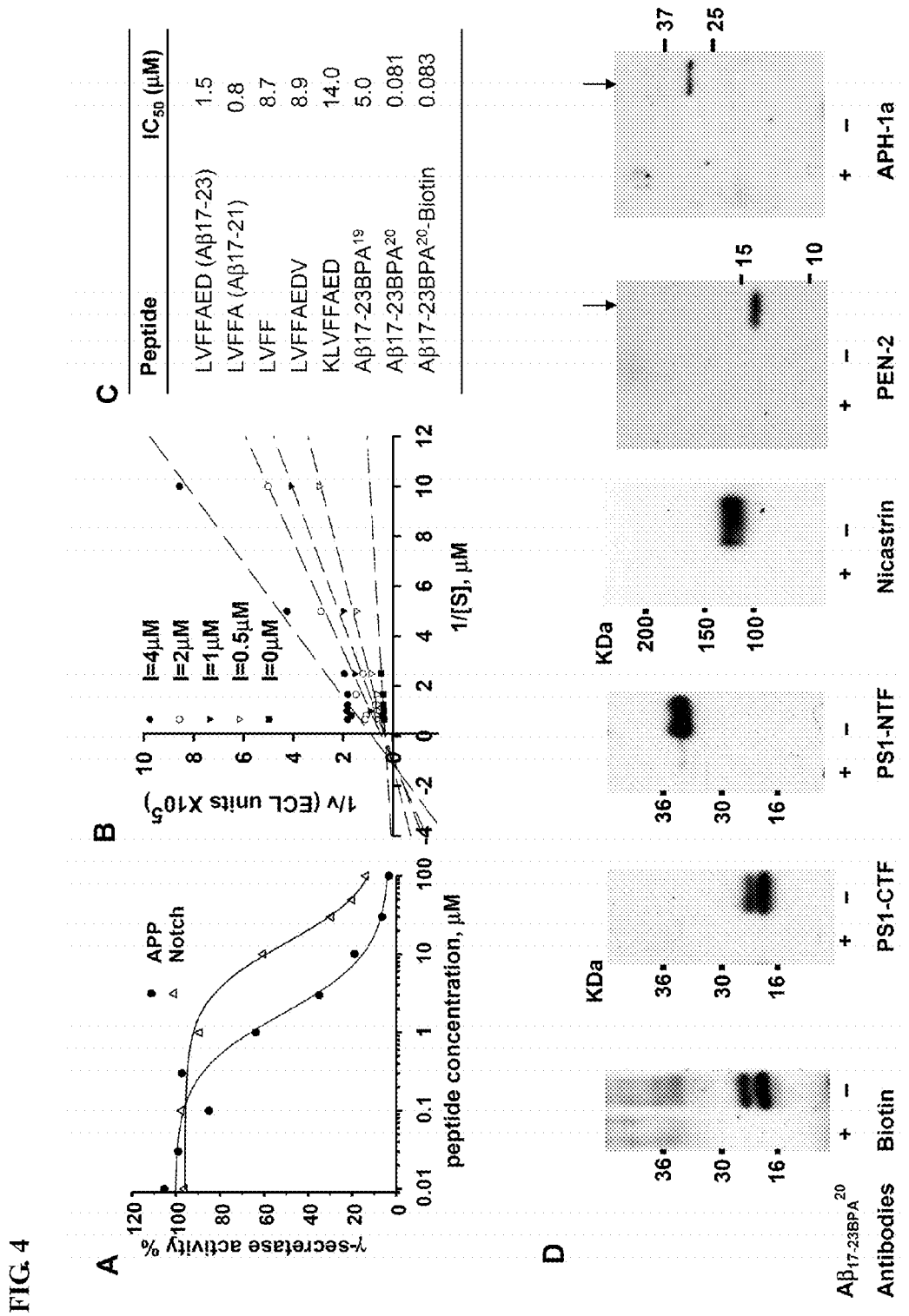
Figure 4:
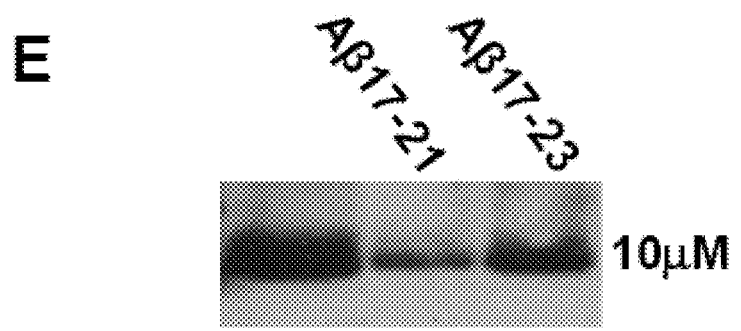
Figure 4:
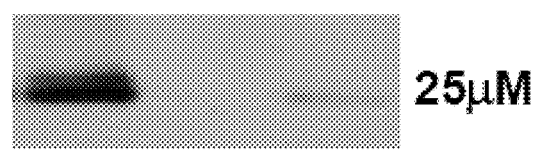
Figure 4:
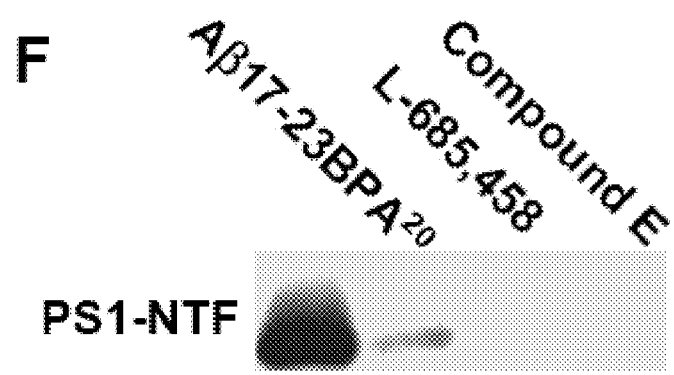
Figure 4:

FIG. 4. Covalent labeling of γ-secretase subunits by an Aβ17-23 derived photoreactive γ-secretase inhibitor. (A) Inhibition of in vitro γ-secretase activity for APP and Notch substrates by Aβ17-23 (LVFFAED) peptide (SEQ ID NO:18). Various concentrations of inhibitor were incubated with APP substrate (S4) or Notch peptide substrate containing the C-terminal biotinylated transmembrane domain of Notch1 and HeLa cell membrane in the presence of 0.25% CHAPSO. Aβ40 was detected by G2-10 antibody. The cleaved Notch product was detected by Val1744 antibody that specifically recognizes the cleaved product between Gly1743 and Val1744. Activities are expressed as percentage relative to reading that was produced in DMSO control. (B) Lineweaver-Burk plots for inhibition of γ-secretase by Aβ17-23 peptide. Various concentrations of S4 substrate were incubated with HeLa membrane in fixed concentrations of inhibitor as indicated. The double reciprocal velocity (1/v) and substrate concentrations (1/S) are plotted to determine the type of inhibition. (C) Inhibitory potencies of Aβ17-23 and its analogs. Assays were conducted as described in FIG. 4A. (D) Photoaffinity labeling of γ-secretase by biotinylated photoreactive peptide Aβ17-23(Aβ17-23BPA$_{20}$-biotin). Aβ17-23BPA$_{20}$-biotin (300 nM) was photoactivated with HeLa cell membrane with 0.25% CHAPSO in the absence or presence of Aβ17-23BPA$_{20}$ (10 μM). The labeled samples were solubilized with RIPA buffer. Biotinylated proteins were captured with streptavidin-agarose and probed by immunoblotting using antibodies against biotin, PS1-CTF, PS1-NTF, Nicastrin, PEN-2 and APH-1a. HeLa cell membrane proteins were directly loaded onto lanes indicated by an arrow in the PEN-2 and APH-1a blots as positive controls. (E) Effect of Aβ17-21 and Aβ17-23 on the photoinsertion of Aβ17-23BPA$_{20}$-Biotin. Photoactive peptide Aβ17-23BPA$_{20}$-Biotin was used at 300 nM in the absence or the presence of Aβ17-21 and Aβ17-23 peptides (SEQ ID NOS:19 and 18, respectively) at 10 μM (upper panel) and 25 μM (lower panel), respectively. (F) Effect of γ-secretase inhibitors (L-685,458 and compound E) on the photoinsertion of Aβ17-23BPA$_{20}$-Biotin into the subunits of γ-secretase. Upper panel: PS1-NTF; Lower panel: PS1-CTF. Photoactive peptide Aβ17-23BPA$_{20}$-Biotin at 300 nM and Aβ17-23BPA$_{20}$ at 10 μM, L-685,458 at 2 μM compound E at 2 μM were used for this study.

Figure 5:
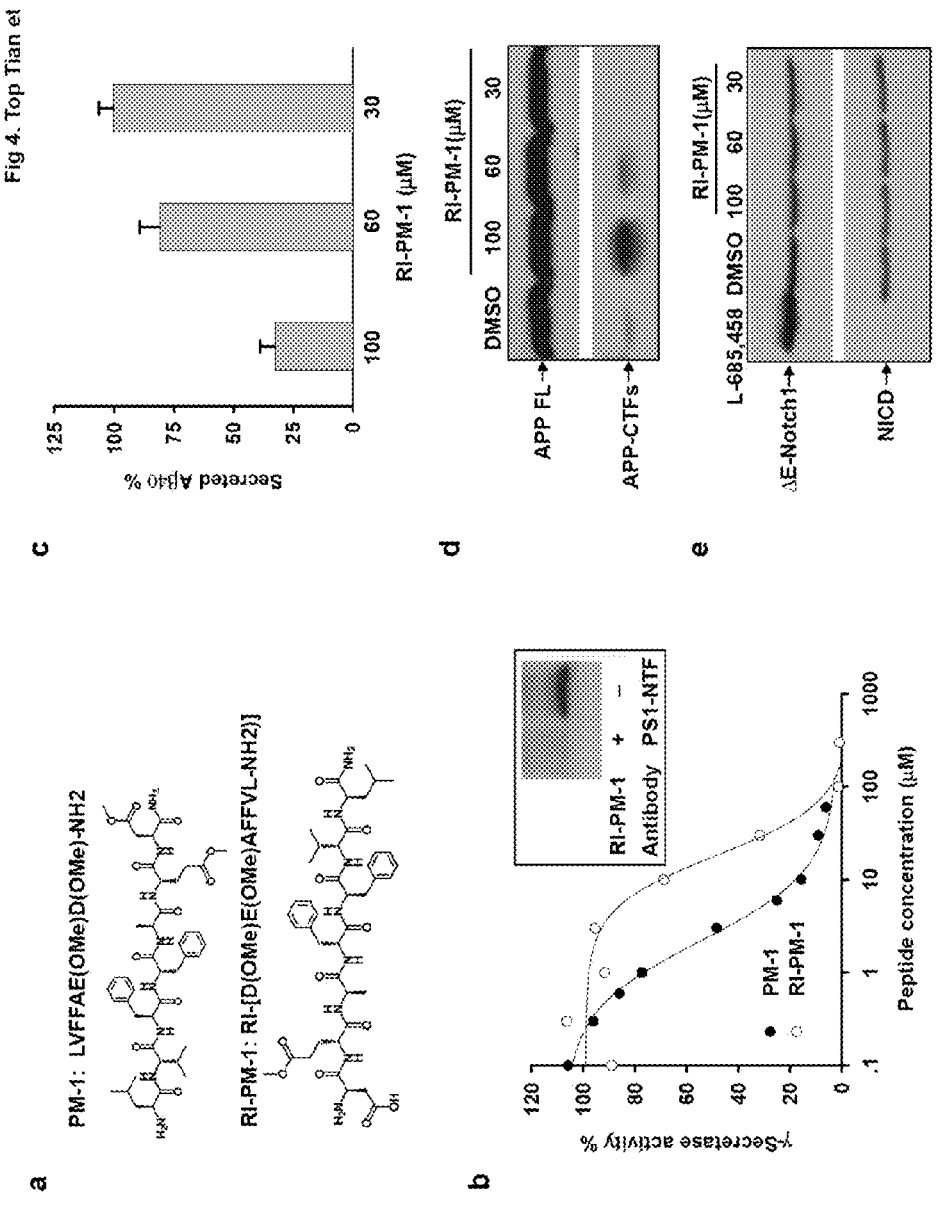

FIG. 5. Retro inverso peptide derivative of the inhibitory domain inhibits cellular γ-secretase activity for the processing of APP but not Notch1. (a) Structures of the modified inhibitory domain peptide (PM-1; SEQ ID NO:23) and its retro inverso version (RI-PM-1; (SEQ ID NO:24). In PM-1 the C-terminus of Aβ17-23 peptide is amidated and the side chains of the Glu(E) and Asp(D) amino acids are converted into methyl ester. RI-PM-1 is a retro-inverso form of PM-1 which reverses the primary sequence of PM-1 and changes the L-amino acids to D-amino acids. (b) Inhibitory potency and specificity of the RI-PM-1 peptide. The IC50 of the PM-1 and RI-PM-1 peptide were determined by assessing production of Aβ40 using by 6E10 or 4G8 and G2-10 antibodies. The inset showed that RI-PM-1 (100 μM) can block the photoinsertion of Aβ17-23BPA$_{20}$-biotin (300 nM) into PS1. (c) Effect of RI-PM-1 peptide on secreted Aβ40 production. RI-PM-1 at 100, 60 and 30 μM was used to treat N2A APP stable cells for 48 hrs. The conditioned media were collected and secreted Aβ40 was measured with 6E10/G2-10 antibodies (mean±SEM; n=3). The activities of the peptide treatments were normalized to the DMSO treatment. (d) Effect of RI-PM-1 on intracellular APP CTFs. The same experiments were performed as FIG. 5c. The cell lysates were analyzed by CT-15 antibody. Upper panel: full length APP. Lower panel: CTFs. (e) Effect of RI-PM-1 on Notch1 processing. The ΔE-Notch1 (a Notch construct with deletion of the extracellular portion and tagged by Myc) was transfected into HEK293 cells. After transfection, the cells were treated with DMSO, L-685,458 (2 μM) and RI-PM-1 (100, 60 and 30 μM) for 48 hrs. The cell lysates were analyzed by Western blot with anti-Myc (upper panel) and SM320 antibody (lower panel) that specifically recognizes the γ-secretase cleaved NICD, but not substrate.

Figure 6:
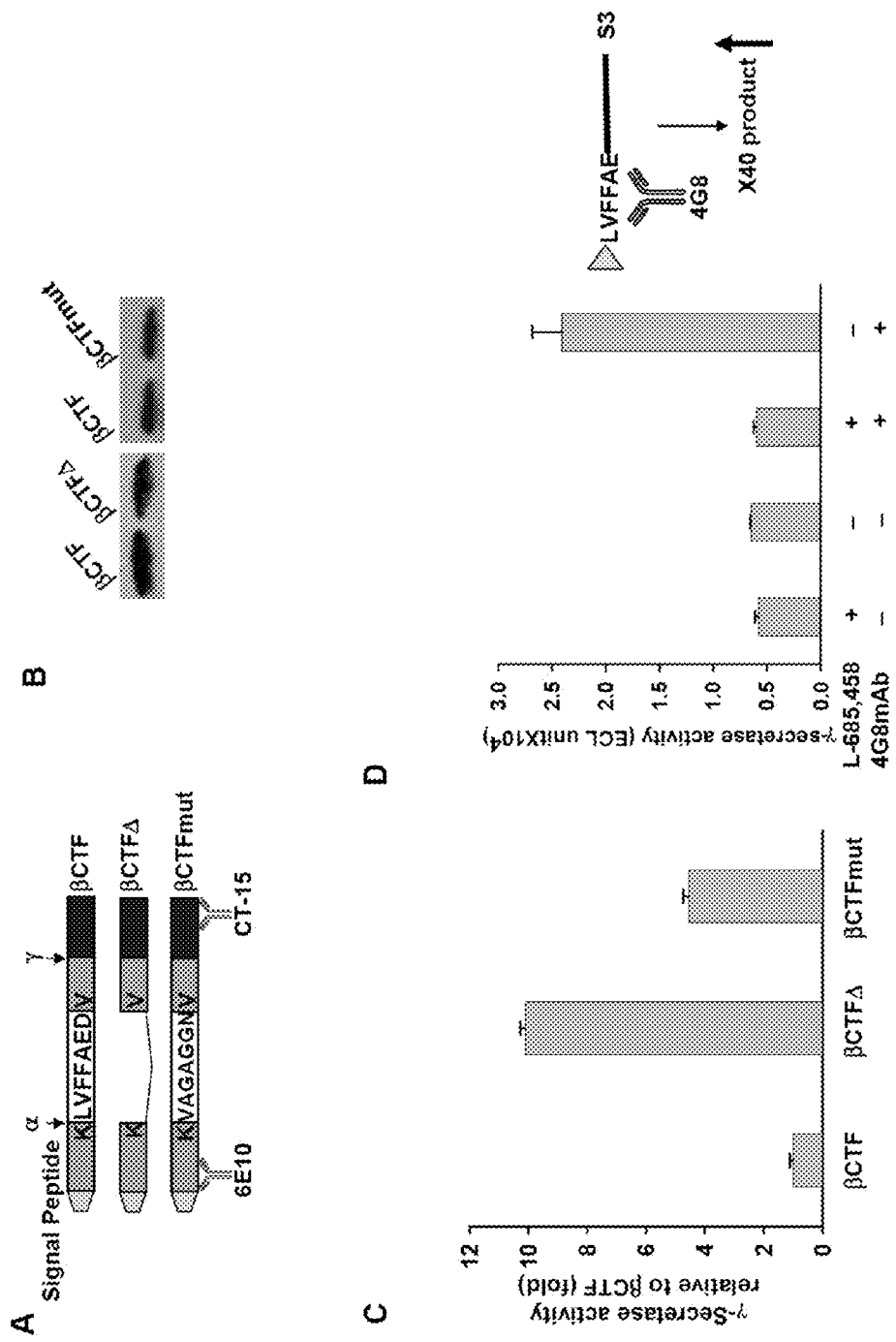

FIG. 6. Effect of the Aβ17-23 inhibitory domain on γ-secretase activity in cells (A) Schematic representation of the βCTF, βCTF deletion (βCTFΔ) and βCTF mutation (βCTFmut) proteins (SEQ ID NOS:8, 25 and 26, respectively) in the cellular studies. The cleavage sites of α- and γ-secretases are indicated by arrows. The light blue trapezoid indicates signal peptide. All three proteins are identical except for the Aβ17-23 sequence (LVFFAED, SEQ ID NO:18) as indicated; the LVFFAED heptapeptide (SEQ ID NO:18) is deleted in the βCTFΔ and mutated to the VAGAGGN (amino acids 17-23 of SEQ ID NO:26) in the βCTFmut constructs. The recognition epitope of antibodies that have been used in Panels B and C are indicated by the "Y"—shaped cartoon symbols. (B) The protein expression levels of βCTF, βCTFΔ and βCTFmut in HEK293 cells. HEK293 cells were transiently transfected with individual constructs in the presence and the absence of 2 μM L-685,458. After 24 hours, cells were lysed and analyzed by western blot using CT-15 antibody for the protein expression levels. Two western blots represent two independent experiments. (C) Effect of deletion and mutation of the inhibitory domain on Aβ and production. The conditioned media from the transfection of (B) was collected and secreted Aβ40 was measured with 6E10 and G2-10 antibodies (mean ±SEM; n>3). The Aβ production levels of βCTFΔ and βCTFmut are normalized to βCTF. (D) Effect of the S3 protein complexed with 4G8 antibody on γ-secretase activity in vitro. Monoclonal 4G8 antibody (4G8mAb) (100 ng/μl) was pre-incubated with S3 protein (1 μM) for 30 min. The biotinylated S3 with and without treatment of 4G8 was incubated with HeLa membrane in the presence of 0.25% CHAPSO. The X40 product was detected using streptavidin beads and G2-10 antibody (mean ±SEM n >3). The scheme on the right indicates the 4G8 antibody binding epitope on S3 protein.

Figure 7:
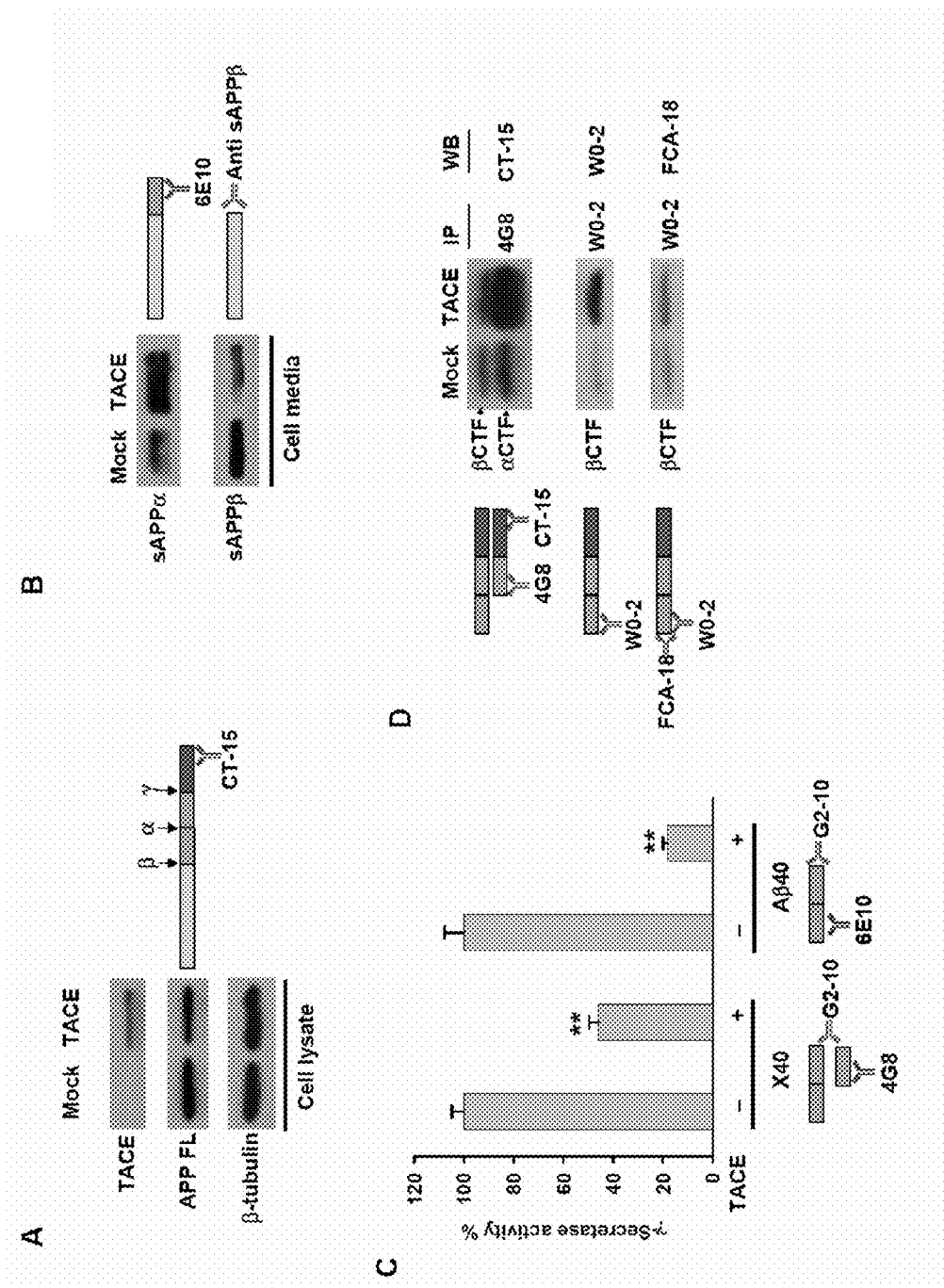
Figure 7:
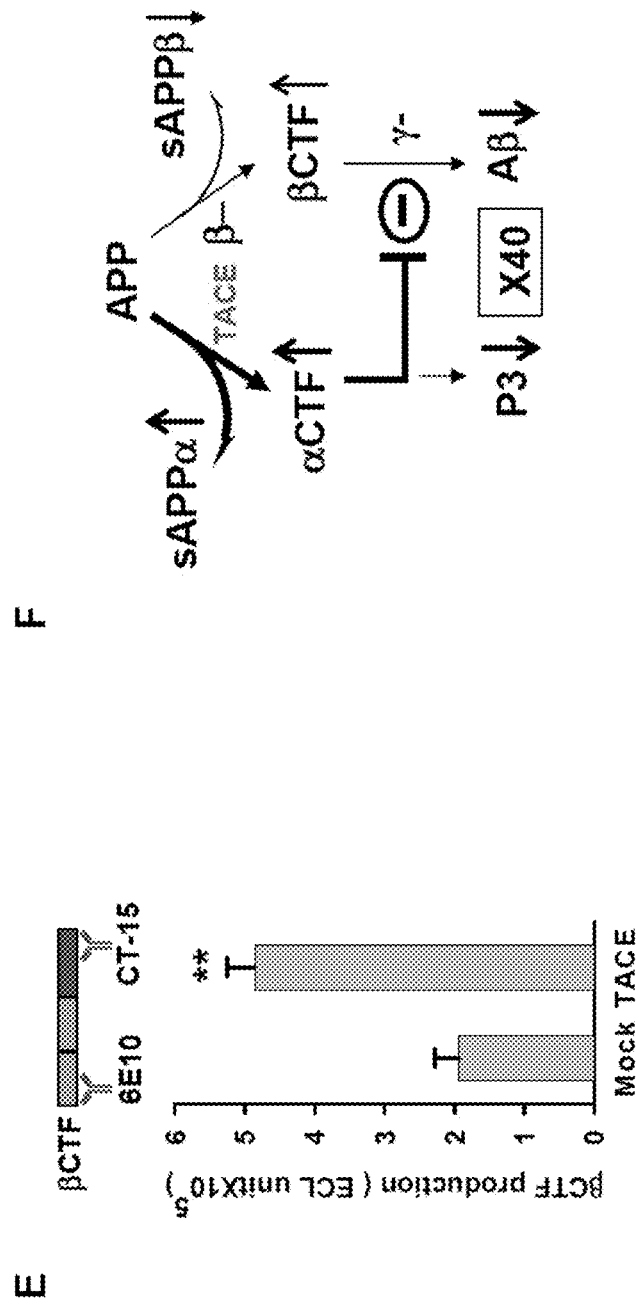

FIG. 7. α-Secretase cleaved CTF (αCTF; SEQ ID NO:7) negatively modulates γ-secretase activity in cells (A)-(E) Effect of TACE expression on APP695, sAPPα, sAPPβ, αCTF and βCTF (SEQ ID NOS:1, 4, 5, 7 and 8, respectively). After the HA tagged TACE gene has been transiently transfected into HEK293 cells that stably express APP (HEK293-APP) for 72 hours, both cell lysates (A, D and E) and conditioned media (B and C) were analyzed using ECL assay (C and E) or western blot (A, B and D) using indicated antibodies. Schematic representations of the APP fragments detected by corresponding antibodies are indicated beside each panel. (mean±SEM n>3)(** p<0.01). (F) Schematic summary of the effect of TACE expression on α-, β- and γ-secretase cleavages of APP. Overexpression of TACE enhances the production of sAPPα and αCTF and reduces the production of sAPPβ. αCTF negatively modulate γ-secretase activity that concurrently leads to an accumulation of βCTF and a reduction of Aβ and X40.

Figure 8:
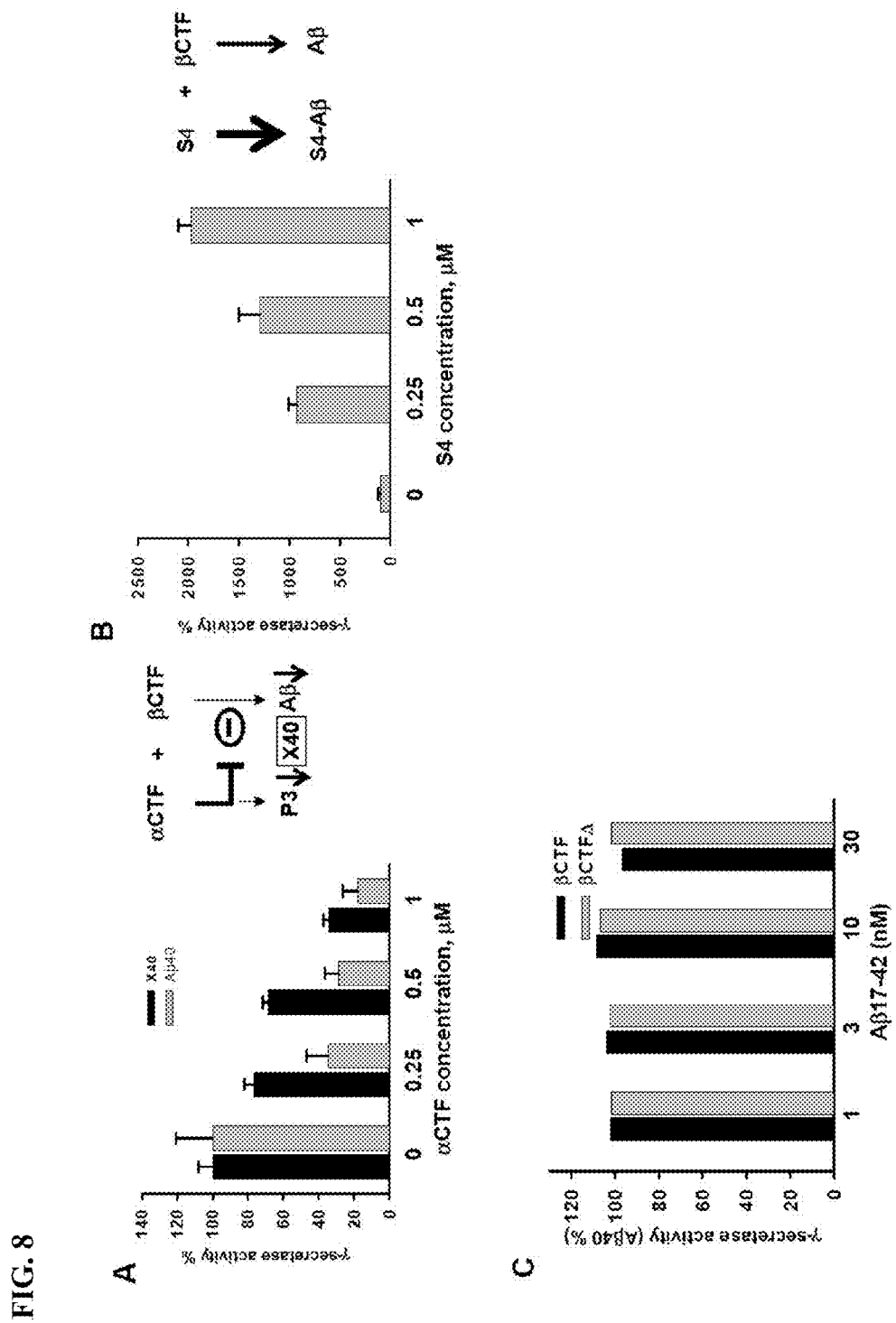

FIG. 8. α-Secretase cleaved CTF (αCTF) negatively modulates γ-secretase activity in vitro. (A) Effect of recombinant αCTF on in vitro γ-secretase activity. αCTF (0.25, 0.5 and 1 μM) were added to the in vitro γ-secretase reaction with 1 μM βCTF substrate in the presence of 0.25% CHAPSO. Detection of X40 and Aβ40 were performed as explained in FIG. 7C (mean±SEM n>3). As shown on the right, αCTF inhibits γ-secretase activity for the processing of βCTF. (B) Effect of recombinant S4 on in vitro γ-secretase activity. S4 protein, which lacks the inhibitory domain, was added at concentrations of 0.25, 0.5, and 1 μM to the in vitro γ-secretase reaction mixture in the presence of 1 μM βCTF as substrate. The 40-site product was detected by 6E10/G2-10 antibodies (mean±SEM n>3). As indicated by the scheme on the right, S4 does not suppress the processing of βCTF by γ-secretase and is a better substrate of γ-secretase as well. (C) Effect of Aβ17-42 on in vitro γ-secretase activity. Synthetic peptide Aβ17-42 at 1, 3, 10 and 30 nM were co-incubated with HeLa cell membrane and 1 μM of βCTF or βCTFΔ substrate in the presence of 0.25% CHAPSO. Aβ40 was detected by 6E10/G2-10 antibodies (Data represents the average of two experiments).

Figure 9:
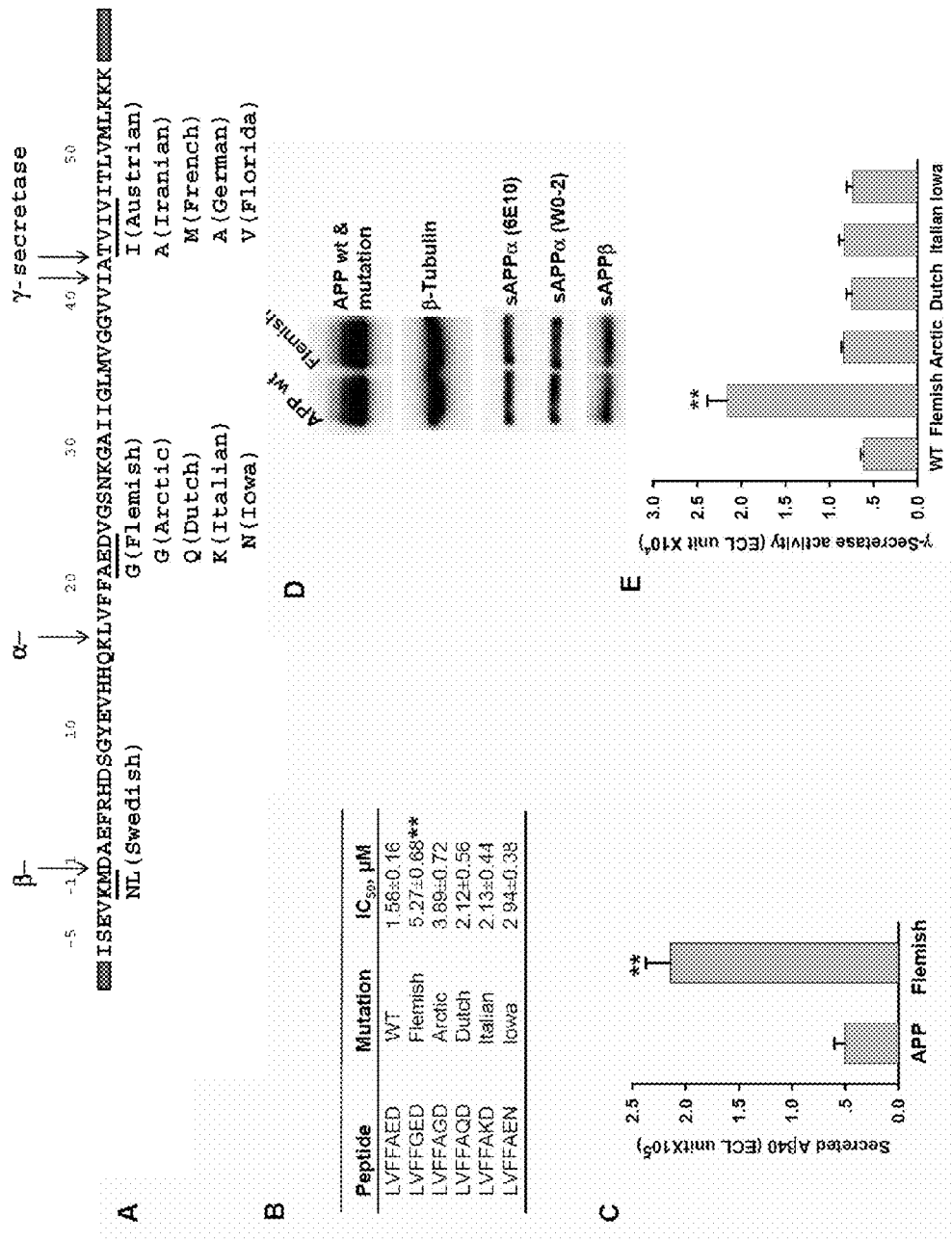

FIG. 9. Effect of internal Aβ FAD mutations on γ-secretase activity. (A) Five Alzheimer and Alzheimer-related disorder mutations are located in the Aβ17-23 sequence of APP. (B) Inhibitory potency of the five peptides that were synthesized based on FAD mutations. The IC50 values were determined as described in FIG. 6A. ( p<0.01; n=3). (C) Effect of the FAD mutations on secreted Aβ40. After 48 hours transfection, conditioned media from each mutant were analyzed for Aβ peptide production using 6E10 and G2-10 antibodies ( p<0.01; n>3). (D) The effect of Flemish mutation on the level of APP, sAPPα and sAPPβ. After APPwt or Flemish, were transiently transfected into HEK 293 cells for 48 hours, cell lysates and conditioned media were subjected to Western blot analysis with CT15 (upper panel), β-tubulin (middle upper panel), 6E10, W0-2 (middle lower panels) and anti-sAPPβ (lower panel) antibodies. (E) Effect of the internal Aβ FAD mutations on in vitro γ-secretase activity. Recombinant βCTFs derived from wild type and the FAD mutations were expressed in *E. coli* and purified using an MBP tag. Purified βCTF WT and mutations (1 μM) were incubated with HeLa membrane in the presence of 0.25% CHAPSO and the production of Aβ40 was detected by biotinylated 6E10 and ruthenylated G2-10 antibodies (6E10/G2-10) (** p<0.01; mean±SEM; n=3).

Figure 10:
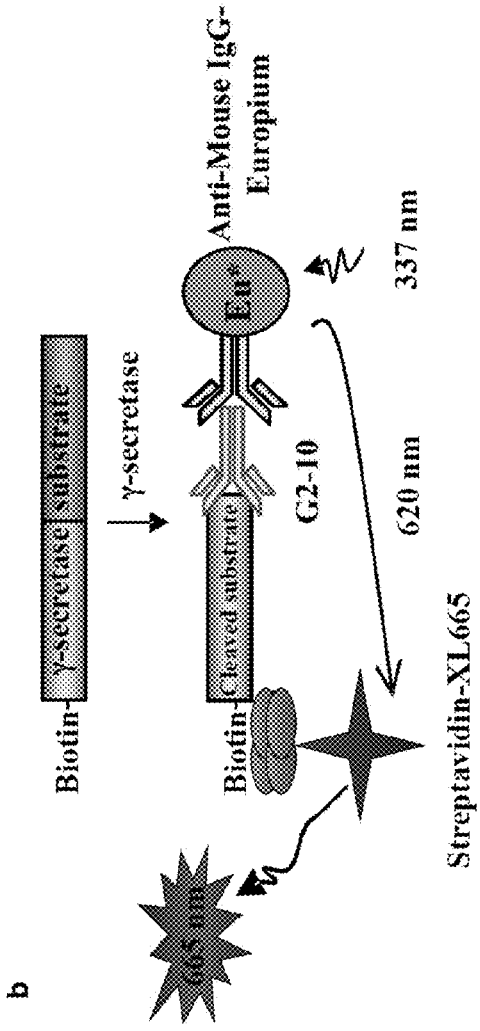

FIG. 10. Development of a homogeneous time-resolved fluorescence (HTRF) γ-secretase assay using a biotinylated recombinant substrate Sb4. (a) Comparison of the reactivity of Sb4 and C100Flag in a γ-secretase assay utilizing electrochemiluminescence detection. The C100Flag substrate is not biotinylated, and therefore requires an additional biotinylated antibody in the assay. High activity was defined in the presence of 1% DMSO (v/v), whereas low activity is the remaining γ-secretase activity in the presence of 100 nM Compound E GSI (γ-secretase inhibitor; delivered in 1% DMSO (v/v)). Each assay point was performed in quadruplicate and standard deviation is depicted. (b) Schematic representation of HTRF γ-secretase assay. Cleavage of Sb4 substrate (SEQ ID NO:27) by γ-secretase at the 40-site is detected using G2-10 antibody that binds only cleaved substrate. HTRF detection method is incorporated to quantify enzyme activity. Anti-mouse IgG linked europium fluorophore binds to the G2-10 antibody, and Streptavidin-conjugated XL665 fluorophore binds at the biotinylated portion of Sb4. Following cleavage of Sb4, all reaction entities come into close proximity allowing FRET to occur. Europium is stimulated with light at 337 nm, causing the release of a signal at 620 nm. 620 nm light stimulates XL665 fluorophore to release light at 665 nm and this is quantified on a plate reader. Data values are calculated as the fraction of 665 nm signal normalized to background 620 nm.

Figure 11:
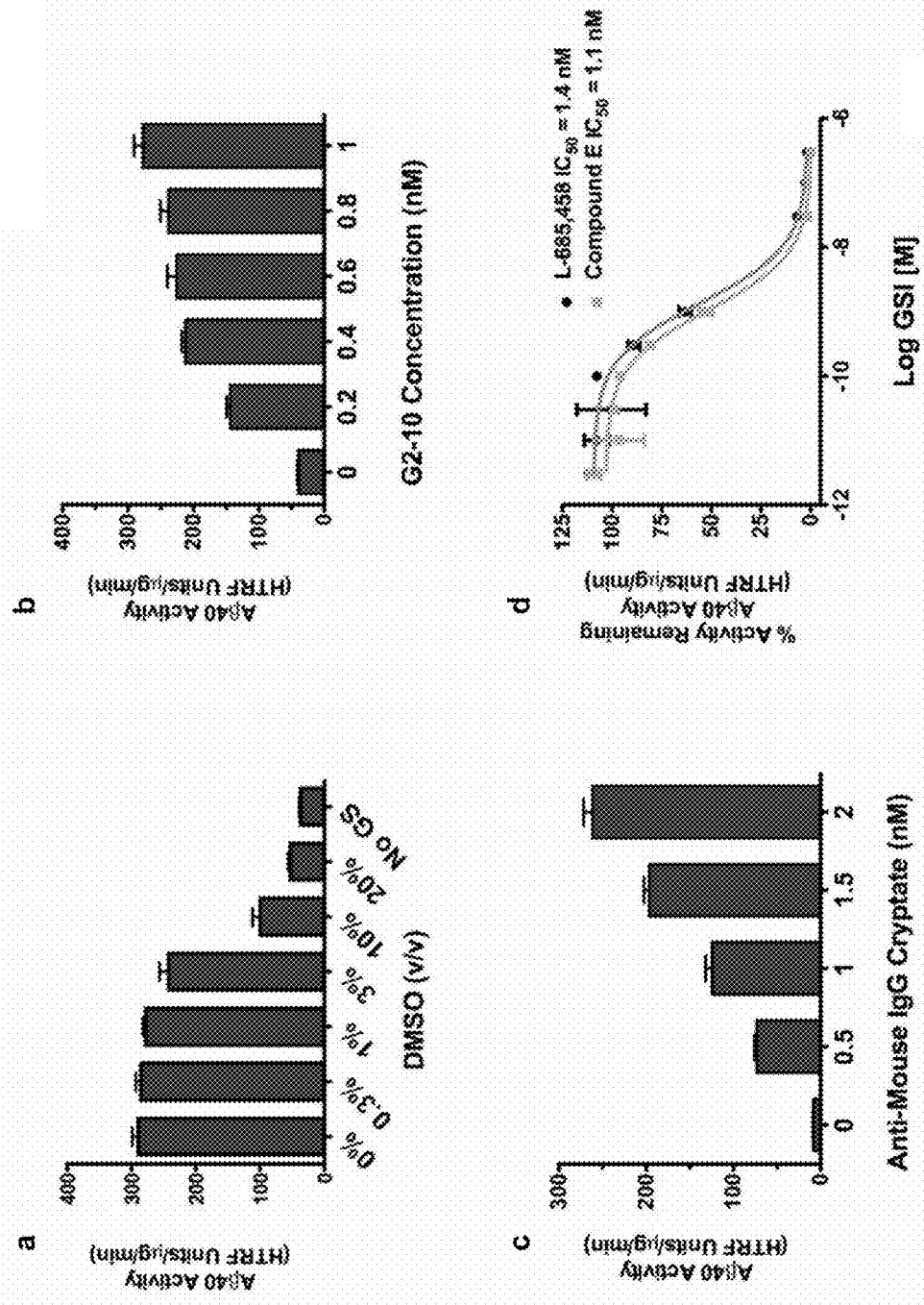
Figure 11:
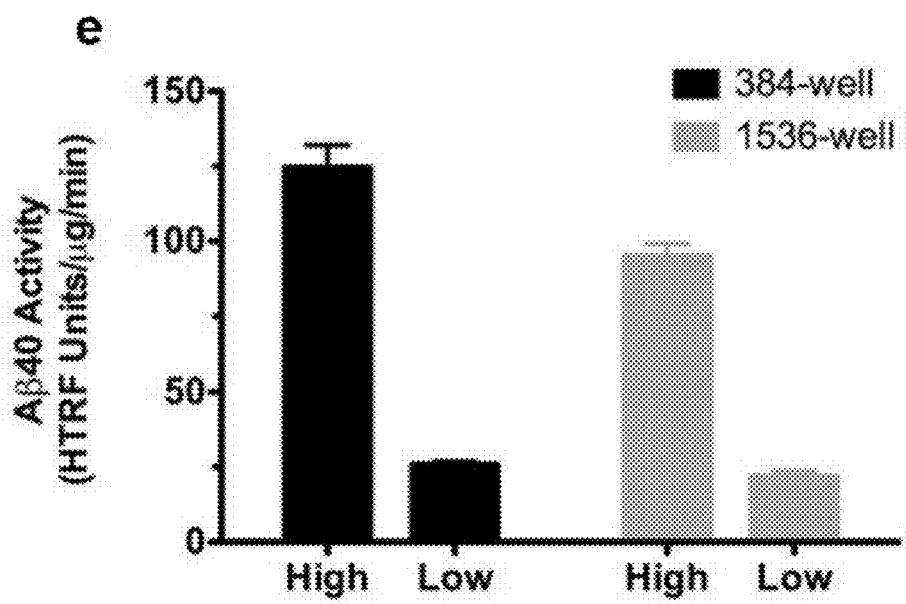

FIG. 11. Optimization of HTRF γ-secretase assay for utilization in a large scale high throughput screen. (a) Titration of tolerable levels of DMSO in the γ-secretase reaction portion of the HTRF assay, ranging from 0% to 20% DMSO or no γ-secretase enzyme (indicated as No GS). Due to the allotment of 1 ul of high throughput compounds in 10% DMSO for 1536-well screening, the γ-secretase assay needed to withstand a final DMSO concentration of 2% (v/v). (b) Optimization of G2-10 antibody concentration for characterization of cleaved substrate. (c) Anti-mouse IgG conjugated fluorophore was titrated. (d) Inhibitory potency of L685,458 and Compound E determined by the HTRF γ-secretase assay. Each assay point was performed in triplicate, and s.d. is plotted. (e) Optimization conditions were performed in a 384-well assay format with a final reaction volume of 20 μl. We finalized assay parameters to 0.3 nM G2-10 and 1 nM Anti-Mouse IgG Europium cryptate. Finally, the assay was miniaturized to a 1536-well format in a 10 μl reaction volume (5 μl γ-secretase reaction mix+5 μl HTRF detection mix). (a)-(c), (e) For each assay point, n=8 and s.d. is plotted.

Figure 12:
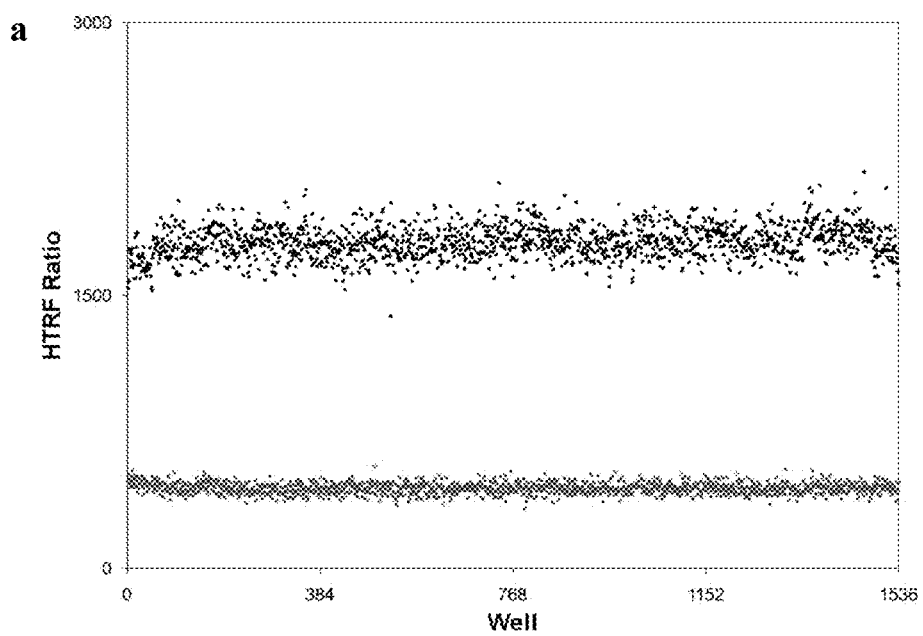
Figure 12:
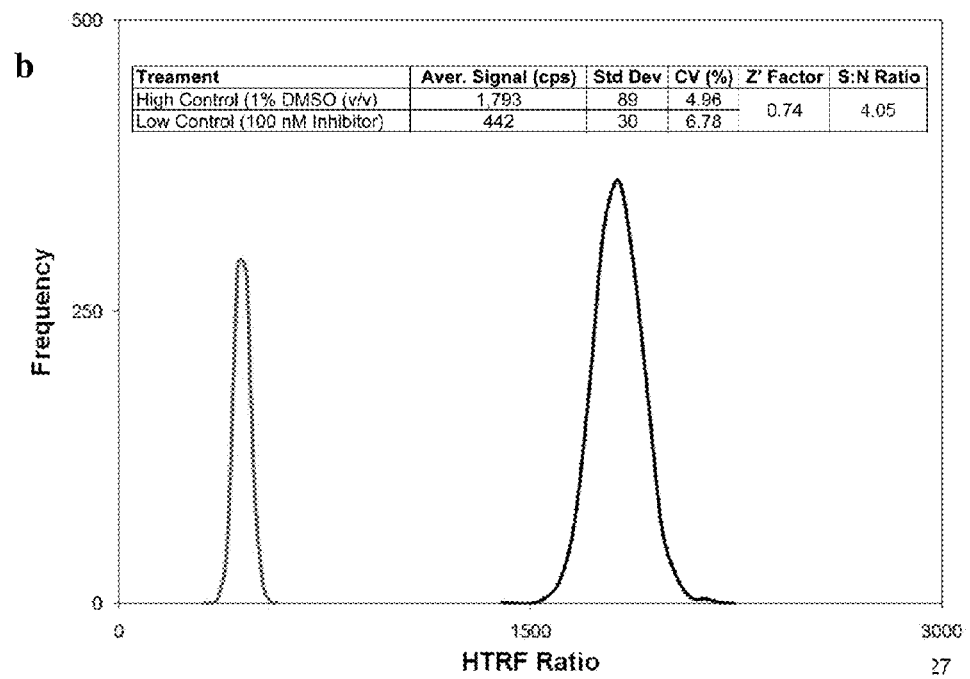
Figure 12:
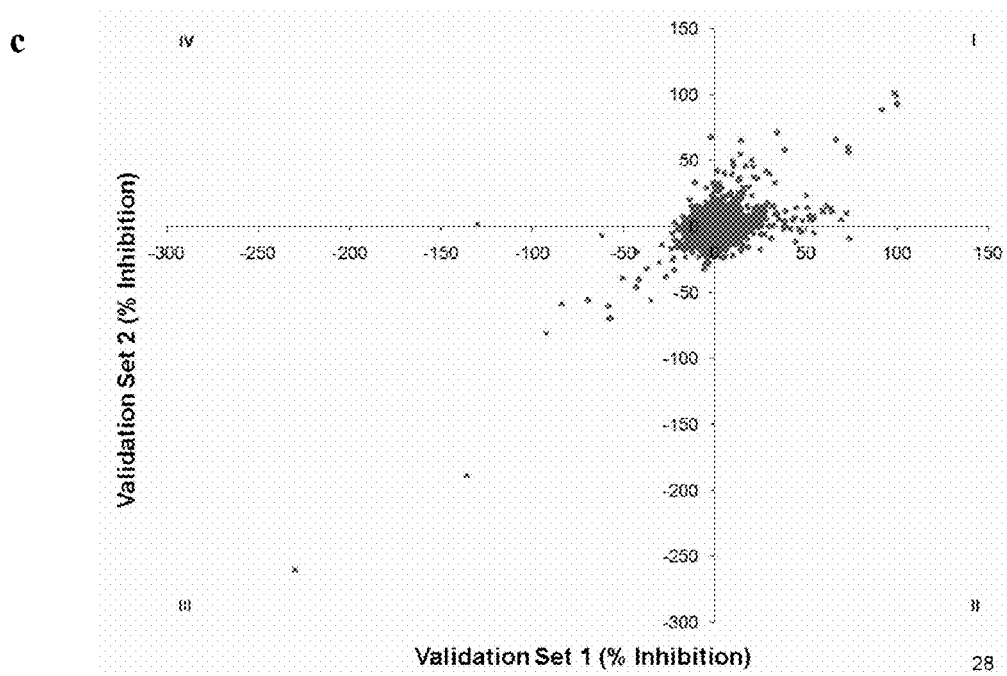
Figure 12:
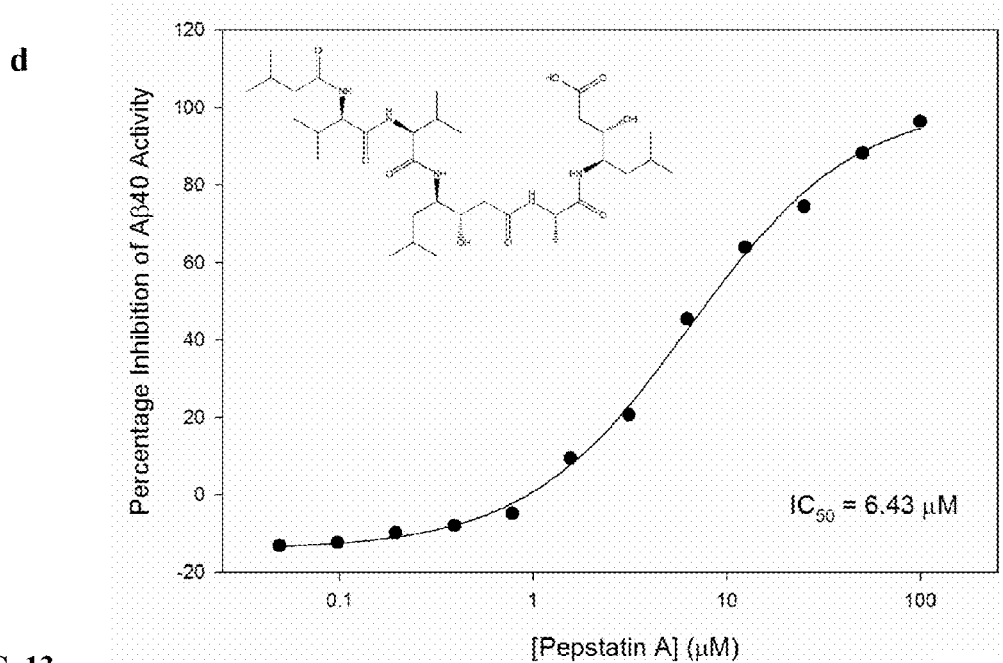

FIG. 12. Aβ40 (SEQ ID NO:16) HTRF assay pilot screen results. (a) Distribution of high and low control wells from the control run using one 1536-well plate representing high control wells and one 1536-well plate representing low control wells. High control wells contain 1% DMSO (v/v), whereas low control wells contain 100 nM Compound E GSI in 1% DMSO (v/v). (b) Frequency distribution of the high and low control wells yielding a Z' value of 0.74 and a signal to noise ratio of 4 to 1. (c) Scatter plot analysis from the Aβ40 HTRF pilot screen. A library of approximately 3,000 compounds was screened on two successive days to evaluate assay reproducibility and performance. Strong positives in Quadrant I represent potential GSIs. Data points located in Quadrant II or IV are compounds that did not reproduce in both runs of the assay. The majority of compounds located around the X- and Y-axis intercept represent compounds that did not exhibit any significant activity against γ-secretase. (d) Dose response curve of pepstatin A. Data points were performed in duplicate.

Figure 13:
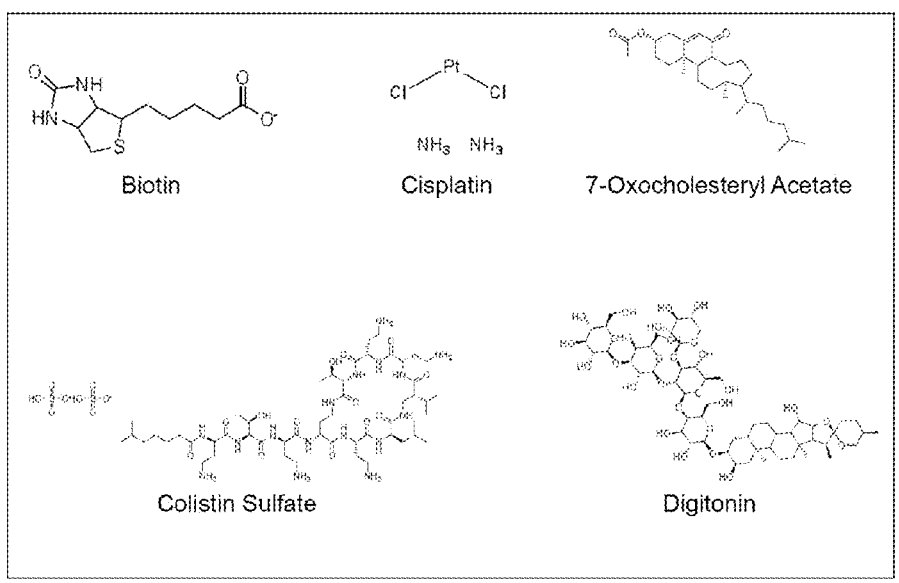

FIG. 13: Structures of selected active compounds identified in the HTRF based γ-secretase pilot screen.

Figure 14:
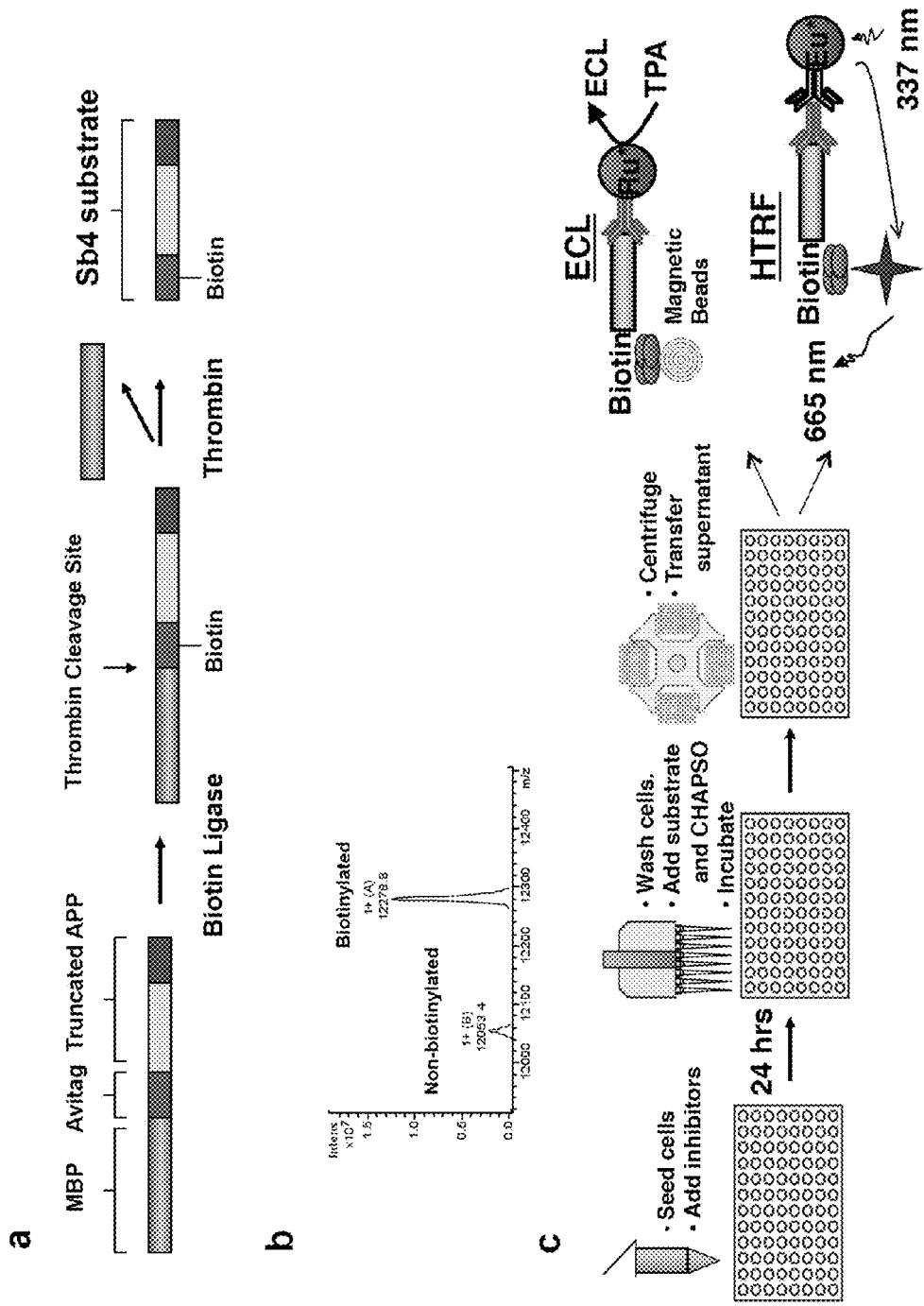

FIG. 14. Recombinant γ-Secretase Substrate Allows for Detection of Protease Activity Directly in Cells. (a) Sb4 γ-Secretase Substrate. Schematic of the truncated Sb4 substrate (SEQ ID NO:27) from the amyloid precursor protein that has an engineered MBP tag as well as AviTag for purification and biotinylation, respectively. A thrombin cleavage site between the MBP tag and AviTag allows for the removal of MBP by thrombin treatment following substrate purification. (b) LC-MS analysis identified Sb4 at the expected size and determined that greater than 90% of purified Sb4 is shown to be biotinylated. (c) Development of an Exo-Cell Assay. Utilization of the Sb4 substrate in conjunction with a small amount of CHAPSO detergent allows for real-time examination of ℵ-secretase activity directly from cells using ECL or homogenous time-resolved fluorescence (HTRF) detection methods in 96-well format.

Figure 15:
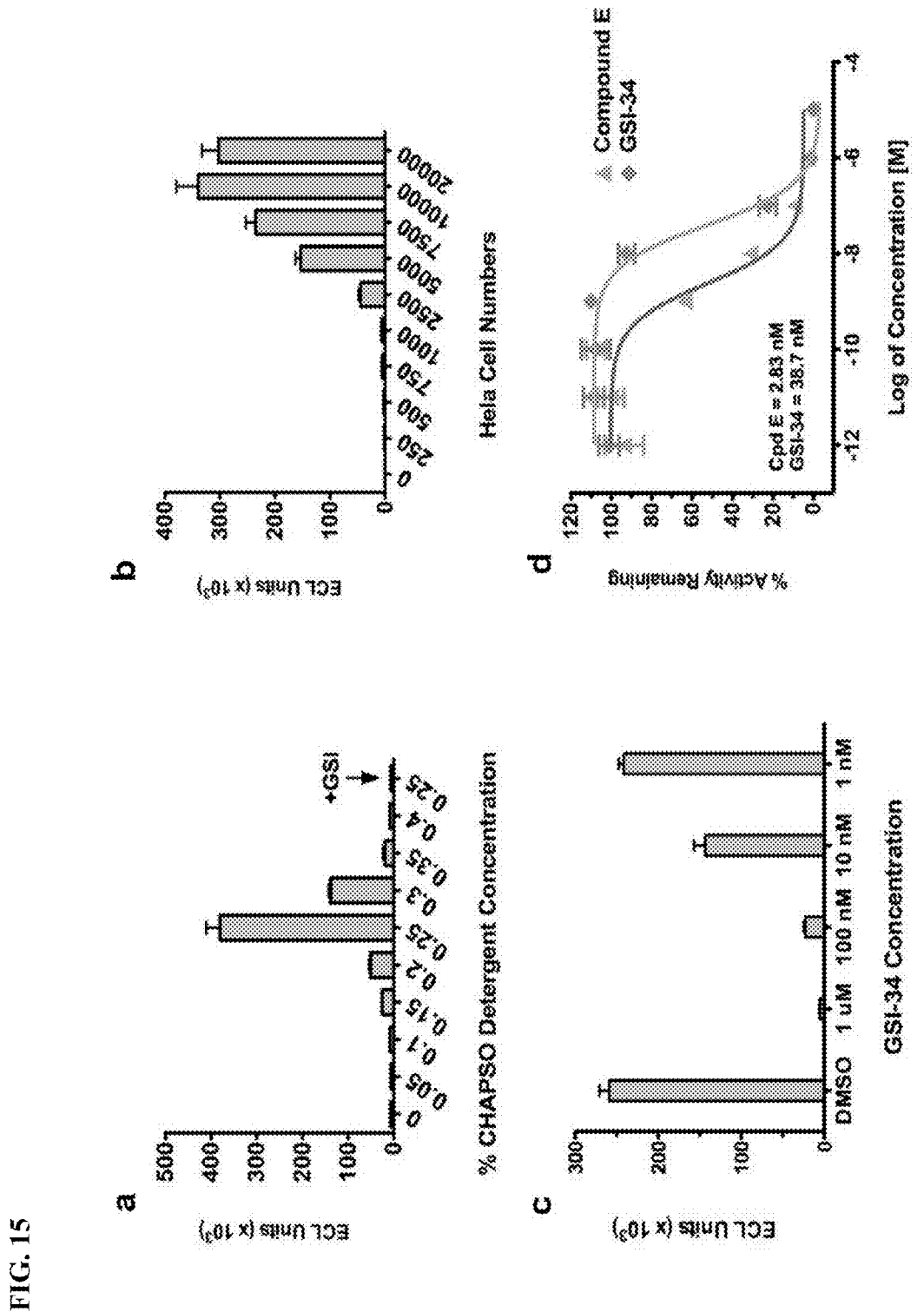

FIG. 15. Development of an Exo-Cell Assay for Quantification of γ-Secretase Activity in Cells. (a) Titration of CHAPSO detergent in the exo-cell assay. CHAPSO detergent was titrated to determine the optimal amount required for stimulating γ-secretase activity. The titration was performed using $1 \times 10^5$ HeLa cells and 1 μM Sb4 substrate. This reaction was incubated for 2.5 hours at 37° C. Supernatant was then collected and analyzed using ruthenylated G2-10* antibody. Activity was quantitated by measuring ECL. For each assay point n=4, and s.d. is plotted. (b) Titration of the number of HeLa adenocarcinoma cells from which the exo-cell assay can detect ℵ-secretase activity. The indicated number of HeLa cells were seeded in a 96-well plate and allowed to attach overnight. The next day media was removed and replaced with fresh media containing 0.25% CHAPSO detergent, 1 µM Sb4 substrate, and DMSO or 1 µM Compound E to define background. Values plotted represent the activity quantified for each cell number assay point with GSI-defined background subtracted. For each assay point n=4, and s.d. is plotted. (c) Dose-dependent inhibition of ℵ-secretase activity by GSI-34. HeLa cells were seeded 10,000 cells per well of 96-well plate. The cells were treated for 24 hrs with the indicated concentration of GSI-34 inhibitor. Cells were then washed once with PBS and then the exo-cell assay was performed using 1 µM Sb4 substrate and 0.25% CHAPSO detergent. (d) $IC_{50}$ values of distinct GSIs in extended exo-cell assay. $IC_{50}$ values were obtained for 2 distinct GSI compounds using the extended exo-cell assay. For each data point n=3, and s.d. is plotted.

Figure 16:
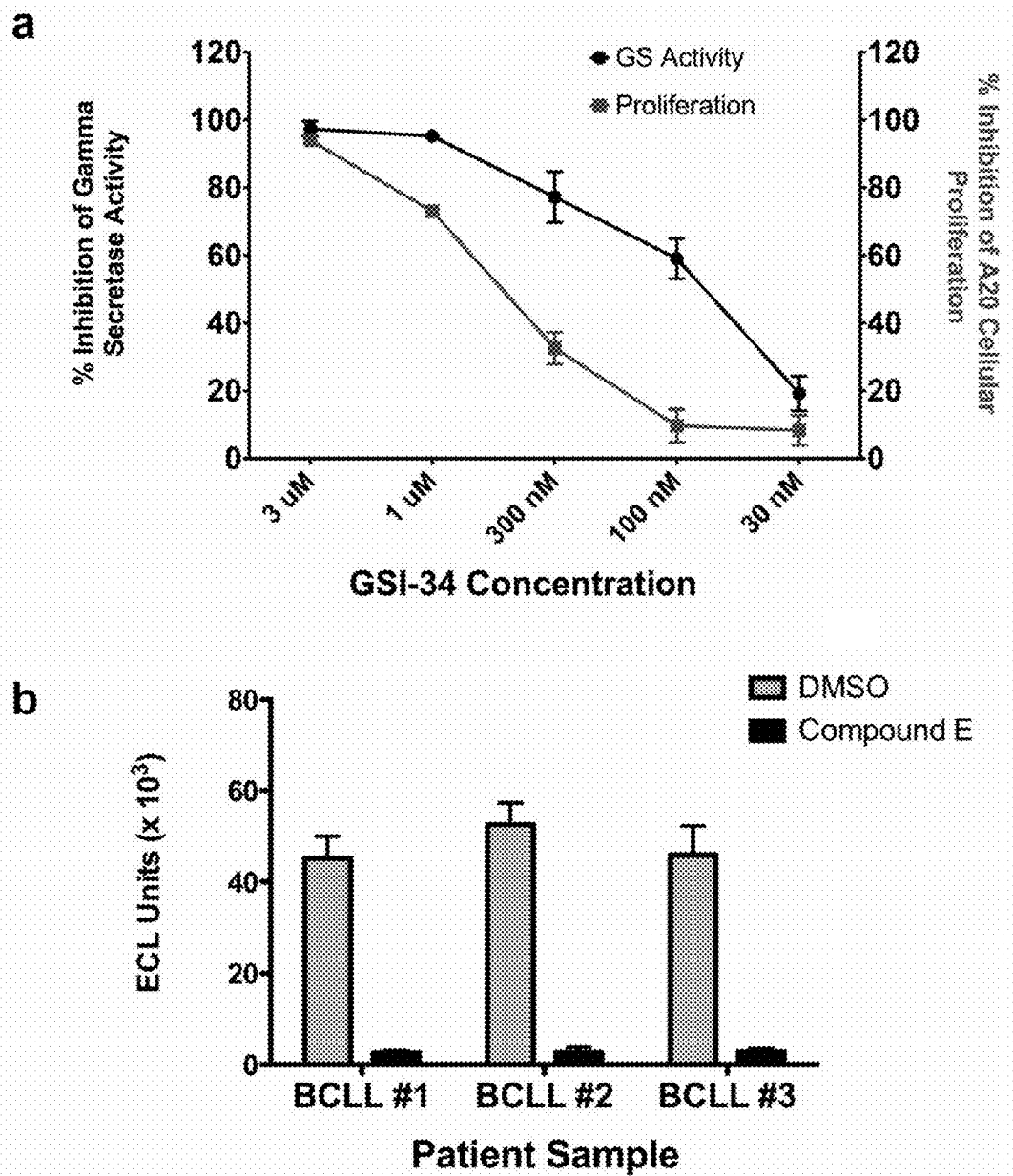

FIG. 16. Examination of Real-Time γ-Secretase Activity in A20 Lymphoma and in Primary B-CLL Patient Samples. (a) Correlation Between real-time inhibition of ℵ-secretase activity and GSI-mediated inhibition of A20 mouse lymphoma proliferation. Two 96-well plates were seeded with 50,000 A20 mouse lymphoma cells per well in 100 µl RPMI media. To each of these plates an additional 100 µl of media was added containing DMSO or GSI-34 to indicated final concentration. These plates were incubated for 48 hours at 37° C. Following this incubation, one plate was used in a real-time exo-cell assay to quantitate the real-time inhibition of γ-secretase in A20 cells. Briefly, A20 cells were pelleted and media removed. Fresh media containing 1 µM Sb4 substrate and 0.25% CHAPSO detergent were added and the exo-cell assay was performed. For each assay point n=4, and s.d. is plotted. Additionally, to the other 96-well plate 2 µCi/ml [$^3$H]thymidine was incubated with the cells for 5 hours. Following 5-hour incubation at 37° C., the amount of tritiated DNA was quantified on a β-counter. For each proliferation assay point n=10, and s.d. is plotted. (b) Real-time γ-secretase activity in primary B-CLL patient samples. B-CLL cells were seeded in 96-well plate at a concentration of 50,000 cells per well. These were allowed to attach overnight. Subsequently, the media was removed and fresh media was added back that contained either DMSO or 1 µM Compound E inhibitor. This was incubated for 24 hrs at 37° C. Cells were then washed once in PBS and exo-cell assay was performed as previously described. For each assay point n=4, and s.d. is plotted.

5. TERMINOLOGY

As used herein, the term "amyloid precursor protein" ("APP") refers to an integral membrane protein that is expressed in tissues and concentrated in the synapses of neurons. As used herein, "APP" refers to a mammalian APP, e.g., a human APP. As used herein, the term "APP" or "APP polypeptide" is meant to encompass all isoforms and forms of APP, both wild-type and synthetic. Exemplary APP isoforms include, but are not limited to, APP695 (SEQ ID NO:1), the 695 amino acid splice variant of APP (see GenBank accession no. Y00264 or SwissProt/UniProt Acc. No. P05067, and Kang et al., 1987, *Nature* 325:733-736), APP 751 (SEQ ID NO:2), the 751 amino acid splice variant of APP (see SwissProt/UniProt Acc. No. P05067, or Ponte, et al., 1988, *Nature* 331:525-527), and APP770 (SEQ ID NO:3), the 770 amino acid splice variant of APP (see SwissProt/UniProt Acc. No. PO5067 or Kitaguchi, et al., 1988, *Nature* 331:530-532). Other isoforms of APP include APP714, L-APP752, L-APP733, L-APP696, L-APP677, APP563 and APP365. Use of the term APP herein is meant to include all isoforms containing mutations found in familial AD and other amyloidosis conditions. For example, these mutations include, but are not limited to, the Swedish double mutation (Lys670Asn, Met671Leu); the London mutation (Val717Ile); the Indiana mutation (Val717Leu); naturally occurring mutations including Val717Phe, Val717Gly, Ala713Thr, and Ala713Val; the Austrian mutation (Thr714Ile); the Iranian mutation (Thr714Ala); the French mutation (Val715Met); the German mutation (Val715Ala); the Florida mutation (Ile716Val); the Australian mutation (Leu723Pro); the Flemish mutation (Ala692Gly); the Dutch mutation (Glu693Gln); the Arctic mutation (Glu693Gly); the Italian mutation (Glu693Lys); the Iowa mutation (Asp694Asn); and the amyloidosis-Dutch type mutation (Glu693Gln). (All numbering herein is relative to the APP770 form). Use of the term APP herein further includes proteins containing one or more additions, deletions, insertions, or substitutions relative to the isoforms described above, and APP proteins from humans and other species. Unless a specific isoform is specified, APP when used herein generally refers to any and all isoforms of APP, with or without mutations, from any species.

In addition, the term "APP polypeptide" relates in a non-limiting fashion to any fragment or portion of an APP isoform, and to modifications thereof. The terms "fragment" and "portion" are used interchangeably herein. A modification of a fragment of an APP polypeptide includes one or more additions, deletions, insertions, or substitutions relative to the isoforms described above.

As used herein the term "polypeptide" and related terms designates any and all compositions in which a given amino acid residue is linked to a neighboring amino acid residue via a peptide bond. As used herein the term "peptide" is synonymous with "polypeptide". In this usage the length of the polypeptide is not limited to a specified minimum number of amino acid residues. A polypeptide may be composed of only naturally occurring amino acid residues, or it may include modified, synthetic, or derivatized amino acid residues as well. As used herein, the term "APP fragment" refers to any polypeptide derived from a wild-type or synthetic APP. The term APP fragment further refers to any portion of an APP that can be processed or cleaved, by one or more processing or cleavage reactions, to Aβ.

As used herein, the term "source of APP" refers to any in vivo, ex vivo or in vitro substance containing APP or a fragment thereof. For example, a "source" can include, but is not limited to, a live organism (including a human patient, or a laboratory or veterinary animal) or a sample therefrom (such as a tissue or body fluid, or extract thereof), a cell (such as a primary cell or cell line, or extract thereof), extracellular medium or matrix or milieu, or isolated protein. Sources of APP are not limited to naturally occurring APP, but can also comprise the modified APP polypeptides or variants thereof described herein.

As used herein, the term "source of gamma-secretase" refers to any in vivo, ex vivo or in vitro substance containing gamma-secretase. For example, a "source" can include, but is not limited to, a live organism (including a human patient, or a laboratory or veterinary animal) or a sample therefrom (such as a tissue or body fluid, or extract thereof), a cell (such as a primary cell or cell line, or extract thereof), extracellular medium or matrix or milieu, or isolated protein. Sources of gamma-secretase are not limited to naturally occurring gamma-secretase, but can also comprise engineered and/or synthesized gamma-secretase.

As used herein, the term "source of beta-secretase" refers to any in vivo, ex vivo or in vitro substance containing gamma-secretase. For example, a "source" can include, but is not limited to, a live organism (including a human patient, or a laboratory or veterinary animal) or a sample therefrom (such as a tissue or body fluid, or extract thereof), a cell (such as a primary cell or cell line, or extract thereof), extracellular medium or matrix or milieu, or isolated protein. Sources of beta-secretase are not limited to naturally occurring gamma-secretase, but can also comprise engineered and/or synthesized beta-secretase.

As used herein, the term "modified APP" refers to any APP or APP fragment, so long as said APP or APP fragment comprises a gamma-secretase cleavage site and at least one amino acid modification, wherein said modification comprises at least one amino acid substitution, deletion, insertion, or addition in the region of APP identified herein as the gamma-secretase inhibitory domain. An example of a modified APP is a modified APP695 substrate with residues 613-617 deleted therefrom (termed "modified APP695" herein). A modified APP of the invention may further comprise amino acid modifications outside of the gamma-secretase inhibitory domain, wherein said amino acid modifications comprise any number of amino acid substitutions, deletions, insertions, or additions, so long as said modified APP retains its ability to be cleaved by gamma-secretase. The invention further encompasses variants of the modified APP described herein. Variants of the modified APP described herein may comprise any number of amino acid substitutions, deletions, insertions, or additions, so long as said variants retain a gamma-secretase cleavage site and a gamma-secretase inhibitory domain comprising at least one amino acid modification, wherein said modification comprises at least one amino acid substitution, deletion, insertion, or addition in the gamma-secretase inhibitory domain. The comparative similarity of a modified APP described herein, and a variant thereof, is defined by the "relative sequence identity" of that modified APP sequence variant thereof. In certain embodiments, a variant of a modified APP as described herein is at least 95% identical to that modified APP (based on amino acid sequence homology, i.e., the "relative sequence identity"). In other embodiments, a variant of a modified APP as described herein is at least 90% identical to that modified APP. In other embodiments, a variant of a modified APP as described herein is at least 85% identical to that modified APP. In other embodiments, a variant of a modified APP as described herein is at least 80%, at least 75%, at least 70%, at least 65%, or at least 60% percent identical to that modified APP (based on amino acid sequence homology). For all such variants, it is noted that the functional ability to serve as a "suitable substrate" for the gamma-secretase enzyme, such as in the assays described herein, or also in other methods now known in the art, or, optionally, also including methods later known in the art, is essential to the inclusion of any such variant within the operation of the invention.

As used herein, the term "unmodified gamma-secretase substrate" refers to a gamma-secretase substrate or a fragment or variant thereof that does not have a modification in the gamma-secretase inhibitory domain. As used herein, an "unmodified gamma-secretase substrate control" refers to a gamma-secretase substrate or a fragment or variant thereof that is substantially similar to a modified gamma-secretase substrate of the invention or variant thereof save for the fact that it does not have a modification in the gamma-secretase inhibitory domain.

As used herein, an "unmodified APP control" refers to an APP or fragment thereof that is substantially similar to a modified APP of the invention or variant thereof save for the fact that it does not have a modification in the gamma-secretase inhibitory domain.

As used herein, the term "amyloid-beta (frequently referred to herein as "Aβ")" refers to any one of a set of related peptides obtained from the proteolytic cleavage of APP. Cleavage of APP by beta-secretase generates two APP fragments, referred to herein as "beta-CTF" (beta-C-terminal fragment) and "soluble beta-APP" (s-beta-APP). Beta-CTF is an approximately 100 amino acid fragment, whose N-terminus is the N-terminus of Aβ and serves as the substrate for γ-secretase to provide an Aβ peptide. An example of a naturally occurring beta-CTF sequence, i.e., the beta-CTF of APP695, is provided in SEQ ID NO:8. Derivatives of the beta-CTF portion of APP provided in SEQ ID NO:8 are well known in the art (see, e.g., Lichtenthaler, et al., 1997, *Biochemistry* 36:15396-15403; and Selkoe, 1999, *Nature* 399: A23-A31). Such derivatives can themselves provide a beta-CTF domain or can serve as a starting point for creating additional derivatives. Subsequent gamma-secretase cleavage of beta-CTF generates the C-terminus of Aβ. Because gamma-secretase cleavage of the beta-CTF fragment occurs over a short stretch of amino acids rather than at a single peptide bond, Aβ ranges in size from, e.g., 38 to 43 peptides. However, Aβ peptides of 40 and 42 amino acids in length ("Aβ40" and "Aβ42," (SEQ ID NOS:16 and 17, respectively) predominate.

As used herein, the term "gamma-secretase inhibitory domain" refers to the amino acid sequence of APP discovered by the inventors as that which inhibits the cleavage of APP by gamma-secretase. The amino acid sequence corresponding to the gamma-secretase inhibitory domain of APP comprises the amino acid sequence Leu-Val-Phe-Phe-Ala (SEQ ID NO:19). Because APP isoforms represent splice variants, the amino acid location (i.e., the numeric position in the protein sequence) of the gamma-secretase inhibitory domain differs from one isoform to the next. However, the amino acid residue location of the gamma-secretase inhibitory domain is identical in the beta-CTF fragments generated by cleavage of any common APP isoform by beta-secretase (see FIGS. 1 and 9A), since the CTF is invariant among them. Thus, reference made herein to the gamma-secretase inhibitory domain, in terms of amino acid numbering and location, will use the amino acid location of the gamma-secretase inhibitory domain as it exists in beta-CTF or derivative thereof, i.e., amino acid positions 17-21. Thus, e.g., reference to a modified APP comprising a modification to amino acid 17 of the gamma-secretase inhibitory domain of said modified APP is understood to correspond to a modification to amino acid 17 of a beta-CTF sequence or a derivative thereof.

As used herein, the term "Aβ" refers to any of the polypeptides produced by the sequential action of β-secretase and γ-secretase on an APP. Depending on the exact location of the proteolysis by γ-secretase, a variety of polypeptides is produced. Examples of possible species of Aβ is given by SEQ ID NOS:15-17.

As used herein, the term "gamma-secretase" refers to an enzyme(s) with the ability to cleave at the gamma-secretase site of a protein having a gamma-secretase cleavage site, e.g., APP. As used herein, gamma-secretase includes all recombinant forms, mutations, and other variants of gamma-secretase so long as these maintain a functional capability to catalyze the cleavage of molecules or substrates bearing gamma-secretase cleavage sites.

As used herein, the term "beta-secretase" refers to an enzyme(s) with the ability to cleave at the beta-secretase site of a protein having a beta-secretase cleavage site, e.g., APP. As used herein, beta-secretase includes all recombinant forms, mutations, and other variants of beta-secretase so long as these maintain a functional capability to catalyze the cleavage of molecules or substrates bearing beta-secretase cleavage sites. Beta-secretase, as used herein, encompasses an enzyme that is sometimes known in the literature as "BACE" or "BACE1" (see, e.g., Vassar, et al., 1999, *Science* 286:735-741).

As used herein, the term "alpha secretase" refers to an enzyme(s) with the ability to cleave at the alpha-secretase site of a protein having an alpha-secretase cleavage site, e.g., APP. As used herein, alpha-secretase includes all recombinant forms, mutations, and other variants of alpha-secretase so long as these maintain a functional capability to catalyze the cleavage of molecules or substrates bearing alpha-secretase cleavage sites.

As used herein, the term "gamma-secretase cleavage site" refers to the peptide bond in any amino acid sequence that is cleaved by gamma-secretase, or to a polynucleotide encoding the cleavable amino acid sequence.

As used herein, the term "beta-secretase cleavage site" refers to the peptide bond in any amino acid sequence that is cleaved by beta-secretase, or to a polynucleotide encoding the cleavable amino acid sequence.

As used herein, the term "alpha-secretase cleavage site" refers to the peptide bond in any amino acid sequence that is cleaved by alpha-secretase, or to a polynucleotide encoding the cleavable amino acid sequence.

As used herein, the term "gamma-secretase substrate" refers to any naturally occurring or synthetic sequence of amino acids (e.g., polypeptides and proteins) comprising a gamma-secretase cleavage site. Non-limiting examples of gamma-secretase substrates include all modified APP as described herein, APP, neuregulin-1, alpha-protocadherin, SCNB2, Tie-1, beta-APP like protein 1, beta-APP like protein 2, nectin-3, nectin-4, alcadein alpha, alcadein gamma, APLP1, APLP2, ApoER2, CD43, CD44, CSF1R, CXCL16, CX3CL1, DCC, Deltal, E-cadherin, EphrinB1, EphrinB2, EphB2, ErbB4, GHR, HLA-A2, IGF1R, IFN-alpha-R2, IL-1R2, IR, IRE1-alpha, Jagged2, L1, LRP, LPR1B, LRP2, LRP6, N-cadherin, Nectin1-alpha, notch, Notch1, Notch2, Notch3, Notch4, NRADD, p75-NTR, PKHD1, Pcdh-alpha-4, Pcdh-gamma-C3, PTP-kappa, PTP-µ, PTP-LAR, S or CS1b, SorLA, Sortilin, Syndecan3, Tyrosinase, TYRP1, TYRP2, VEGF-R1, VGSC-beta-2, and VLDLR.

As used herein, the term "uninhibited gamma-secretase substrate" also termed herein a "gamma-secretase substrate released from inhibition" refers to a gamma-secretase substrate toward which gamma-secretase has an increased activity. In certain embodiments, an uninhibited gamma-secretase substrate comprises a modification in the gamma-secretase inhibitory domain, wherein said modification to the gamma-secretase inhibitory domain reduces and/or eliminates the inhibitory effect of the gamma-secretase inhibitory domain. In certain embodiments, an uninhibited gamma-secretase substrate comprises a modification to the nicastrin docking motif. Accordingly, an uninhibited gamma-secretase substrate will be more susceptible to gamma-secretase cleavage, i.e., gamma-secretase will exhibit a higher degree of activity toward the uninhibited gamma-secretase substrate, than a gamma-secretase substrate that has an identical structure and/or sequence save for a modification in the gamma-secretase inhibitory domain.

As used herein, the term "conservative amino acid substitution" refers to the replacement of one amino acid residue by another, chemically similar, amino acid residue. Non-limiting examples of such conservative substitutions are: substitution of any hydrophobic residue (alanine, isoleucine, leucine, valine, or methionine) for another; substitution of any ionic residue for another ionic residue of the same charge (e.g., arginine for lysine; glutamic acid for aspartic acid); substitution of any polar residue (serine, threonine, asparagines, glutamine, cysteine, histidine or tyrosine) for another; and substitution of any aromatic amino acid (tryptophan, tyrosine, histidine, or phenylalanine) for another. Conservative amino acid substitutions that are known or reasonably predicted to not adversely alter the desired functionality of the novel sequences disclosed herein are disclosed. Such disclosed conservative amino acid substitutions are considered to fall within the scope of the sequence listings that include the novel modified APP sequences disclosed and claimed herein.

As used herein, the term "isolated," as it refers to a modified APP of the invention refers to any modified APP that has been isolated from any source, e.g., from a cell that naturally expresses the modified APP or that has been engineered to express the modified APP.

The term "contacting" refers to bringing into association, either directly or indirectly, two or more substances or compositions. Contacting may occur in vivo, ex vivo or in vitro. Commonly contacting a first composition with a second composition brings about a transformation in the first composition, the second composition, or both compositions.

As used herein, the term "consists essentially," with respect to a modified APP of the invention, indicates that the reference sequence can be modified by N-terminal and/or C-terminal additions or deletions that do not cause a substantial decrease in the ability of the gamma-secretase substrate to be cleaved compared to the reference sequence.

As used herein, the term "transfection" refers to any of the methods known in the art for introducing DNA into a cell including, but not limited to, the methods of calcium phosphate or calcium chloride mediated transfection, electroporation, and infection with a retroviral vector.

As used herein, the terms "fusion protein", "chimeric protein", and related terms and phrases, refer to a protein or polypeptide engineered to contain at least two polypeptide regions or domains, each having recognizable structure, function, or similar attribute, and, optionally, a linking peptide to operatively link the two polypeptides into one continuous polypeptide. The at least two polypeptide regions in a fusion protein are derived from different sources, and therefore a fusion protein comprises two polypeptide regions not normally joined together in nature.

As used herein, the term "linking sequence (or linker peptide)" contains one or more amino acid residues joined in peptide bonds. A linking sequence serves to join two polypeptide regions of differing origins in a fusion protein via a peptide bond between the linking sequence and each of the polypeptide regions.

As used herein, the terms tag, probe or label refer interchangeably to a moiety bound to a target substance that permits easy detection or assay of the target. A tag, probe or label may include a particular amino acid sequence defining a polypeptide tag, probe or label, or it may include a non-proteinaceous moiety that can be readily detected by a laboratory assay. Examples of a polypeptide tag include maltose binding protein, Avi-Tag, the FLAG epitope, glutathione dehydrogenase, horse radish peroxidase, and so forth. Additionally a tag, probe or label may include an antibody that specifically binds to a target substance, or to a second antibody. An antibody tag, probe or label may itself further bear detectable moiety as a tag, probe or label, such as a fluorescent moiety, including a fluorescent moiety that can serve as a fluorescence donor or a fluorescence energy acceptor, or a moiety that responds in a chemiluminescence assay.

As used herein, the term "gamma-secretase assay" refers to any assay which can be used to measure the activity of gamma-secretase toward a gamma-secretase substrate.

As used herein, the term "about" or "approximately," when used in conjunction with a number, refers to any number that is experimentally or empirically similar to a referenced number, such that a property that the number describes is not significantly distinguished from a reference property.

As used herein, the terms "increase," "increases," and "increased," in the context of the activity of gamma-secretase refer, in some embodiments, to: (i) an increase of 0.5%, 1%. 1.5%, 2%, 5%, 10%, 20%, 30%, 40%, 50% or more; or (ii) an increase of 1.5, 2, 3, 4, or 5 fold or more.

As used herein, the terms "change" or "changed," in the context of the activity of gamma-secretase refer, in some embodiments, to: (i) a change of 0.5%, 1%. 1.5%, 2%, 5%, 10%, 20%, 30%, 40%, 50% or more; or (ii) a change of 1.5, 2, 3, 4, or 5 fold or more.

As used herein, the term "gamma-secretase inhibitor" refers to any molecule, compound, and/or substance capable of reducing and/or eliminating the activity of gamma-secretase.

As used herein, the term "compound," unless otherwise specified or clear from the context of the specification, refers to any agent being tested for its ability to modulate gamma-secretase activity. In one embodiment, the term "compound" refers to a small molecule.

As used herein, the term "small molecule" and analogous terms include, but are not limited to, peptides, peptidomimetics, amino acids, amino acid analogs, polynucleotides, polynucleotide analogs, nucleotides, nucleotide analogs, other organic and inorganic compounds (i.e., including heteroorganic and organometallic compounds) and forms thereof having a molecular weight of less than about 10,000 Da, or less than about 5,000 Da, or less than about 1,000 Da, or less than about 500 Da, or less than about 100 Da.

As used herein, the term "therapeutic agent" refers to any molecule, compound, and/or substance that is used for the purpose of treating and/or managing a disease or disorder, i.e., a gamma-secretase inhibitor. Examples of therapeutic agents include, but are not limited to, proteins, compounds, immunoglobulins (e.g., multi-specific Igs, single chain Igs, Ig fragments, polyclonal antibodies and their fragments, monoclonal antibodies and their fragments), peptides (e.g., peptide receptors, selectins), binding proteins, biologics, chemospecific agents, chemotoxic agents (e.g., anti-cancer agents), proliferation-based therapy, radiation, chemotherapy, anti-angiogenic agents, and small molecule drugs.

As used herein, the phrase "disease associated with aberrant Aβ level(s)" refers to any condition characterized by an abnormal amount of at least one species of Aβ peptide including, but not limited to, Aβ43, Aβ42, Aβ40, Aβ39, Aβ38, Aβ37, Aβ34, Aβ11-43, Aβ11-42, Aβ11-40, Aβ11-39, Aβ11-38, Aβ11-37, Aβ11-34; by an abnormal relative amount of different species of Aβ peptides (such as the ratio of Aβ42 to Aβ40); by an abnormal amount, or relative amount, of Aβ in a particular form (such as monomeric, oligomeric, or fibrillar form; in solution or aggregated in a plaque; in a particular conformation, etc.); and/or by an abnormal amount, or relative amount, of Aβ in a particular location (such as intracellular, membrane-associated or extracellular location, or in a particular tissue or body fluid). The abnormal amount of one or more Aβ peptides, Aβ forms and/or Aβ in a particular location can be relative to a condition that is a normal, non-disease state. Diseases and disorders characterized by altered Aβ levels are known in the art and/or described herein, and include, for example, AD, Down syndrome, Parkinson's disease, diffuse Lewy body disease, progressive supranuclear palsy, Hereditary Cerebral Hemorrhage with Amyloidosis-Dutch Type (HCHWA-D), cerebral amyloid angiopathy (CAA), and mild cognitive impairment (MCI).

As used herein, the term "cancer" refers to a neoplasm or tumor resulting from abnormal uncontrolled growth of cells. The term "cancer" encompasses a disease involving both pre-malignant and malignant cancer cells. In some embodiments, cancer refers to a localized overgrowth of cells that has not spread to other parts of a subject, i.e., a localized, or at times benign, tumor. In other embodiments, cancer refers to a malignant tumor, which has invaded and destroyed neighboring body structures and spread to distant sites. In yet other embodiments, the cancer is associated with a specific cancer antigen.

As used herein, the terms "fragment", "portion" and related terms and phrases when used in relation to a polypeptide having a stated or understood length refer to any amino acid sequence comprising an amino acid sequence of contiguous amino acid residues that is shorter than that of the replete polypeptide by at least one residue. Thus a fragment or portion of a polypeptide having N residues may range in length from as many as N-1 contiguous residues to as few as two contiguous residues of the sequence of the polypeptide.

As used herein, the term "effective amount" in the context of administering a gamma-secretase inhibitor to a subject refers to the amount of a gamma-secretase inhibitor which is sufficient to achieve a prophylactic and/or therapeutic effect.

As used herein, the term "in combination," in the context of the administration of a gamma-secretase inhibitor, refers to the administration of two or more gamma-secretase inhibitors, or the administration of one or more gamma-secretase inhibitors and one or more additional agents. The use of the term "in combination" does not restrict the order in which two or more gamma-secretase inhibitors or one or more gamma-secretase inhibitor and another agent are administered to a subject in need thereof.

As used herein, the term "separating" and similar terms and phrases, when applied to a cell, connote resolving various fractions that may occur in the cell from one another. Frequently a cell is disrupted to disperse its contents into a suspending solvent prior to resolving its fractions. Disruption may be accomplished, for example, by homogenization, extrusion through a high shear device such as a French press, sonication, and so on. The resulting cell-free suspension can then be resolved into fractions as above. In general, as used herein, "separating" includes any disruption of the cell.

As used herein, the term "host cell" includes a particular subject cell transformed or transfected with an instant nucleic acid construct and the progeny or potential progeny of such a cell. Progeny of such a cell may not be identical to the parent cell transfected with the nucleic acid construct due to mutations or environmental influences that may occur in succeeding generations or integration of the nucleic acid construct into the host cell genome.

As used herein, the term "isolated," as it refers to a gamma-secretase inhibitor, means the physical state of a gamma-secretase inhibitor after being separated and/or purified from precursors and other substances found in a synthetic process (e.g., from a reaction mixture) or natural source or combination thereof according to a process or processes described herein or which are well known to the skilled artisan (e.g., chromatography, recrystallization and the like) in sufficient purity to be capable of characterization by standard analytical techniques described herein or well known to the skilled artisan. In a specific embodiment, the gamma-secretase inhibitor is at least 60% pure, at least 65% pure, at least 70% pure, at least 75% pure, at least 80% pure, at least 85% pure, at least 90% pure or at least 99% pure as assessed by techniques known to one of skill in the art.

As used herein, the terms "polynucleotide", "nucleic acid" and "nucleotides" refer to deoxyribonucleotides, deoxyribonucleic acids, ribonucleotides, and ribonucleic acids, and polymeric forms thereof, and includes either single- or double-stranded forms. In some embodiments, nucleic acid refers to deoxyribonucleic acids (e.g., cDNA or DNA). In other embodiments, nucleic acid refers to ribonucleic acids (e.g., mRNA or RNA).

As used herein, the terms "subject" and "patient" are used interchangeably, and refer to an animal (e.g., birds, reptiles, and mammals), such as a mammal including a non-primate (e.g., a camel, donkey, zebra, cow, pig, horse, goat, sheep, cat, dog, rat, and mouse) and a primate (e.g., a monkey, chimpanzee, and a human). In a specific embodiment, the subject is a human.

As used herein, the terms "therapies" and "therapy" can refer to any method(s), composition(s), and/or agent(s) that can be used in the prevention, treatment and/or management of a disease or one or more symptoms thereof.

As used herein, the terms "treat," "treatment," and "treating" refer, in the context of the administration of a gamma-secretase inhibitor alone or in combination with another agent to a subject to treat a gamma-secretase associated disease, to a therapeutic benefit achieved. In a specific embodiment, such terms refer to at least one or more of the following effects resulting from the administration of a gamma-secretase inhibitor or other agent to a subject: (i) the reduction or amelioration of the severity of the disease or a symptom associated therewith; (ii) the reduction in the duration of the disease or a symptom associated therewith; (iii) the regression of the disease or a symptom associated therewith; (iv) the prevention of the development, onset or recurrence of a symptom associated with the disease; (v) the reduction in organ damage or failure associated with the disease; (vi) the reduction in hospitalization of a subject having the disease; (vii) the reduction in hospitalization length of a subject having the disease; (viii) the increase in the survival of a subject with the disease; (ix) the elimination of the disease or a symptom associated therewith; (x) the inhibition of the progression of the disease or a symptom associated therewith; (xi) the cure of the disease; and/or (xii) the enhancement or improvement the therapeutic effect of another agent. In some embodiments, treatment does not refer to a cure for the disease, but the inhibition of the progression or worsening of the disease.

Concentrations, amounts, cell counts, percentages and other numerical values may be presented herein in a range format. It is to be understood that such range format is used merely for convenience and brevity and should be interpreted flexibly to include not only the numerical values explicitly disclosed as the limits of the range but also to include all the individual numerical values or sub-ranges encompassed within that range as if each numerical value and sub-range were explicitly disclosed.

6. DETAILED DESCRIPTION OF THE INVENTION

TABLE 1

| Table of Sequences | |
|---|---|
| SEQ ID NO.: | Sequence Identifying Information |
| 1 | Human APP 695 Uniprot accession number P05067-4 |
| 2 | Human APP 751 Uniprot accession number P05067-8 |
| 3 | Human APP 770 Uniprot accession number P05067-1 |
| 4 | sAPPα |
| 5 | sAPPβ |
| 6 | Modified APP695 (corresponds to the modified APP695 substrate bearing deletion 613-617) |
| 7 | αCTF |
| 8 | βCTF |
| 9 | S1 (includes N-terminal Avi-Tag) |
| 10 | S2 (includes N-terminal Avi-Tag) |
| 11 | S3 (includes N-terminal Avi-Tag and C-terminal FLAG epitope) |
| 12 | S4 (includes N-terminal Avi-Tag and C-terminal FLAG epitope) |
| 13 | S5 (includes N-terminal Avi-Tag and C-terminal FLAG epitope) |
| 14 | S6 (includes N-terminal Avi-Tag and C-terminal FLAG epitope) |
| 15 | Aβ38 |
| 16 | Aβ40 |
| 17 | Aβ42 |
| 18 | Aβ(17-23) |
| 19 | Aβ(17-21) |
| 20 | Aβ(17-20) |
| 21 | Modified Aβ(17-23) |
| 22 | Random peptide |
| 23 | PM-1 (D, E, methyl ester; C-terminal amide) |
| 24 | Retro inverso peptide derivative RI-PM-1; all D-amino acids; D, E are methyl ester derivatives; N-glycylurethane; C-terminal amide |
| 25 | βCTFΔ (Aβ17-23 deleted from of βCTF; N-terminal FLAG): |
| 26 | βCTFmut |
| 27 | Sb4: Substrate construct with N-terminal Avi-Tag |
| 28 | C100Flag |

6.1. Methods of Making Modified Gamma-Secretase Substrates

The uninhibited gamma-secretase substrates provided herein can made by standard recombinant DNA techniques or by protein synthetic techniques, e.g., by use of a peptide synthesizer. For example, a nucleic acid molecule encoding a gamma-secretase substrate of the invention can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, e.g., *Current Protocols in Molecular Biology*, Ausubel et al., eds., John Wiley & Sons, 1992).

Recombinant synthesis techniques for encoding and expressing polypeptides are also well known in the art. Such techniques employ a nucleic acid template for polypeptide synthesis. Starting with a particular amino acid sequence and the known degeneracy of the genetic code, a large number of different encoding nucleic acid sequences can be obtained. The degeneracy of the genetic code arises because almost all amino acids are encoded by different combinations of nucleotide triplets or "codons." The translation of a particular codon into a particular amino acid is well known in the art (see, e.g., Lewin GENES I, p. 172, Oxford University Press, 1994, for a complete table of codons and their translated amino acid residues, incorporated herein by reference). Amino acids are abbreviated to a three-letter code, which is used in sequence listings provided herein, and further abbreviated to an equivalent one-letter code (see Voet and Voet, Biochemistry, John Wiley & Sons, New York, 1990; page 66 for a table of amino acid names, three-letter codes, and one-letter codes, incorporated herein by reference).

The nucleotide sequences encoding gamma-secretase substrates for use in making modified gamma-secretase substrates of the invention may be obtained from any information available to those of skill in the art (i.e., from Genbank, the literature, or by routine cloning). The nucleotide sequence coding for a gamma-secretase substrate can be modified using approaches known to those of skill in the art, e.g., site-directed mutagenesis, and inserted into an appropriate expression vector, i.e., a vector which contains the necessary elements for the transcription and translation of the inserted protein-coding sequence. In some instances, the gamma-secretase substrate sequence can be truncated in order to remove a specific domain, such as the targeting domain. The techniques for modifying or truncating DNA are well known to those of skill in the art of molecular biology. Also, the IL-3 and the gamma-secretase substrate sequences can be ligated in such a way as to generate a DNA sequence that, when translating, creates a polypeptide that is a gamma-secretase inhibitor of the invention. A variety of host-vector systems may be utilized in the present invention to express the protein-coding sequence. These include, but are not limited to, mammalian cell systems infected with virus (e.g., vaccinia virus, adenovirus, etc.); insect cell systems infected with virus (e.g., baculovirus); microorganisms such as yeast (e.g. *Pichia*) containing yeast vectors; or bacteria (such as *E. coli*) transformed with bacteriophage, DNA, plasmid DNA, or cosmid DNA. The expression elements of vectors vary in their strengths and specificities. Depending on the host-vector system utilized, any one of a number of suitable transcription and translation elements may be used.

The expression of a gamma-secretase substrate of the invention may be controlled by any promoter or enhancer element known in the art. Promoters which may be used to control expression of a gamma-secretase substrate include, but are not limited to, the SV40 early promoter region (Bernoist and Chambon, 1981, *Nature* 290:304-310), the promoter contained in the 3' long terminal repeat of Rous sarcoma virus (Yamamoto, et al., 1980, *Cell* 22:787-797), the herpes thymidine kinase promoter (Wagner et al., 1981, *Proc. Natl. Acad. Sci. U.S.A.* 78:1441-1445), the regulatory sequences of the metallothionein gene (Brinster et al., 1982, *Nature* 296:39-42), the tetracycline (Tet) promoter (Gossen et al., 1995, *Proc. Nat. Acad. Sci. U.S.A.* 89:5547-5551); prokaryotic expression vectors such as the β-lactamase promoter (VIIIa-Kamaroff, et al., 1978, *Proc. Natl. Acad. Sci. U.S.A.* 75:3727-3731), or the tac promoter (DeBoer, et al., 1983, *Proc. Natl. Acad. Sci. U.S.A.* 80:21-25; see also "Useful proteins from recombinant bacteria," in *Scientific American*, 1980, 242:74-94); plant expression vectors comprising the nopaline synthetase promoter region (Herrera-Estrella et al., *Nature* 303:209-213) or the cauliflower mosaic virus 35S RNA promoter (Gardner, et al., 1981, *Nucl. Acids Res.* 9:2871), and the promoter of the photosynthetic enzyme ribulose biphosphate carboxylase (Herrera-Estrella et al., 1984, *Nature* 310:115-120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, *Cell* 38:639-646; Ornitz et al., 1986, Cold Spring Harbor Symp. Quant. Biol. 50:399-409; MacDonald, 1987, *Hepatology* 7:425-515); insulin gene control region which is active in pancreatic beta cells (Hanahan, 1985, *Nature* 315:115-122), immunoglobulin gene control region which is active in lymphoid cells (Grosschedl et al., 1984, *Cell* 38:647-658; Adames et al., 1985, *Nature* 318:533-538; Alexander et al., 1987, *Mol. Cell. Biol.* 7:1436-1444), mouse mammary tumor virus control region which is active in testicular, breast, lymphoid and mast cells (Leder et al., 1986, *Cell* 45:485-495), albumin gene control region which is active in liver (Pinkert et al., 1987, *Genes and Devel.* 1:268-276), alpha-fetoprotein gene control region which is active in liver (Krumlauf et al., 1985, *Mol. Cell. Biol.* 5:1639-1648; Hammer et al., 1987, *Science* 235:53-58); alpha 1-antitrypsin gene control region which is active in the liver (Kelsey et al., 1987, *Genes and Devel.* 1:161-171), beta-globin gene control region which is active in myeloid cells (Mogram et al., 1985, *Nature* 315:338-340; Kollias et al., 1986, *Cell* 46:89-94; myelin basic protein gene control region which is active in oligodendrocyte cells in the brain (Readhead et al., 1987, *Cell* 48:703-712); myosin light chain-2 gene control region which is active in skeletal muscle (Sani, 1985, *Nature* 314:283-286); neuronal-specific enolase (NSE) which is active in neuronal cells (Morelli et al., 1999, *Gen. Virol.* 80:571-83); brain-derived neurotrophic factor (BDNF) gene control region which is active in neuronal cells (Tabuchi et al., 1998, *Biochem. Biophysic. Res. Com.* 253:818-823); glial fibrillary acidic protein (GFAP) promoter which is active in astrocytes (Gomes et al., 1999, *Braz. J. Med. Biol. Res.* 32(5):619-631; Morelli et al., 1999, *Gen. Virol.* 80:571-83) and gonadotropic releasing hormone gene control region which is active in the hypothalamus (Mason et al., 1986, *Science* 234:1372-1378). In a specific embodiment, the expression of a gamma-secretase substrate of the invention is regulated by a constitutive promoter. In another embodiment, the expression is regulated by an inducible promoter. In another embodiment, the expression is regulated by a tissue-specific promoter.

In a specific embodiment, a vector is used that comprises a promoter operably linked to a gamma-secretase substrate encoding nucleic acid, one or more origins of replication and, optionally, one or more selectable markers (e.g., an antibiotic resistance gene).

In mammalian host cells, a number of viral-based expression systems may be utilized. In cases where an adenovirus is used as an expression vector, the polypeptide or fusion protein coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, 1984, *Proc. Natl. Acad. Sci. USA* 81:355-359). Specific initiation signals may also be required for efficient translation of inserted fusion protein coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, *Methods in Enzymol.* 153:51-544).

Expression vectors containing inserts of a gene encoding a gamma-secretase substrate of the invention can be detected by three general approaches: (a) nucleic acid hybridization, (b) presence or absence of "marker" gene functions, and (c) expression of inserted sequences. In the first approach, the presence of a gene encoding a gamma-secretase substrate in an expression vector can be detected by nucleic acid hybridization using probes comprising sequences that are homologous to an inserted gene encoding the gamma-secretase substrate. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of a nucleotide sequence encoding a gamma-secretase substrate in the vector. For example, if the nucleotide sequence encoding the gamma-secretase substrate is inserted within the marker gene sequence of the vector, recombinants containing the gene encoding the gamma-secretase substrate insert can be identified by the absence of the marker gene function. In the third approach, recombinant expression vectors can be identified by assaying the gene product (e.g., gamma-secretase substrate) expressed by the recombinant. Such assays can be based, for example, on the physical or functional properties of the gamma-secretase substrate in in vitro assay systems, e.g., binding to an antibody.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered gamma-secretase substrates may be controlled. Furthermore, different host cells have characteristic and specific mechanisms for the translational and post-translational processing and modification (e.g., glycosylation, phosphorylation) of proteins. Appropriate cell lines or host systems can be chosen to ensure the desired modification and processing of the foreign protein expressed. For example, expression in a bacterial system will produce an unglycosylated product and expression in yeast will produce a glycosylated product. Eukaryotic host cells which possess the cellular machinery for proper processing of the primary transcript, glycosylation, and phosphorylation of the gene product may be used. Such mammalian host cells include, but are not limited to, CHO, VERY, BHK, HeLa, COS, MDCK, 293, 3T3, WI38, NS0, and in particular, neuronal cell lines such as, for example, SK-N-AS, SK-N-FI, SK-N-DZ human neuroblastomas (Sugimoto et al., 1984, *J. Natl. Cancer Inst.* 73: 51-57), SK-N-SH human neuroblastoma (*Biochim. Biophys. Acta*, 1982, 704: 450-460), Daoy human cerebellar medulloblastoma (He et al., 1992, *Cancer Res.* 52: 1144-1148) DBTRG-05MG glioblastoma cells (Kruse et al., 1992, In *Vitro Cell. Dev. Biol.* 28A: 609-614), IMR-32 human neuroblastoma (*Cancer Res.*, 1970, 30: 2110-2118), 1321N1 human astrocytoma (*Proc. Natl. Acad. Sci. U.S.A.* 1977, 74: 4816), MOG-G-CCM human astrocytoma (*Br. J. Cancer* 1984, 49: 269), U87MG human glioblastoma-astrocytoma (*Acta Pathol. Microbiol. Scand.* 1968, 74: 465-486), A172 human glioblastoma (Olopade et al., 1992, *Cancer Res.* 52: 2523-2529), C6 rat glioma cells (Benda et al., 1968, *Science* 161: 370-371), Neuro-2a mouse neuroblastoma (*Proc. Natl. Acad. Sci. U.S.A.* 1970, 65: 129-136), NB41A3 mouse neuroblastoma (*Proc. Natl. Acad. Sci. U.S.A.* 1962, 48: 1184-1190), SCP sheep choroid plexus (Bolin et al., 1994, *J. Virol. Methods* 48: 211-221), G355-5, PG-4 Cat normal astrocyte (Haapala et al., 1985, *J. Virol.* 53: 827-833), Mpf ferret brain (Trowbridge et al., 1982, In *Vitro* 18: 952-960), and normal cell lines such as, for example, CTX TNA2 rat normal cortex brain (Radany et al., 1992, *Proc. Natl. Acad. Sci. U.S.A.* 89: 6467-6471) such as, for example, CRL7030 and Hs578Bst. Furthermore, different vector/host expression systems may effect processing reactions to different extents.

For long-term, high-yield production of gamma-secretase substrates, stable expression is preferred. For example, cell lines which stably express the gamma-secretase substrate of the invention may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched medium, and then are switched to a selective medium. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express a gamma-secretase substrate of the invention.

A number of selection systems may be used, including but not limited to the herpes simplex virus thymidine kinase (Wigler, et al., 1977, *Cell* 11:223), hypoxanthine-guanine phosphoribosyltransferase (Szybalska & Szybalski, 1962, *Proc. Natl. Acad. Sci. U.S.A.* 48:2026), and adenine phosphoribosyltransferase (Lowy, et al., 1980, *Cell* 22:817) genes can be employed in tk-, hgprt- or aprt-cells, respectively. Also, antimetabolite resistance can be used as the basis of selection for dhfr, which confers resistance to methotrexate (Wigler, et al., 1980, *Proc. Natl. Acad. Sci. U.S.A.* 77:3567; O'Hare, et al., 1981, *Proc. Natl. Acad. Sci. U.S.A.* 78:1527); gpt, which confers resistance to mycophenolic acid (Mulligan & Berg, 1981, *Proc. Natl. Acad. Sci. U.S.A.* 78:2072); neo, which confers resistance to the aminoglycoside G-418 (Colberre-Garapin, et al., 1981, *J. Mol. Biol.* 150:1); and hygro, which confers resistance to hygromycin (Santerre, et al., 1984, *Gene* 30:147).

Once a gamma-secretase substrate of the invention has been produced by recombinant expression or by chemical synthesis, it may be purified by any method known in the art for purification of a protein, for example, by chromatography (e.g., ion exchange, affinity, particularly by affinity for the specific antigen after Protein A, and sizing column chromatography), centrifugation, differential solubility, or by any other standard technique for the purification of proteins.

6.2 Modified Gamma-Secretase Substrates 6.2.1 Modified APP

The modified APPs and modified gamma-secretase substrate polypeptides disclosed herein represent novel gamma-secretase substrates on which gamma-secretase has a higher proteolytic activity than the enzyme exhibits on naturally-occurring APP, and so may be termed "uninhibited" or "enhanced". As described herein, including in the Examples below, a modified APP substrate can be used in assays for measuring gamma-secretase activity and for identification of gamma-secretase inhibitors. Any modified APP or variant thereof can be used in accordance with the methods of the invention, as long as said modified APP or variant thereof comprises: a gamma-secretase cleavage site and at least one amino acid modification, wherein said modification comprises at least one amino acid substitution, deletion, insertion, or addition in the region of APP identified herein as the gamma-secretase inhibitory domain.

In various embodiments this disclosure presents a polypeptide that includes at least a portion of a modified Aβ sequence, in which at least one of the amino acid residues corresponding to residues 17-21 of Aβ is modified. This polypeptide is constructed to serve as a substrate for γ-secretase activity. In certain embodiments the polypeptide is at least 28 amino acid residues in length. In other embodiments at least one of the amino acid residues corresponding to amino acid residues 17-21 of Aβ is deleted. In still additional embodiments at least one of the amino acid residues corresponding to amino acid residues 17-21 of Aβ is substituted by another residue.

In various embodiments, the modified APP comprises at least amino acid residues 1 to 42 of Aβ42, wherein amino acid residues 1-21 of Aβ42 are modified.

In several embodiments, the modified APP comprises at least amino acid residues 17 to 42 of Aβ42, wherein one or more amino acid residues at position Aβ17-21 are modified, and wherein the modified APP is at least 35 amino acid residues in length.

In another embodiment, the modified APP comprises a modification to the phenylalanine residue at one or both of amino acid residues at position 19 or 20 of Aβ42. In an aspect of this embodiment, the phenylalanine residues at both of positions 19 and 20 of Aβ42 are modified.

In various embodiments of a modified polypeptide, an amino acid residue, for example a residue in the sequence Aβ17-21, is modified by substitution of the naturally occurring amino acid at the given position by a conservative amino acid substitution.

In another embodiment, the modified APP comprises the amino acid sequence identified in SEQ ID NO:6 (substrate S1 of Table 2), SEQ ID NO:7 (substrate S4 of Table 2), SEQ ID NO:8 (substrate S5 of Table 2), SEQ ID NO:9 (substrate S6 of Table 2), SEQ ID NO:10 [β-CTFΔ], SEQ ID NO:11 [ modified APP695 substrate in which residues 613-617 are deleted (termed "modified APP695" herein)], SEQ ID NO:18 [ the C-terminal fragment of APP in which residue Aβ19 (F) is mutated to A (C100F19A)], SEQ ID NO:19 (C100F20A), or SEQ ID NO:20 (C100F19AF20A).

In some embodiments of the invention, the modified APP comprises APP isotype APP 695, APP 714, APP 751 or APP 770 comprising one or modifications, such as a substitution, insertion or deletion of one more amino acids.

In some embodiments, the modified APP may be bound to a reporter protein, detectable marker, or affinity tag. Reporter proteins that may be used in the practice of this aspect of the invention may include, e.g., green fluorescent protein ("GFP"), luciferase, or β-galactosidase. In some embodiments, the modified APP may be in the form of a fusion protein comprising the modified APP and one or more tags, probes or labels. In some embodiments, the tag is separated from the modified APP with a protease cleavage site, e.g., a thrombin cleavage site. In a specific embodiment, the tag is an AviTag, i.e., a 15-residue peptide recognized by biotin ligase. In other embodiments, the tag is an affinity tag such as maltose-binding protein (MBP) (see, e.g., US Application No. 2008/0021056), a $(His)_6$ tag (which binds metal chelate affinity column) and/or a FLAG epitope tag (having the sequence DYKDDDDK (amino acids 99-106 of SEQ ID NO:11) which binds anti-FLAG antibody). In some embodiments, the tag is present at the N-terminus of the modified APP. In other embodiments, the modified APP has the tag at the C-terminus.

In some embodiments, the modified APP is constitutively or inducibly expressed in a cell. In some embodiments, the modified APP is recombinant, synthetic, or genetically engineered. In certain embodiments, the modified APP is in substantially purified or substantially isolated form.

In certain embodiments, the invention comprises a DNA construct comprising DNA encoding the modified APP. The invention also contemplates expression vectors comprising such DNA constructs, and cells comprising these expression vectors. A variety of expression vectors are known in the art and can be used in the present invention including, but not limited to, pMC1neo (Stratagene), pSG5 (Stratagene), pcDNAI and pcDNAlamp, pcDNA3, pcDNA3.1, pCR3.1 (Invitrogen, San Diego, Calif.), EBO-pSV2-neo (ATCC 37593), pBPV-1 (8-2) (ATCC 37110), pdBPV-MMTneo (342-12) (ATCC 37224), pRSV gpt (ATCC 37199), pRSVneo (ATCC 37198), pCI.neo (Promega), pTRE (Clontech, Palo Alto, Calif.), pVlJneo, pIRESneo (Clontech, Palo Alto, Calif.), pCEP4 (Invitrogen, San Diego, Calif.), pSCl 1, and pSV2-dhfr (ATCC 37146). The choice of vector will depend upon the cell type in which it is desired to express the modified APP substrate, as well as on the level of expression desired, and the like.

In certain embodiments, the modified APP comprises natural variants of APP, and fragments thereof, including the Swedish mutation (Lys670Asn, Met671Leu); the Indiana mutation (Val717Leu); the London mutation (Val717Ile), Val717Phe, Val717Gly, Ala713Thr, Ala713Val, the Austrian mutation (Thr714Ile), the Iranian mutation (Thr714Ala), the French mutation (Val715Met), the German mutation (Val715Ala), the Florida mutation (Ile716Val), Ile 716Thr, the Australian mutation (Leu723Pro), the Flemish mutation (Ala692Gly), the Dutch mutation (Glu693Gln), the Arctic mutation (Glu693Gly), the Italian mutation (Glu693Lys), the Iowa mutation (Asp694Asn), and the amyloidosis-Dutch type mutation (Glu693Gln). The numbering of these natural variants of APP is relative to the APP770 form, but similar mutations may be found in other APP forms, or other APP forms and fragments may be mutated to have the corresponding mutations (see US Application No. 2007/0260058, which is incorporated by reference herein in its entirety).

6.3 Identification of Gamma-Secretase Substrates Released from Inhibition

The modified gamma-secretase substrates described in Section 6.2 and variants thereof can be used in accordance with the methods below to determine whether they represent uninhibited or enhanced gamma-secretase substrates.

In order to determine the activity of gamma-secretase toward a modified gamma-secretase substrate as described in Section 6.2 or a variant thereof, any method for measuring gamma-secretase activity described herein or previously known in the art may be used. For non-limiting examples of previously described methods for assaying the activity of gamma-secretase toward a gamma-secretase substrate, see US Patent Application Publication Nos. 2006/0036077, 2008/0021056, 2008/0085894, 2008/0076752; and U.S. Pat. Nos. 7,378,511 and 7,498,324, all of which are incorporated by reference herein in their entirety.

These methods are optionally conducted in the presence of a control. Any suitable control may be used, e.g., gamma-secretase substrate with a known ability to be cleaved by gamma-secretase (i.e., a "positive control"); a gamma-secretase substrate known to not be cleaved by gamma-secretase (i.e., a "negative control"); or a gamma-secretase substrate similar in sequence to the modified gamma-secretase substrate or variant thereof, wherein the only difference between said gamma-secretase substrate similar in sequence to the modified gamma-secretase substrate or variant thereof and the modified gamma-secretase substrate or variant thereof is that the former does not comprise a modification to the gamma-secretase inhibitory domain (an "unmodified gamma-secretase substrate control").

In the broadest sense, identifying an uninhibited gamma-secretase substrate comprises the steps of contacting a modified gamma-secretase substrate of the invention or variant thereof with gamma-secretase and measuring the cleavage of said modified gamma-secretase substrate of the invention or variant thereof by said gamma-secretase, wherein a modified gamma-secretase substrate of the invention or variant thereof is identified as an uninhibited gamma-secretase substrate if the activity of gamma-secretase toward the modified gamma-secretase substrate of the invention or variant thereof is increased relative to the activity of gamma-secretase toward an unmodified gamma-secretase substrate control or a negative control.

6.3.1 Electrochemiluminescence (ECL) Assay of Aβ peptides

In one embodiment, a method for identifying an uninhibited gamma-secretase substrate is the electrochemiluminescence ("ECL") assay of Aβ peptides (see Li, et al., 2000, Proc. Natl. Acad. Sci. USA 97:6138-6143; and Yin, et al., 2007, J. Biol. Chem. 282:23639-23644, both of which are incorporated by reference herein in their entirety). In an ECL assay an analyte to be detected is labeled with a chemiluminescent moiety whose chemiluminescence is redox dependent. A commonly used chemiluminescent moiety is a $Ru^{+2}$ complex which becomes chemiluminescent, and hence detectable with high sensitivity, upon oxidation to $Ru^{+3}$. Alternative electrochemiluminescent (ECL) probes equivalent to $Ru^{+2}$ complexes are contemplated for use herein. As implemented in various Examples provided herein, an antibody specific for an intended epitope such as one revealed in a γ-secretase proteolysis product is conjugated to a $Ru^{+2}$ complex. The moiety so conjugated may be termed "ruthenylated" herein. As applied herein an ECL assay comprises: (a) contacting a modified APP of the invention or variant thereof with a source of gamma-secretase; (b) incubating said modified APP of the invention or variant thereof with said source of gamma-secretase for a time period sufficient for gamma-secretase activity to take place; (c) adding an anti-Aβ ruthenylated antibody; and (d) detecting a γ-secretase product by a product-specific ruthenylated antibody using ECL. A modified APP of the invention or variant thereof is identified as an uninhibited gamma-secretase substrate if the activity of gamma-secretase toward the modified APP of the invention or variant thereof is increased relative to the activity of gamma-secretase toward an unmodified APP control or a negative control. ECL techniques are known in the art and described in, e.g., Yang, et al., 1994, Bio/Technology 12:193-194; and Khorkova, et al., 1998, J. Neurosci. Methods 82:159-166, both of which are incorporated by reference herein in their entirety.

In a specific embodiment, the source of gamma-secretase is a cell or cell membrane, e.g., a HeLa cell or constituent membrane, and the incubation of step (b) takes place in the presence of a detergent, e.g., CHAPSO, at a concentration optimized for the assay.

In another specific embodiment, the anti-Aβ antibody is one that binds the C-terminus of the modified APP of the invention or variant thereof that is exposed after gamma-secretase mediated cleavage at the Aβ40 gamma-secretase cleavage, e.g., the G2-10 antibody described in Li, et al., 2000, Proc. Natl. Acad. Sci. USA 97:6138-6143. In another specific embodiment, the anti-Aβ antibody is one that binds the C-terminus of the modified APP of the invention or variant thereof that is exposed after gamma-secretase mediated cleavage at the Aβ42 gamma-secretase cleavage, e.g., the G2-11 antibody described in Yin, et al., 2007, J. Biol. Chem. 282:23639-23644. In a more specific embodiment, the assay comprises an anti-Aβ antibody that binds the C-terminus of the modified APP of the invention or variant thereof that is exposed after gamma-secretase mediated cleavage at the Aβ40 gamma-secretase cleavage, e.g., the G2-10 antibody, and an anti-Aβ antibody that binds the C-terminus of the modified APP of the invention or variant thereof that is exposed after gamma-secretase mediated cleavage at the Aβ42 gamma-secretase cleavage, e.g., the G2-11 antibody. In some embodiments, the anti-Aβ antibody is ruthenylated.

In another specific embodiment, the assay includes a source of beta-secretase.

In another specific embodiment, the modified APP of the invention or variant thereof comprises a modification to at least one amino acid in the gamma-secretase inhibitory domain. In an aspect of this embodiment, said modification comprises a deletion of at least one amino acid in the gamma-secretase inhibitory domain. In a specific aspect of this embodiment, the entire gamma-secretase inhibitory domain is deleted. In another aspect of this embodiment, said modification comprises a substitution of at least one amino acid in the gamma-secretase domain. In a specific aspect of this embodiment, one or both of amino acid residues 19 and 20 of the gamma-secretase inhibitory domain comprise an amino acid that is not phenylalanine In another specific aspect of this embodiment, each amino acid in the gamma-secretase inhibitory domain is substituted, such that amino acid residue 17 is not leucine, amino acid residue 18 is not valine, amino acid residue 19 is not phenylalanine, amino acid residue 20 is not phenylalanine, and amino acid residue 21 is not alanine.

In another specific embodiment, the modified APP of the invention or variant thereof comprises the amino acid sequence of any one of SEQ ID NO: 6, 7, 8, 9, 10, 11, 18, 19, and 20 (specifying S1, S4, S5, S6, βCTFΔ, C100F19A (phenylalanine at 19 mutated to alanine), C100F20A, and C100F19AF20A).

In another specific embodiment, the modified APP of the invention or variant thereof demonstrates a kcat/Km greater than that of an unmodified APP.

6.3.2 Aβ Homogeneous Time Resolved Fluorescence (HTRF) Assay

In another embodiment, a method for identifying an uninhibited gamma-secretase substrate is a Homogeneous Time Resolved Fluorescence (HTRF) assay for proteolytic cleavage by gamma-secretase at a site corresponding to positions 38, or 40, or 42 of Aβ (i.e., at Aβ38, Aβ40, or Aβ42). HTRF combines a) homogeneous phase (e.g. liquid solution) fluorescence detection with b) time resolution and c) assessment of the distance separating an excitation donor and a fluorescence emitter to eliminate background fluorescence and provide both high sensitivity and high specificity of detection. A long-lived fluorophore, commonly a complex of a rare earth metal ion, such as a cryptate complex of the ion, permits detection to be delayed by time resolution until background fluorescence will already have decayed. Fluorescence resonance energy transfer between specific donor and acceptor further enhance specificity by restricting ultimate detection of fluorescence to instances of, for example, complex formation between them. As implemented in this disclosure, an HTRF assay comprises: (a) contacting a modified APP of the invention or variant thereof with a source of gamma-secretase, wherein said modified APP of the invention or variant thereof includes a detectable tag or label; (b) incubating said modified APP of the invention or variant thereof with said source of gamma-secretase for a time period sufficient for gamma-secretase activity to take place; (c) adding an HTRF detection mixture that includes (i) a first antibody that recognizes a gamma-secretase-cleaved peptide resulting from cleavage at the Aβ38, Aβ40, or Aβ42 gamma-secretase cleavage site but does not recognize uncleaved gamma-secretase substrates and (ii) a rare earth metal-labeled second antibody that binds the first antibody, and (iii) a fluorophore-conjugated reagent that binds to the detectable tag or label; (d) incubating said HTRF detection mixture with said modified APP of the invention or variant thereof and said source of gamma-secretase; and (e) measuring the cleavage of said modified APP of the invention or variant thereof by gamma-secretase using, generally, Fluorescence Resonance Energy Transfer ("FRET"), or more particularly, Homogeneous Time Resolved Fluorescence (HTRF), by exciting the rare earth metal and detecting fluorescence from the fluorophore of the conjugated reagent. By means of an HTRF assay, a modified APP or variant thereof is identified as an gamma-secretase substrate released from inhibition if the activity of gamma-secretase toward the modified APP of the invention or variant thereof to provide an Aβ38, Aβ40, or Aβ42 C-terminal polypeptide is increased relative to the activity of gamma-secretase toward an unmodified APP control or a negative control.

In a specific embodiment, the source of gamma-secretase is a cell or cell membrane, e.g., a HeLa cell or constituent membrane, and the incubation of step (b) takes place in the presence of a detergent, e.g., CHAPSO, at a concentration optimized for the assay.

In a specific embodiment, the antibody that recognizes gamma-secretase-cleaved peptides resulting from cleavage at the Aβ40 gamma-secretase cleavage site but does recognize uncleaved gamma-secretase substrates is the G2-10 antibody.

In another specific embodiment, the assay includes a source of beta-secretase.

In another specific embodiment, the modified APP of the invention or variant thereof comprises a modification to at least one amino acid in the gamma-secretase inhibitory domain. In an aspect of this embodiment, said modification comprises a deletion of at least one amino acid in the gamma-secretase inhibitory domain. In a specific aspect of this embodiment, the entire gamma-secretase inhibitory domain is deleted. In another aspect of this embodiment, said modification comprises a substitution of at least one amino acid in the gamma-secretase domain. In a specific aspect of this embodiment, one or both of amino acid residues 19 and 20 of the gamma-secretase inhibitory domain comprise an amino acid that is not phenylalanine In another specific aspect of this embodiment, each amino acid in the gamma-secretase inhibitory domain is substituted, such that amino acid residue 17 is not leucine, amino acid residue 18 is not valine, amino acid residue 19 is not phenylalanine, amino acid residue 20 is not phenylalanine, and amino acid residue 21 is not alanine.

In another specific embodiment, the modified APP of the invention or variant thereof comprises the amino acid sequence of any one of SEQ ID NO: 6, 7, 8, 9, 10, 11, 18, 19, and 20 (specifying S1, S4, S5, S6, βCTFΔ, C100F19A (phenylalanine at 19 mutated to alanine), C100F20A, and C100F19AF20A).

In another specific embodiment, the modified APP of the invention or variant thereof demonstrates a kcat/Km greater than that of an unmodified APP.

6.3.3 Cell Based Assays

In another embodiment, a method for identifying an uninhibited gamma-secretase substrate is a cell-based assay, wherein said assay comprises: (a) transfecting cells, in the presence of a source of gamma-secretase and a source of beta-secretase, with a plasmid containing the nucleotide sequence of a modified APP of the invention or variant thereof; (b) incubating said cells for a time period sufficient for beta-secretase and gamma-secretase activity to occur; and (c) detecting Aβ secreted by the cells, wherein a modified APP of the invention or variant thereof is identified as an uninhibited gamma-secretase substrate if the level of Aβ secreted by the cells is increased relative to level of Aβ secreted by the cells when transfected with an unmodified APP control or wild-type APP.

In a specific embodiment, the cells provide the source of gamma-secretase and the source of beta-secretase. In another specific embodiment, the cells are HEK293 cells.

In one aspect of this embodiment, anti-Aβ antibodies that are specific for a C-terminal epitope of Aβ38, Aβ40, or Aβ42, are added to the cell conditioned media (containing secreted Aβ) and the level of Aβ secreted by the cells is measured by ECL. In a specific embodiment, the anti-Aβ antibody is one that binds the C-terminus of the modified APP of the invention or variant thereof that is exposed after gamma-secretase mediated cleavage at the Aβ40 gamma-secretase cleavage, e.g., G2-10 antibody. In another specific embodiment, the anti-Aβ antibody is one that binds the C-terminus of the modified APP of the invention or variant thereof that is exposed after gamma-secretase mediated cleavage at the Aβ42 gamma-secretase cleavage, e.g., G2-11 antibody. In a more specific embodiment, the assay comprises an anti-Aβ antibody that binds the C-terminus of the modified APP of the invention or variant thereof that is exposed after gamma-secretase mediated cleavage at the Aβ40 gamma-secretase cleavage, e.g., G2-10, and an anti-Aβ antibody that binds the C-terminus of the modified APP of the invention or variant thereof that is exposed after gamma-secretase mediated cleavage at the Aβ42 gamma-secretase cleavage, e.g., G2-11.

In another aspect of this embodiment, the level Aβ secreted by the cells is measured by Western Blot, using antibodies anti-Aβ antibodies. In a specific embodiment, the anti-Aβ antibody is one that binds the C-terminus of the modified APP of the invention or variant thereof that is exposed after gamma-secretase mediated cleavage at the Aβ40 gamma-secretase cleavage, e.g., G2-10 antibody. In another specific embodiment, the anti-Aβ antibody is one that binds the C-terminus of the modified APP of the invention or variant thereof that is exposed after gamma-secretase mediated cleavage at the Aβ42 gamma-secretase cleavage, e.g., G2-11 antibody. In a more specific embodiment, the assay comprises an anti-Aβ antibody that binds the C-terminus of the modified APP of the invention or variant thereof that is exposed after gamma-secretase mediated cleavage at the Aβ40 gamma-secretase cleavage, e.g., G2-10, and an anti-Aβ antibody that binds the C-terminus of the modified APP of the invention or variant thereof that is exposed after gamma-secretase mediated cleavage at the Aβ42 gamma-secretase cleavage, e.g., G2-11.

In another aspect of this embodiment, the level of Aβ secreted by the cells is measured by mass spectrometry/surface enhanced laser desorption/ionization time-of-flight analysis (SELDI-TOF).

In a specific embodiment, the modified APP of the invention or variant thereof comprises a modification to at least one amino acid in the gamma-secretase inhibitory domain. In an aspect of this embodiment, said modification comprises a deletion of at least one amino acid in the gamma-secretase inhibitory domain. In a specific aspect of this embodiment, the entire gamma-secretase inhibitory domain is deleted. In another aspect of this embodiment, said modification comprises a substitution of at least one amino acid in the gamma-secretase domain. In a specific aspect of this embodiment, one or both of amino acid residues 19 and 20 of the gamma-secretase inhibitory domain comprise an amino acid that is not phenylalanine. In another specific aspect of this embodiment, at least one amino acid in the gamma-secretase inhibitory domain is substituted, including an embodiment in which each amino acid in the gamma-secretase inhibitory domain is substituted, whereby amino acid residue 17 is not leucine, amino acid residue 18 is not valine, amino acid residue 19 is not phenylalanine, amino acid residue 20 is not phenylalanine, and amino acid residue 21 is not alanine.

In another specific embodiment, the modified APP of the invention or variant thereof comprises the amino acid sequence of any one of SEQ ID NO: 6, 7, 8, 9, 10, 11, 18, 19, and 20 (specifying S1, S4, S5, S6, βCTFΔ, C100F19A (phenylalanine at 19 mutated to alanine), C100F20A, and C100F19AF20A). In a specific embodiment, the modified APP of the invention is APP695 comprising a modification in the gamma-secretase inhibitory domain.

6.4 Screens for Gamma-Secretase Inhibitors
6.4.1 ECL Assay Using Aβ Peptides for Identifying Gamma-Secretase Inhibitors In one embodiment, a method for the identification or validation of a gamma-secretase inhibitor comprises the ECL assay of Aβ peptides, wherein said method comprises: (a) contacting a candidate compound which is a potential gamma-secretase inhibitor with a modified APP of the invention or variant thereof and a source of gamma-secretase; (b) incubating said potential gamma-secretase inhibitor, said modified APP of the invention or variant thereof and said source of gamma-secretase for a time period sufficient for gamma-secretase activity to take place; (c) adding an anti-Aβ ruthenylated antibody; and (d) detecting a γ-secretase product by a product-specific ruthenylated antibody using ECL. Using this assay, a candidate compound is identified or validated as a gamma-secretase inhibitor if the activity of gamma-secretase toward the modified APP of the invention or variant thereof is decreased relative to the activity of gamma-secretase toward the modified APP in the absence of the gamma-secretase inhibitor.

In a specific embodiment, the source of gamma-secretase activity is a cell membrane, e.g., a HeLa cell membrane, and the incubation of step (b) takes place in the presence of a detergent, e.g., CHAPSO (0.25%).

In another specific embodiment, the anti-Aβ antibody is one that binds the C-terminus of the modified APP of the invention or variant thereof that is exposed after gamma-secretase mediated cleavage at the Aβ40 gamma-secretase cleavage, e.g., the G2-10 antibody described in Li, et al., 2000, *Proc. Natl. Acad. Sci. USA* 97:6138-6143. In another specific embodiment, the anti-Aβ antibody is one that binds the C-terminus of the modified APP of the invention or variant thereof that is exposed after gamma-secretase mediated cleavage at the Aβ42 gamma-secretase cleavage, e.g., the G2-11 antibody described in Yin, et al., 2007, *J. Biol. Chem.* 282:23639-23644. In a more specific embodiment, the assay comprises an anti-Aβ antibody that binds the C-terminus of the modified APP of the invention or variant thereof that is exposed after gamma-secretase mediated cleavage at the Aβ40 gamma-secretase cleavage, e.g., the G2-10 antibody, and an anti-Aβ antibody that binds the C-terminus of the modified APP of the invention or variant thereof that is exposed after gamma-secretase mediated cleavage at the Aβ42 gamma-secretase cleavage, e.g., the G2-11 antibody. In some embodiments, the anti-Aβ antibody is ruthenylated.

In another specific embodiment, the assay includes a source of beta-secretase.

In another embodiment, the modified APP comprises the amino acid sequence identified in SEQ ID NO: 9 (substrate S1 of Table 2), SEQ ID NO: 12 (substrate S4 of Table 2), SEQ ID NO: 13 (substrate S5 of Table 2), SEQ ID NO: 14 (substrate S6 of Table 2), SEQ ID NO:10 [.beta.-CTF.DELTA.], SEQ ID NO: 6 [modified APP695 substrate in which residues 613-617 are deleted (termed "modified APP695" herein)], mutated SEQ ID NO: 28 [the C-terminal fragment of APP in which residue Aβ 19 (F) is mutated to A (C100F19A)], mutated SEQ ID NO: 28 (C100F20A), or mutated SEQ ID NO: 28 (C100F19AF20A).

In another specific embodiment, the modified APP of the invention or variant thereof comprises the amino acid sequence of any one of SEQ ID NO: 6, 7, 8, 9, 10, 11, 18, 19, and 20 (specifying S1, S4, S5, S6, βCTFΔ, C100F19A (phenylalanine at 19 mutated to alanine), C100F20A, and C100F19AF20A).

In another specific embodiment, the modified APP of the invention or variant thereof demonstrates a kcat/Km greater than that of an unmodified APP.

6.4.2 Aβ HTRF Assay for Identifying Gamma-Secretase Inhibitors

In another embodiment, a method for the identification or validation of a gamma-secretase inhibitor assay for proteolytic cleavage by gamma-secretase at a site corresponding to positions 38, or 40, or 42 of Aβ (i.e., at Aβ38, Aβ40, or Aβ42) uses HTRF. This method includes steps of: (a) contacting a candidate compound that is a potential gamma-secretase inhibitor with a modified APP of the invention or variant thereof and a source of gamma-secretase; wherein said modified APP of the invention or variant thereof includes a detectable tag or label; (b) incubating said modified APP of the invention or variant thereof with said source of gamma-secretase for a time period sufficient for gamma-secretase activity to take place; (c) adding an HTRF detection mixture that includes (i) a first antibody that recognizes a gamma-secretase-cleaved peptide resulting from cleavage at the Aβ38, Aβ40, or Aβ42 gamma-secretase cleavage site but does not recognize uncleaved gamma-secretase substrates and (ii) a rare earth metal-labeled second antibody that binds the first antibody, and (iii) a fluorophore-conjugated reagent that binds to the detectable tag or label; (d) incubating said HTRF detection mixture with said modified APP of the invention or variant thereof and said source of gamma-secretase; and (e) measuring the cleavage of said modified APP of the invention or variant thereof by gamma-secretase using, generally, Fluorescence Resonance Energy Transfer ("FRET"), or more particularly, Homogeneous Time Resolved Fluorescence (HTRF), by exciting the rare earth metal and detecting fluorescence from the fluorophore of the conjugated reagent.

A candidate compound is identified or validated as a gamma-secretase inhibitor if the activity of gamma-secretase toward the modified APP of the invention or variant thereof is decreased relative to the activity of gamma-secretase toward the modified APP in the absence of the gamma-secretase inhibitor.

In a specific embodiment, the source of gamma-secretase is a cell or cell membrane, e.g., a HeLa cell or constituent membrane, and the incubation of step (b) takes place in the presence of a detergent, e.g., CHAPSO, at a concentration optimized for the assay.

In a specific embodiment, the antibody that recognizes gamma-secretase-cleaved peptides resulting from cleavage at the Aβ40 gamma-secretase cleavage site but does recognize uncleaved gamma-secretase substrates is the G2-10 antibody.

In another specific embodiment, the assay includes a source of beta-secretase.

In another specific embodiment, the modified APP of the invention or variant thereof comprises a modification to at least one amino acid in the gamma-secretase inhibitory domain. In an aspect of this embodiment, said modification comprises a deletion of at least one amino acid in the gamma-secretase inhibitory domain. In a specific aspect of this embodiment, the entire gamma-secretase inhibitory domain is deleted. In another aspect of this embodiment, said modification comprises a substitution of at least one amino acid in the gamma-secretase domain. In a specific aspect of this embodiment, one or both of amino acid residues 19 and 20 of the gamma-secretase inhibitory domain comprise an amino acid that is not phenylalanine. In another specific aspect of this embodiment, each amino acid in the gamma-secretase inhibitory domain is substituted, such that amino acid residue 17 is not leucine, amino acid residue 18 is not valine, amino acid residue 19 is not phenylalanine, amino acid residue 20 is not phenylalanine, and amino acid residue 21 is not alanine.

In another specific embodiment, the modified APP of the invention or variant thereof comprises the amino acid sequence of any one of SEQ ID NO: 6, 7, 8, 9, 10, 11, 18, 19, and 20 (specifying S1, S4, S5, S6, βCTFΔ, C100F19A (phenylalanine at 19 mutated to alanine), C100F20A, and C100F19AF20A).

In another specific embodiment, the modified APP of the invention or variant thereof demonstrates a kcat/km greater than that of an unmodified APP 6.4.3 Cell-Based Assays for Identifying Gamma-Secretase Inhibitors In another embodiment, a method for the identification or validation of a gamma-secretase inhibitor comprises a cell-based assay, wherein said assay comprises: (a) transfecting cells, in the presence of a source of gamma-secretase and a source of beta-secretase, with a plasmid containing the nucleotide sequence of a modified APP of the invention or variant thereof; (b) adding a potential gamma-secretase inhibitor; (c) incubating said cells and said potential gamma-secretase inhibitor for a time period sufficient for beta-secretase and gamma-secretase activity to occur; and (d) detecting Aβ secreted by the cells, wherein a gamma-secretase inhibitor is identified or validated if the activity of gamma-secretase toward the modified APP of the invention or variant thereof is decreased relative to the activity of gamma-secretase toward the modified APP in the absence of the gamma-secretase inhibitor.

In a specific embodiment, the cells provide the source of gamma-secretase and the source of beta-secretase. In another specific embodiment, the cells are HEK293 cells.

In one aspect of this embodiment, anti-Aβ antibodies that are specific for a C-terminal epitope of Aβ38, Aβ40, or Aβ42, are added to the cell conditioned media (containing secreted Aβ) and the level of Aβ secreted by the cells is measured by ECL. In a specific embodiment, the anti-Aβ antibody is one that binds the C-terminus of the modified APP of the invention or variant thereof that is exposed after gamma-secretase mediated cleavage at the Aβ40 gamma-secretase cleavage, e.g., G2-10 antibody. In another specific embodiment, the anti-Aβ antibody is one that binds the C-terminus of the modified APP of the invention or variant thereof that is exposed after gamma-secretase mediated cleavage at the Aβ42 gamma-secretase cleavage, e.g., G2-11 antibody. In a more specific embodiment, the assay comprises an anti-Aβ antibody that binds the C-terminus of the modified APP of the invention or variant thereof that is exposed after gamma-secretase mediated cleavage at the Aβ40 gamma-secretase cleavage, e.g., G2-10, and an anti-Aβ antibody that binds the C-terminus of the modified APP of the invention or variant thereof that is exposed after gamma-secretase mediated cleavage at the Aβ42 gamma-secretase cleavage, e.g., G2-11.

In another aspect of this embodiment, the level of Aβ secreted by the cells is measured by Western Blot, using anti-Aβ antibodies. In a specific embodiment, the anti-Aβ antibody is one that binds the C-terminus of the modified APP of the invention or variant thereof that is exposed after gamma-secretase mediated cleavage at the Aβ40 gamma-secretase cleavage, e.g., G2-10 antibody. In another specific embodiment, the anti-Aβ antibody is one that binds the C-terminus of the modified APP of the invention or variant thereof that is exposed after gamma-secretase mediated cleavage at the Aβ42 gamma-secretase cleavage, e.g., G2-11 antibody. In a more specific embodiment, the assay comprises an anti-Aβ antibody that binds the C-terminus of the modified APP of the invention or variant thereof that is exposed after gamma-secretase mediated cleavage at the Aβ40 gamma-secretase cleavage, e.g., G2-10, and an anti-Aβ antibody that binds the C-terminus of the modified APP of the invention or variant thereof that is exposed after gamma-secretase mediated cleavage at the Aβ42 gamma-secretase cleavage, e.g., G2-11.

In another aspect of this embodiment, the level Aβ secreted by the cells is measured by mass spectrometry/surface enhanced laser desorption/ionization time-of-flight analysis (SELDI-TOF).

In a specific embodiment, the modified APP of the invention or variant thereof comprises a modification to at least one amino acid in the gamma-secretase inhibitory domain. In an aspect of this embodiment, said modification comprises a deletion of at least one amino acid in the gamma-secretase inhibitory domain. In a specific aspect of this embodiment, the entire gamma-secretase inhibitory domain is deleted. In another aspect of this embodiment, said modification comprises a substitution of at least one amino acid in the gamma-secretase domain. In a specific aspect of this embodiment, one or both of amino acid residues 19 and 20 of the gamma-secretase inhibitory domain comprise an amino acid that is not phenylalanine. In another specific aspect of this embodiment, each amino acid in the gamma-secretase inhibitory domain is substituted, such that amino acid residue 17 is not leucine, amino acid residue 18 is not valine, amino acid residue 19 is not phenylalanine, amino acid residue 20 is not phenylalanine, and amino acid residue 21 is not alanine. In another specific embodiment, the modified APP of the invention or variant thereof comprises the amino acid sequence of any one of SEQ ID NO: 6, 7, 8, 9, 10, 11, 18, 19, and 20 (specifying S1, S4, S5, S6, βCTFΔ, C100F19A (phenylalanine at 19 mutated to alanine), C100F20A, and C100F19AF20A). In a specific embodiment, the modified APP of the invention is APP695 comprising a modification in the gamma-secretase inhibitory domain.

In a specific embodiment, the modified APP of the invention is APP695 comprising a modification in the gamma-secretase inhibitory domain.

6.5 Combinatorial Chemical Libraries

Assays for γ-secretase activity, using labeled or detectable APP-based substrates, are identified herein. As described above, and disclosed in several Examples below, these assays are adaptable for application in high throughput screens of candidate chemical compounds in a quest for inhibitors of γ-secretase activity. In many embodiments such assays are implemented in multiwell plates, including 96-well, 384-well, and 1536-well plates. Candidate compounds are provided for these screens from extended chemical libraries. Preparation of chemical libraries are widely known in the field. Combinatorial Approaches to introducing framework components as well as peripheral substituents have been developed, including techniques for tagging each synthesis so that intermediates and products are identified throughout the course of the synthesis. Other libraries are prepared from a broad range naturally occurring substances, and still others from assemblages of pharmaceutical agents already known to possess therapeutic effects or therapeutic potential for a broad range of medical indications. Nonlimiting examples of preparation and uses of chemical libraries, including combinatorial chemical libraries, include U.S. Pat. No. 7,083,812, entitled "Chemical library preparation method from natural product"; U.S. Pat. No. 6,936,477, entitled "Complex combinatorial chemical libraries encoded with tags"; U.S. Patent Application Publication 20090005256, entitled "Analysis of Encoded Chemical Libraries"; U.S. Pat. No. 6,800,444, entitled "Complex chemical libraries"; International publication WO/2006/102542, entitled "Diverse Chemical Libraries Bound To Small Particles With Paramagnetic Properties"; U.S. Pat. No. 6,625,546, directed to the direct identification of a chemical compound structure following solid phase synthesis of a chemical compound library; U.S. Pat. No. 6,625,546, directed to methods for using structural identification technology to increase the productivity of solid phase synthesis strategies; and "Designed chemical libraries for hit/lead optimization", Cooper T and Andrews-Cramer, K, Innovations in Pharmaceutical Technology, pp. 46-53 (www.iptonline.com/articles/public/IPTFIVE46NP.pdf).

6.6 Peptide Mimetics

7. EXAMPLES

The following examples should be seen as illustrative, and should not be viewed as limiting the scope of the present invention. Reasonable variations, such as those that occur to a reasonable artisan, can be made herein without departing from the scope of the present invention.

7.1 Experimental Procedures

7.1.1 Synthesis of Peptides

All peptides in this study were synthesized using standard Fmoc solid phase chemistry on a peptide synthesizer (Protein Technologies, Inc.). The same method was used to incorporate p-Benzoyl-L-phenylalanine (BPA; Bachem, Torrance, Calif.), a photoreactive amino acid, into peptide for affinity labeling. Peptides were cleaved from the resin and deprotected with cocktail reagents (trifluoroacetic acid:thioanisole:EDT:anisole, 90:5:3:2 where EDT signifies ethanedithiol). All peptides were purified by high-pressure liquid chromatography (HPLC) on a reverse-phase C18 column (ZORBAX 300 SB-C18 9.4 mmX 25 cm, Agilent Technologies). The identity of the peptides was verified by LC-MS/MS (Agilent Technologies).

7.1.2 Membrane Preparation and Photoaffinity Labeling

Membrane preparation and photoaffinity labeling were performed essentially as described (Li et al., 2000, *PNAS*, 97: 6138-6143) except 300 nM of photoactive peptide was used. The labeled proteins were eluted with 2×SDS sample buffer and analyzed with Western blotting using antibodies against the components of γ-secretase complex. Protein concentration was determined with the $D_c$ protein assay kit (Bio-Rad)

7.1.3 Expression of Biotinylated Recombinant Proteins

AviTag, a specific 15 residue peptide sequence (GLN-DIFEAQ<u>K</u>IEWHE (amino acids 1-15 of SEQ ID NO:11), the underlined K becomes labeled with biotin; Avidity, LLC; U.S. Patent Nos. 5,723,584, 5,874,239 & 5,932,433) that can be biotinylated with biotin ligase, was cloned into a pIAD16 vector (McCafferty et al., 1997, *Biochemistry*, 36: 10498-10505) (kindly provided by Professor Christopher Walsh, Harvard Medical School) to generate a pIAD16Avi plasmid. The APP fragments with the FLAG epitope tag (DYKD-DDDK (amino acids 99-106 of SEQ ID NO:11)) were inserted into the pIAD16Avi vector to provide a sequence for a chimeric maltose binding protein-thrombin target sequence-AviTag-APP fragment construct. For expression of biotinylated protein, pIAD16Avi-APP and pACYC164, which encodes biotin ligase were co-transformed in BL21 (DE3) *E. coli* cells. When bacterial growth reached an OD600 of 0.4-0.8, isopropyl 1-thio-β-D-galactopyranoside (IPTG, 100μM) was added to induce target protein expression in the presence of 50μM of biotin. Cells were pelleted and lysed by French press. The soluble fraction was subjected to amylose affinity chromatography through a maltose binding protein (MBP) tag. The purified protein was treated with thrombin at 16° C. overnight to cleave between MBP and AviTag. The biotinylation of target proteins was verified by LC-MS analysis.

7.1.4 In Vitro γ-Secretase Assay

The recombinant proteins were incubated with γ-secretase (40 μg/ml) in the presence or absence of 1 μM γ-secretase inhibitor L-685,458 (CAS [292632-98-5], shown below). The reaction mixture contains 0.25% 3[(3-cholamidopropyl) dimethylammonio]-2-hydroxypropanesulfonic acid (CHAPSO), 0.1 μg/μl BSA, protease inhibitor, 50 mM PIPES, pH 7.0, 5 mM MgCl$_2$, 5 mM CaCl$_2$ and 150 mM KCl. The reaction was incubated for 2.5 hr at 37° C. and stopped by adding RIPA buffer (150 mM NaCl, 1.0% NP-40, 0.5% sodium

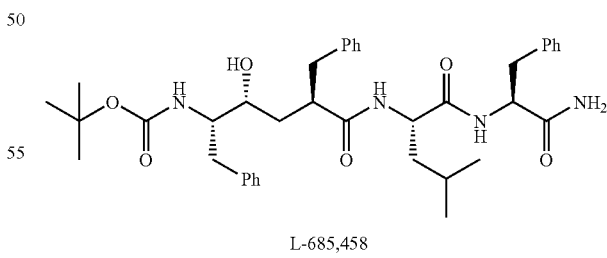

L-685,458 deoxycholate, 0.1% SDS, 50 mM Tris HCl, pH 8.0). The products were detected with various antibody combinations as previously described (Lai et al., 2003; *J. Biol. Chem.*, 278: 22475-22481; Li et al., 2000, *Proc. Natl. Acad. Sci. USA*, 97: 6138-6143; Yin et al., 2007, *J. Biol. Chem.*, 282:23639-23644) using electrochemiluminescence (ECL). The amount of product was determined using synthetic peptide or recombinant standards. The Km and Vmax were determined from the Michaelis-Menten equation Michaelis-Menten Kinetics (v=Vm[S]/(Km[S]); v: initial rate; Vm: maximum velocity; Km: the Michaelis-Menten constant, S: substrate). P-values were calculated from Student t-test.

7.1.5 Cell-Based Aβ Production Assay and Western Blot

HEK 293 cells (Clontech, Mountain View, Calif.) were cultured in Dulbecco's modified Eagle's medium (DMEM), supplemented with 10% fetal bovine serum and penicillin. HEK 293 cells stably transfected with APP were maintained in DMEM medium with 10% fetal bovine serum plus 1 μg/μl puromycin. When they reached 70% confluence of 6-well plates, the cells were transiently transfected with 20 ng of pmaxGFP (encoding green fluorescent protein; Amaxa, available from Lonza Cologne AG, Cologne, Germany) and 2 μg target plasmids as indicated in individual experiments. After transfection, fresh media with or without γ-secretase inhibitor were added to the cells. After 48 hours total incubation, conditioned cell media were collected and diluted in RIPA buffer. Secreted Aβ peptides were detected by ECL assay using biotinylated 6E10 monoclonal antibody (Covance, Princeton, N.J.; directed against Aβ1-16) or biotinylated 4G8 monoclonal antibody (Covance; directed against Aβ17-24) and ruthenylated G2-10 antibody (directed against the C-terminal epitope of Aβ40 that includes amino acid residues 31-40 of the human Aβ peptide; G2-10 does not bind to Aβ1-38, Aβ1-39, Aβ1-42, Aβ1-43 or Aβ1-44, nor to uncleaved substrate). Antibodies may be conjugated to ruthenium for use in ECL by reacting ruthenium (II)-tris(bipyridyl)-N-hydroxysuccinimide ester, dissolved in DMSO, with the antibody, for example at a molar ratio of about 7.5:1. After a suitable reaction time, such as 60 min., the reaction is terminated by adding L-lysine, and excess reagents drawn off by passing the mixture over a gel permeation column such as Sephadex G-25 (U.S. Patent Application Publication 20080317764). Conditioned media and cell lysates were analyzed by Western blotting using Karen antibody (αAPP; a polyclonal antiserum raised to the secreted amino terminus of APP; Steinhilb, Turner and Gaut, 2002; *J. Neurochem.* 80: 1019-1028), 6E10 and CT15 (Stephens and Austen, 1996 *J. Neurosci. Res.* 45: 211-225) antibodies (see FIG. 2A for diagrams of selected antibody recognition sites of APP fragments).

7.1.6 Analyses of Aβ Peptides in Conditioned Media by SELDI-TOF

HEK293 cells transfected with the APP construct were cultured for 48 hours in DMEM supplemented with 10% fetal bovine serum. Conditioned media were collected and 50 μl of the media were incubated overnight with preactivated SELDI protein chip PS20 coated with 6E10 antibody. The procedures of the amino-coupling of monoclonal antibody to SELDI protein chips and immunocapture were all performed as described by the manual of the ProteinChip β-amyloid Multipeptide Kit (Ciphergen Biosystems, Fremont, Calif.). Samples were analyzed on a PSB-II ProteinChip Array Reader (Ciphergen Biosystems) according to an automated data collection protocol. All spectra were calibrated externally using All-In-1 Peptide Standard II (Ciphergen) and normalized to the average intensity height of peak.

7.17 Immunoprecipitation and βCTF ECL assay

The mock (empty vector) or TACE transfected HEK293-APP cells (one well of 6-well plate each) were collected and lysed with 200 μl of RIPA buffer with a mixture of protease inhibitors. After rotating at 4° C. for an hour, cell lysates were centrifuged at 13K rpm for 5 minute and the supernatants were subjected to immunoprecipitation with W0-2 or 4G8 antibodies and blotted with varying antibodies. The mock or TACE transfected HEK293-APP cell lysate were also incubated with biotinylated 6E10, CT-15 and ruthenylated anti-rabbit secondary antibodies for 3 hrs, magnet streptavidin beads were then added and incubated for 30 min. The assay mixtures were analyzed by an ECL technology.

7.2. Example 1

α-Secretase Cleaved C-Terminal Fragment (αCtf) is a Poor Substrate of γ-Secretase In Vitro Cleavage of APP by α- or β-secretase appears to be required for γ-secretase-mediated processing. βCTF (β-secretase cleaved APP C-terminal fragment; SEQ ID NO:8) has been widely utilized to detect γ-secretase activity in cell-based and in vitro assays (Li et al., 2000, *Proc. Natl. Acad. Sci. USA*, 97:6138-6143; Lichtenthaler et al., 1999, *FEBS Letters* 453: 288-292; Shearman et al., 2000, *Biochemistry*, 39:8698-8704). Shah et al., 2005, found that β-secretase cleavage of APP exposes the N-terminus of βCTF which is then recognized by nicastrin and brought to the active site for proteolysis (Shah et al., 2005, *Cell*, 122:435-447). However, whether αCTF, the α-secretase cleaved APP C-terminal fragment, shares the same mechanism as βCTF is not known. To compare their reactivity with γ-secretase, recombinant Actf (SEQ ID NO:7) and βCTF were overexpressed as maltose binding protein (MBP) fusion proteins with a thrombin cleavage site (FIG. 2A). Affinity-purified fusion proteins were treated with thrombin and analyzed by SDS-PAGE (FIG. 2B). The molecular mass of αCTF-FLAG and βCTF-FLAG was confirmed by LC-MS (FIG. 2C). The measured molecular masses of αCTF-FLAG and βCTF-FLAG were 10,621 and 12,557, respectively, and matched the calculated mass 10,617 and 12,554.

Each substrate at three concentrations was incubated with HeLa membrane in the presence and absence of 1 μM L-685, 458, a potent γ-secretase inhibitor (Shearman et al., 2000, *Biochemistry*, 39:8698-8704). The signal difference between L-685,458 treated and untreated samples is attributed to γ-secretase activity. The product resulting from γ-secretase cleavage of βCTF between the positions corresponding to Aβ40 and Aβ41 (X40; see FIG. 1) to provide a γCTF was detected by a pair of antibodies: biotinylated 4G8 and ruthenylated G2-10. Surprisingly, the two substrates, αCTF-FLAG and βCTF-FLAG, exhibit striking differences in their ability to be processed by γ-secretase. The rate of γ-secretase hydrolysis of βCTF-FLAG is 12-fold greater than for hydrolysis of αCTF-FLAG (FIG. 2D). Insight into the reaction mechanism of γ-secretase for processing of αCTF and βCTF is needed to understand how these two APP processing pathways are executed and regulated.

7.3. Example 2

An Inhibitory Domain (Aβ17-23) within the APP Substrate Regulates γ-Secretase Activity In Vitro A deletion strategy was applied to map motifs that regulate αCTF processing by γ-secretase. Because deletion of the N-terminus destroys the 4G8 antibody binding epitope upon which these assay depend, an AviTag was introduced into the N-terminus of APP CTFs. AviTag, a specific 15 residue peptide, serves as a substrate for biotin ligase that specifically catalyzes an attachment of biotin to the lysine residue within the AviTag. By biotinylating these recombinant proteins, γ-secretase activity could be directly monitored using only streptavidin beads and the G2-10 antibody. To facilitate protein isolation, an MBP/thrombin site was inserted ahead of the AviTag on these target proteins. First, this strategy was tested by directly fusing the transmembrane domain of APP (beginning at position Aβ28; see Thinakaran and Koo) behind the MBP/thrombin-AviTag. A target protein was co-expressed with biotin ligase in the presence of biotin and after purification, the fusion protein was treated with thrombin to liberate biotinylated transmembrane domain.

The biotinylated APP transmembrane domain, which is hereafter referred to as S1 (SEQ ID NO:9), was confirmed by LC-MS analysis. The S1 peptide was incubated with HeLa membrane and the Aβ40-site specific cleavage was detected using the G2-10 antibody. γ-Secretase effectively cleaved the S1 substrate (Table 2).

In order to investigate this question further, two additional substrates were constructed, S2 and S3 (Table 2), which both contain the Aβ17-27 sequence immediately N-terminal to the beginning of the transmembrane domain; S3 is prepared also to include the C-terminal tail of APP. Very little Aβ40-site specific γ-secretase product was detected using either the S2 or the S3 substrates (Table 2), suggesting that a motif which negatively regulates γ-secretase activity may reside in the sequence of Aβ17-27. Through a series of deletion experiments, it was found that S4 (SEQ ID NO:12), a substrate lacking seven amino acids (LVFFAED, Aβ17-23; SEQ ID NO:18), is effectively processed by γ-secretase with a rate similar to that of the S1 substrate (Table 2). These findings demonstrate that in synthetic peptide substrates of γ-secretase, the portion of Aβ peptides that includes Aβ17-23 strongly inhibits the activity of γ-secretase on the substrates.

NO:11) led to the generation of an inactive substrate. This finding indicates that the Aβ1-16 sequence may play a specific role in modulating the inhibitory effect of Aβ17-23 since βCTF is a substrate of γ-secretase. To examine the relationship of Aβ1-16 and Aβ17-23, four Aβ1-16 derived peptides were synthesized, including Aβ1-16, Aβ1-7, Aβ1-12 and Aβ8-16, and their effect on γ-secretase activity for processing of the S3 substrate was tested. Combinations of three concentrations (0.1, 1 and 10 μM) of Aβ1-16, Aβ1-7, Aβ1-12 or Aβ8-16 and three S3 concentrations (0.5, 1 and 2 μM) were used to test two peptide motifs in trans (acting from a different molecule) for γ-secretase activity. There is no difference among all of these combinations, i.e. little Aβ40-site specific γ-secretase product was detected. These studies suggest that the Aβ1-16 sequence only works in cis (i.e., acting when incorporated within the same molecule) in coordinating with Aβ17-23 for regulation of γ-secretase activity, but not when present in a mixture as a separate molecule.

In order to examine the role of Aβ17-23 in the βCTF substrate, a substrate (βCTFΔ; SEQ ID NO:25) was generated, in which this inhibitory domain is deleted (FIG. 3A). The γ-secretase cleaved products (Aβ40 and Aβ40Δ) from βCTF and βCTFΔ were detected by a pair of antibodies: 6E10 and G2-10. As a control, it was shown using synthetic stan-

TABLE 2

Sequences of various C-terminal substrates for γ-secretase activity

| Substrate/ SEQ ID NO: | Sequence | γ-secretase activity % |
|---|---|---|
| S1/9 | AviTag-KGAIIGLMVGGVVIATVIVITLVMLKKK | 100 ± 4.2 |
| S2/10 | AviTag-LVFFAEDVGSNKGAIIGLMVGGVVIATVIVITLVMLKKK | None |
| S3/11 | AviTag-LVFFAEDVGSNKGAIIGLMVGGVVIATVIVITLVMLKKKQYTSIHHGVVEVDAAVTPEERHLSKMQQNGYENPTYKFF EQMQN-FLAG | None |
| S4/12 | AviTag-VGSNKGAIIGLMVGGVVIATVIVITLVMLKKKQYTSIHHGVVEVDAAVTPEERHLSKMQQNGYENPTYKFF EQMQN-FLAG | 125 ± 6.2 |
| S5/13 | AviTag-YEVHHQKVGSNKGAIIGLMVGGVVIATVIVITLVMLKKKQYTSIHHGVVEVDAAVTPEERHLSKMQQNGYENPTYKFF EQMQN-FLAG | 85 ± 2.9 |
| S6/14 | AviTag-VAGAGGNVGSNKGAIIGLMVGGVVIATVIVITLVMLKKKQYTSIHHGVVEVDAAVTPEERHLSKMQQNGYENPTYKFF EQMQN-FLAG | 108 ± 5.2 |

AviTag represents the biotinylation sequence GLNDIFEAQKIEWHE.
FLAG represents the epitope tag DYKDDDDK γ-secretase activity is monitored by in vitro γ-secretase activity assay The critical question to address was whether the high reactivity of the S4 substrate was caused by shortening of the N-terminal portion of this γ-secretase substrate, or caused by a sequence specific effect. Therefore, two constructs, S5 and S6 (SEQ ID NOS:13 AND 14, respectively), were designed (Table 2). The Aβ17-23 sequence of S3 was replaced by Aβ10-16 (YEVHHQK (amino acids 1-7 of SEQ ID NO:13)) in S5 (effectively deleting Aβ17-23) or a random sequence (VAGAGGN amino acids 17-23 of SEQ ID NO:26)) in S6 (substituting non-Aβ residues in place of Aβ17-23). It was found that both S5 and S6 are remarkably active (Table 2). Their rates of γ-secretase-catalyzed proteolysis for S5 and S6 were 0.85- and 1.1-fold of those of S1, respectively. This observation strongly suggests that it is specifically the amino acid sequence of Aβ17-23 that directly regulates γ-secretase activity, rather than an effect being mediated by shortening of the N-terminal portion of the substrate.

Another observation is that replacement of the Aβ1-16 sequence with the 15-mer AviTag in S3 polypeptide SEQ ID dard peptides that Aβ40 and Aβ40Δ displayed the same reactivity to the antibodies. Kinetic analyses were conducted in order to compare the reactivity of βCTF and βCTFΔ with γ-secretase. Using ECL detection, the apparent Km is 0.47±0.09 μM for βCTF and 0.26±0.09 μM for βCTFΔ. Vmax values are 16±1 and 215±24 min$^{-1}$ μg$^{-1}$ for βCTF and βCTFΔ, respectively (FIG. 3B). The Vmax/Km or kcat/Km value for βCTFΔ, which indicates the catalytic efficiency of the enzyme, is 42-fold greater than for the βCTF substrate. In other words, βCTFΔ is a 42-fold better substrate than βCTF for γ-secretase proteolysis. These studies conclusively demonstrate that removal of this inhibitory domain significantly enhances substrate reactivity with γ-secretase.

It was next determined whether γ-secretase from other sources has the same preference for the βCTFΔ substrate. Cell membrane from mouse brain was isolated and its γ-secretase activity was assayed for the Aβ40- and Aβ42-site cleavages. Product formation was monitored by G2-10 and G2-11 antibodies, respectively. In mouse brain membrane, the reaction rate of γ-secretase for the hydrolysis of βCTFΔ is 25- and 11-times faster for the 40-site and 42-site production compared to βCTF substrate, respectively (FIG. 3C). In addition, the γ-secretase activity was assayed for Aβ38 production and ε-cleavage (FIGS. 3D and 3E). The Aβ38-site cleavage was detected with a combination of biotinylated 6E10 and ruthenylated anti-Aβ38 antibodies. The rate of γ-secretase activity for Aβ38 production from βCTFΔ increased as much as 10-fold over that for βCTF (FIG. 3D). However, the deletion of this domain has no effect on the ε-cleavage (AICD=APP intracellular domain) (FIG. 3E). These studies indicate that the removal of the inhibitory Aβ17-23 domain has distinctive effects on Aβ species (Aβ38, Aβ40 and Aβ42) and AICD.

7.4. Example 3

Peptides Derived from the Inhibitory Domain Directly Bind to Presenilin-1 (PS1) and Nicastrin In order to elucidate the role of the inhibitory domain in regulation of γ-secretase activity, the LVFFAED peptide (Aβ17-23; SEQ ID NO:18) was synthesized and its activity as an inhibitor of γ-secretase tested. This peptide exhibits inhibitory activity against γ-secretase activity on both APP (FIG. 4A) with an IC50 of 1.5 μM on APP cleavage. Furthermore, double reciprocal (Lineweaver-Burke) analyses showed the plots of the Aβ17-23 peptide intersect to the left of the X-axis (FIG. 4B), which indicates non-competitive inhibition, whereas the corresponding plots for L-685,458 intersect on the Y-axis (not shown), which is indicative of competitive inhibition and is consistent with a previous report (Yin et al., 2007, $J.\ Biol.\ Chem.$, 282:23639-23644). This result indicates that the Aβ17-23 heptapeptide does not interact with the active site of γ-secretase. To define the core sequences of this peptide necessary for γ-secretase inhibition, a series of peptides with truncations or additions at the N- and C-termini were synthesized (FIG. 4C). First, deletion of two charged residues from the C-terminus augmented the inhibitory potency (lines 1 and 2). However, removal of an additional Ala residue resulted in approximately 6-fold reduction in inhibitory potency (line 3). Second, addition of a residue at the N-terminus or C-terminus reduced its inhibitory potency as well (lines 4 and 5). Taken together, the close potencies exhibited by LVFFA (SEQ ID NO:19) and LVFFAED suggest that Aβ17-21 is the major determinant for inhibitory activity and that the two additional residues Aβ22-23 provide little contribution to its activity.

The potency of the LVFFAED peptide on γ-secretase cleavage of Notch substrate was also determined. The cleaved Notch product was detected by Val1744 antibody that specifically recognizes the product cleaved between Gly1743 and Val1744. The IC50 value of this peptide is 10 μM for Notch substrate processing (FIG. 4A). Despite the finding that the potency of this peptide is 6-fold less potent in the proteolytic cleavage of Notch by γ-secretase than that of APP-derived substrates, this study suggests that this inhibitory peptide is capable of inhibiting γ-secretase activity directed to both APP and other substrates. A peptide with amino acid sequence VKSEPVEPPL that is equivalent to the N-terminal residues of Notch extracellular truncation (NEXT) resulting from S2 cleavage by TACE (Tumor necrosis factor-α converting enzyme) or other metalloproteases (Selkoe and Kopan, 2003, $Ann.\ Rev.\ Neurosci.$, 26:565-597) was synthesized and its activity was tested. This S2-site derived Notch peptide did not inhibit γ-secretase for APP or Notch processing (data not shown).

To elucidate the interaction site between the γ-secretase complex and the inhibitory peptide, a photoaffinity labeling approach was employed by incorporating p-benzoylphenylalanine (BPA), a photoreactive unnatural amino acid, into the inhibitory peptides. Since the core region contains two phenylalanines (Phe) that structurally resemble BPA, these two residues were primarily targeted, and in order to facilitate peptide synthesis, purification and solubility, Aβ22-23 was included in these photoreactive probes. Replacement of phenylalanine at position 19 of Aβ17-23 with BPA (Aβ17-23BPA[19]) resulted in reduced inhibitory activity by 3-fold (FIG. 4C, line 6). However, substituting BPA into the Phe at position 20 (Aβ17-23BPA[20]) led to a 19-fold increase in potency with an IC50 of 81 nM (line 6. In order to monitor and retrieve labeled proteins, a biotin tag was conjugated to Aβ17-23BPA[20]. Moreover, attaching the biotin moiety at the C-terminus (Aβ17-23BPA[20]-biotin), as opposed to the N-terminus, was shown to have no effect on the peptide inhibition potency (IC50 of 83 nM, line 7). Therefore, this peptide (Aβ17-23BPA[20]-biotin) allowed for the probing of the interaction between the inhibitory peptides and γ-secretase.

HeLa membrane was incubated with Aβ17-23BPA[20]-biotin in the presence of 0.25% CHAPSO, and then irradiated at 350 nm. After the photolyzed membranes were solubilized, biotinylated proteins were captured, eluted and analyzed by western blotting with antibodies against biotin, PS1, nicastrin, PEN-2 and APH-1. Anti-biotin blotting reveals two major bands with molecular weights around 20 kDa and one minor band at approximately 32 kDa, which are absent in the presence of added unphotolyzed nonbiotinylated peptide to compete for the antibody (FIG. 4D). Subsequent analyses showed that these bands co-migrated with PS1-CTF and PS1-NTF (FIG. 4D). In addition, Aβ17-23BPA[20]-biotin labels nicastrin (FIG. 4D), but not PEN-2 or APH1a (both PEN-2 and APH1a were detected from directly-loaded cell membrane proteins as indicated by an arrow in the right lane of blot). (The remote possibility that covalent attachment of this compound masked the epitopes of both antibodies cannot be eliminated.) All of these photochemical labelings were blocked with an excess of non-biotinylated Aβ17-23BPA[20] (FIG. 4D), suggesting that addition of a biotin moiety did not alter the specificity of this probe.

Next, the inhibitory capacity of Aβ17-21 and Aβ17-23 in blocking the cross-linking of Aβ17-23BPA[20]-biotin was determined. Both peptides at 25 μM were found to inhibit photoinsertion of this probe (FIG. 4E, lower panel), whereas Aβ17-21 and Aβ17-23 at 10 μM suppressed the photolabeling by approximately 77% and 53%, respectively. These studies suggest that the incorporation of BPA and biotin into the LVFFAED peptides enhanced its potency, but did not alter its specificity. Furthermore, the LVFFA (SEQ ID NO:19) peptide appears to be more effective than the LVFFAED (SEQ ID NO:18) peptide in blocking photoinsertion, which is consistent with the inhibitory potency of both peptides. Therefore, these data suggest that Aβ17-21 is the core region of the inhibitory domain and its peptide binding pocket in the γ-secretase complex is composed of at least PS1-CTF, PS1-NTF and nicastrin. Lastly, the relationship between the inhibitory domain binding site and other γ-secretase inhibitor interacting sites (FIG. 4F) was examined. Both L-685,458 and compound E completely blocked the photo-crosslinking of PS1-CTF and PS1-NTF by Aβ17-23BPA[20]-biotin. These observations further validate that this peptide incorporating the inhibitory domain identifies in these Examples specifically interacts with γ-secretase and the binding sites for L-685,458 or compound E either partially overlap or allosterically change the inhibitory domain binding pocket.

7.5 Example 4
A Retro-Inverso Peptide of the Inhibitory Domain Selectively Suppresses Cellular γ-Secretase Activity for APP Processing After confirming in vitro activity of inhibitory domain-derived peptides, we tested whether they were capable of inhibiting cellular γ-secretase activity. After transfection or compound treatment, conditioned cell media were collected and diluted in RIPA buffer. Secreted Aβ peptides were detected by ECL assay using biotinylated 6E10 and ruthenylated G2-10 antibodies. Initial tests using the LVFFAED peptide up to 100 μM failed to inhibit cellular γ-secretase activity (data not shown).

We therefore synthesized modified peptides that increase cell permeability and/or resistance to proteolytic degradation and tested their activity. Both side chains of Glu (E) and Asp (D) in PM-1 were converted to methyl esters and the C-terminus was amidated (SEQ ID NO:23; FIG. 5a). PM-1 inhibited γ-secretase activity with an IC50 of 2 μM in vitro (FIG. 5b). It is worth noting that PM-1 was as active as the parent peptide, suggesting that the charges in these residues (Asp-Glu) have marginal contribution to its inhibitory potency, which is consistent with results presented above. However, PM-1 was unable to suppress cellular γ-secretase activity up to 100 μM (data not shown).

RI-PM-1 is a retro-inverso (RI) form of PM-1 (SEQ ID NO:24). RI peptides are comprised of D-amino acids assembled in the reverse order from the parent L-peptide and possess similar topographies as the original L-peptide, yet are more resistant to proteolysis. RI-PM-1 exhibits reduced in vitro inhibitory potency with an IC50 of 18 μM compared to PM-1 (FIG. 5b). Importantly, it completely inhibits photoinsertion of Aβ17-23BPA20-biotin into PS1-NTF (FIG. 5b inset), suggesting that this RI transformation does not alter the specificity of this peptide. Furthermore, it reduces secreted Aβ species in a dose dependent manner (FIG. 5c) in our cellular model and concomitantly caused an accumulation of APP-CTFs (FIG. 5c). Taken together, these results indicate that RI-PM-1 inhibits cellular γ-secretase activity for APP processing through interaction with an inhibitory EI site.

Another critical question is whether targeting this EI site can lead to the development of specific inhibitors for APP processing that do not affect cleavage of other substrates. We therefore examined the effect of RI-PM-1 on Notch1 processing. HEK293 cells were transfected with the ΔE-Notch1 construct in which the majority of the Notch1 extracellular domain is removed and thereby is already "primed" for γ-secretase cleavage 25. The expression of ΔE-Notch1 protein was confirmed with anti-Myc antibody (FIG. 5e, upper panel). The ΔE-Notch1 expressing cells were treated with RI-PM-1 and the cleaved NICD product was detected using SM320, a specific antibody that recognizes the N-terminus of the cleaved product but not the uncleaved substrate. RI-PM-1 used at a concentration up to 100 μM does not reduce the production of NICD (FIG. 5e, lower panel), whereas it inhibits the production of Aβ by 70% (see FIG. 5c) at this concentration. Moreover, NICD was not detected in L-685,458 treated samples (FIG. 5e, lane 1, lower panel) demonstrating the specificity of the cleavage assay for monitoring γ-secretase Notch1 processing. Clearly, RI-PM-1 exhibits selectivity against γ-secretase for APP over Notch1 processing. Therefore, the EI site could offer a new drug target site for the development of selective γ-secretase inhibitors for APP.

7.6. Example 5
Mutation of the Inhibitory Domain within βCTF Leads to a Significant Increase in Secreted Aβ from Cells After establishing that the Aβ17-21 inhibitory domain regulates γ-secretase activity in vitro, it was determined whether a similar effect could be observed in cells. In order to assess the effect of the inhibitory domain on cellular γ-secretase activity, a simplified system developed by Lichtenthaler et al. (Lichtenthaler et al., 1999, FEBS Letters, 453:288-292) in which an SPA4CT construct consisting of an N-terminal signal peptide (SP) was applied. In this procedure, A4CT (equivalent to βCTF) is used in this Example to monitor γ-secretase activity on various substrates. After the signal peptide is removed by signal peptidase during membrane insertion, the product βCTF (A4CT) becomes a substrate of γ-secretase (Lichtenthaler et al., 1999, FEBS Letters, 453:288-292). Therefore, this system eliminates the need for β-secretase cleavage, a rate-limited step for APP processing and Aβ production, thereby allowing one to accurately measure cellular γ-secretase activity.

Two mutation constructs that are analogous to the S4 and S6 substrates in Table 2 were made. In these substrates, the Aβ17-23 sequence is either deleted (βCTFΔ) or replaced by the sequence VAGGGAN (βCTFmut; amino acids 17-23 of SEQ ID NO:26), as diagrammed in FIG. 6A, which shows that the peptides in question were also prepared with signal peptide (SP). After transiently expressing SPβCTF, SPβCTFΔ, or SPβCTFmut in HEK293T cells for 24 hours, the expression of substrate in cell lysates was analyzed by western blotting, and the secretion of Aβ into conditioned media was determined by ECL. It was shown that the same amount of protein from cell lysates was separated by SDS-PAGE upon western blotting using the CT-15 antibody which recognizes the C-terminal fragment (CTF) of APP (FIG. 6B). The equal band intensities for these peptides indicates that the same amount of substrate was present in these cells. The amount of secreted Aβ40 from the SPβCTFΔ or SPβCTFmut-transfected cells is 10 or 4.5-fold higher than from the SPβCTF-cells incorporating the wild type fragment (FIG. 6C). These results further validate that the Aβ17-23 inhibitory domain plays a critical role in the regulation of γ-secretase.

The ability of the inhibitory domain to reduce the negative regulation of APP processing and therefore increase substrate reactivity in vitro was tested. The S3 substrate (Table 2) was pre-incubated with the monoclonal antibody 4G8 which binds directly to the LVFFAE epitope and should therefore "mask" the inhibitory domain (diagrammed in FIG. 6D). The assay background was defined in the presence of L-685,458 (FIG. 6D). After subtracting the L-685,458 defined background, a 26-fold increase in γ-secretase activity with the 4G8 antibody-bound substrate was found (FIG. 6D). Therefore, the data show that either masking or mutating the inhibitory domain interferes with its inhibitory role and results in an increase in γ-secretase cleaved products. In contrast, a previous study showed that the binding of anti-FLAG antibody to the nFLAG-C99 (equivalent to βCTF) blocked γ-secretase cleavage of this substrate (Shah et al., 2005, *Cell*, 122:435-447). These studies suggest that this inhibitory domain and the N-terminal fragment of βCTF play disparate roles in regulating γ-secretase activity for APP processing.

7.7. Example 6
α-Secretase Cleaved C-Terminal Product (αCTF) Inhibits γ-Secretase Activity The present findings have shown that αCTF is a poor substrate of γ-secretase and that the Aβ17-21 peptide is an inhibitor of protease activity, suggesting that αCTF could suppress γ-secretase activity through α-secretase cleavage resulting in the exposure of the inhibitory domain. An attempt to express αCTF in cells to test its activity was undertaken. However, despite extensive attempts with various transfection conditions, no αCTF protein was detected when the αCTF gene was fused with the APP signal sequence in the same manner as the expression of βCTF above. Therefore, an alternative means to address this issue was explored. Both ADAM10 and TACE (Tumor necrosis factor-α converting enzyme; GenBank Acc. No. NM_003183) TACE have been found to exhibit α-secretase activity (Buxbaum et al., 1998, *J. Biol. Chem.*, 273:27765-27767; Kojro and Fahrenholz, 2005, *Subcell. Biochem.*, 38:105-127). Since the gene encoding the full length of human ADAM10 is sometimes subject to recombination, TACE was chosen for these studies. Nonetheless, the expression of TACE or ADAM10 should be able to promote αCTF production and address the issue. TACE was expressed fused with a C-terminal HA tag in the HEK293-APP cells and its effect on APP695 processing was examined. TACE protein expression was first confirmed by western blot analysis using an anti-HA antibody (FIG. 7A, upper panel). The expression of TACE had only a moderate effect (15% reduction) on the level of APP (FIG. 7A, middle panel; note the diagram of this experiment). Equal protein loading was confirmed by anti-β tubulin western blotting (FIG. 7A, lower panel).

The secreted APP species that include sAPPα, sAPPβ and Aβ in conditioned media were analyzed next. sAPPα and sAPPβ (SEQ ID NOS:4 and 5, respectively) which refer to the liberated N-terminal fragments of APP resulting from the proteolytic cleavages by α-secretase and β-secretase, are specifically recognized by the 6E10 and anti-sAPPβ antibodies, respectively (diagrammed in FIG. 7B). Elevated sAPPα levels were found upon action by TACE, indicating that the transiently expressed TACE mediates α-secretase-like processing of APP processing (FIG. 7B). Furthermore, reduced sAPPβ suggested that there was less substrate available for β-secretase (FIG. 7B), which is a consequence of TACE mediated depletion of the APP substrate. This finding is consistent with previous reports of competition between α-secretase and β-secretase for the APP substrate (Nitsch et al., 1992, *Science*, 258:304-307; Postina et al., 2004, *J Clin Invest*, 113:1456-1464; Skovronsky et al., 2000, *J. Biol. Chem.*, 275: 2568-2575).

The level of secreted Aβ40 with 6E10 and G2-10 antibodies was determined next. The amount of Aβ40 that is derived by β- and γ-secretase cleavages was significantly reduced, by 82%, following TACE overexpression (FIG. 7C), which is consistent with previous results seen in ADAM10-mouse studies (Postina et al., 2004, *J. Clin. Invest.*, 113:1456-1464). However, when the total amount of γ-secretase-cleaved products known as X40 including Aβ and P3 (FIG. 1) was examined, up-regulation of TACE activity also resulted in a 53% reduction of X40 (FIG. 7C). This finding, showing that higher α-secretase activity leads to a reduction of total γ-secretase activity, suggests that αCTF acts as an endogenous inhibitor of γ-secretase.

As a further test of this hypothesis, the effect of TACE expression on cellular αCTF and βCTF fragments was examined. First, cell lysates were immunoprecipitated (IPI) with the 4G8 antibody and western blotted (WB) with the CT15 antibody (FIG. 7D, upper panel). Clearly, the expression of TACE augmented the production of αCTF, which is consistent with the increase in secreted sAPPα. In contrast to sAPPβ, βCTF was increased. In order to reduce the interferences of αCTF for βCTF quantification, βCTF was immunoprecipitated with W0-2 antibody and probed with W0-2 and FCA-18 antibodies. FCA-18 specifically recognizes the β-secretase cleaved N-terminus of βCTF and W0-2 binds to the Aβ1-16 fragment. Both blots (FIG. 7D, middle and low panels) showed that the expression of TACE led to increased βCTF species (2-fold by FCA-18 and 4-fold by W0-2), rather than a reduction. A reduction in βCTF would be predicted from the substrate competition model. Furthermore, βCTF was directly detected from cell lysates with 6E10 and CT-15 antibodies using ECL technology and it was demonstrated that the level of β-CTF in the TACE-expression cells is approximately 2.5 fold higher than that in the control cells (FIG. 7E). Taken together, these observations indicate that increased α-secretase activity caused an accumulation of βCTF in cells despite a reduction in sAPPβ, and support our hypothesis that αCTF negatively regulates γ-secretase activity for Aβ and P3 production (FIG. 7F).

In order to further test the hypothesis that αCTF indeed inhibits γ-secretase, a cell-free system was applied to address these issues. The in vitro γ-secretase activity for the production of X40 was examined in the presence of both the βCTF and αCTF substrates (FIG. 8A). The effect of αCTF on γ-secretase activity in the cell-free system is analogous to the results from the cellular studies. αCTF at 0.25, 0.5 and 1.0 μM significantly suppresses γ-secretase activity for Aβ production by 66, 71 and 82% whereas it inhibits X40 production by 24, 32, and 60% respectively (FIG. 8A). In order to verify that the inhibitory domain within αCTF contributes to this inhibition, the γ-secretase activity was determined in the presence of both the βCTF and the S4 substrate in which the inhibitory domain was deleted (see Table 2). As expected, both βCTF and S4 are processed (FIG. 8B) and the S4 substrate did not display inhibitory activity. Since P3 peptides (Aβ17-40 and Aβ17-42) also contain the same inhibitory domain, this raises the question of whether this inhibition comes from either αCTF or P3 peptides. In order to distinguish between these possibilities, γ-secretase activity was assayed using the βCTF or βCTFΔ substrate in the presence of up to 30 nM P3-42 peptide (the highest concentration was chosen based on FIG. 3B showing the product concentration is less than 30 nM in the assay system) (FIG. 8C). P3-42 (Aβ17-42) at 1, 3, 10 and 30 nM did not inhibit γ-secretase activity for Aβ40 production in either substrate (FIG. 8C). This eliminated the possibility that the blockage of γ-secretase in this assay system is due to product feedback inhibition.

Taken together, these cellular and biochemical studies support the hypothesis that αCTF functions as an endogenous γ-secretase inhibitor for Aβ production, and therefore α-secretase plays an important role in regulating γ-secretase activity in addition to competing for substrates with β-secretase.

7.8 Example 7

The Flemish APP FAD Mutation Mitigates the Inhibitory Role of the Aβ17-21 Domain in the Regulation of γ-Secretase Activity and Increases Production of Aβ

There are five APP mutations within the Aβ region that cause early onset of AD or related disorders (Selkoe, 2001, *Physiol. Rev.* 81:741-766). These include Flemish (A617G in APP695 or A21G in Aβ), Arctic (E22G), Dutch (E22Q), Italian (E22K) and Iowa (D23N) (FIG. 9A). Since the Flemish mutation is located within the LVFF<u>A</u> core region and the other four are proximal to it, residing on one of the next two amino acids (LVFFA<u>ED</u>), it was determined how these mutations affect the function of the negative regulatory domain.

In order to directly compare their effect, five heptapeptides spanning the Aβ17-23 region that contain individual mutations were synthesized and their inhibitory potency toward γ-secretase was determined. Although each mutation led to an increase in IC50 (decreased inhibitory potency versus the WT sequence), only the heptapeptide containing the Flemish mutation showed a statistically significant decrease in inhibitory potency relative to that of the WT peptide (p value<0.01; FIG. 9B). This finding further suggests that the LVFFA sequence is the primary region responsible for the inhibitory effect and the C-terminal ED sequence has little contribution. Reduction of the inhibitory potency of this domain should lead to increased Aβ production. Indeed, previous studies have found that Flemish mutation considerably increased Aβ production, whereas other mutations have little effect on Aβ production (De Jonghe et al., 1998, *Neurobiol. Dis.* 5:281-286; Haass et al., 1994, 269:17741-17748; Nilsberth et al., 2001, *Nat. Neurosci.*, 4:887-893). These findings are consistent with the peptide inhibition studies disclosed herein. However, previous studies suggested that the Flemish mutation increased Aβ production by affecting α-secretase and β-secretase cleavage (Haass et al., 1994, *J. Biol. Chem.*, 269: 17741-17748).

Therefore, the effect of the Flemish mutation on APP processing was analyzed. The APP695 WT and APP Flemish were transfected into HEK293 cells and secreted APP species were examined. First, the Flemish mutation was confirmed to result in a 4.2-fold (p value<0.01) increase in production of secreted Aβ40 relative to WT (FIG. 9C) when equal amounts of APP protein were expressed in these cells (FIG. 9D upper panel). Second, the Flemish mutation was shown to have little effect on secreted sAPPα detected by 6E10 and W0-2 antibodies and sAPPβ measured with the anti-sAPPβ antibody (FIG. 9D lower three panels), suggesting that this mutation does not modify α-secretase and β-secretase activities. Clearly, the increased Aβ production in the Flemish-expressing cells results from either increased γ-secretase cleavage or decreased degradation.

To determine the effect of APP FAD mutations shown in FIG. 9A on γ-secretase activity, we overproduced recombinant βCTFs (β-secretase cleaved APP C-terminal fragments) and utilized them as substrates to detect γ-secretase activity in in vitro assays. The reaction rate of γ-secretase against these substrates was determined (FIG. 9E). We found that cleavage of the Flemish mutation substrate was 3-fold faster than WT, whereas the other mutations only slightly increased the γ-secretase reaction rate (from 1.2- to 1.4-fold). These studies indicate that the Flemish mutation provides a less inhibited substrate for γ-secretase and suggest that the elevated secretion of Aβ in Flemish FAD cells is mainly attributed to increased γ-secretase cleavage.

In order to consider the possibility that a specific region within APP, containing the Flemish mutation, may negatively regulate γ-secretase activity by binding to an allosteric site, we synthesized a series of peptides based on portions of βCTF that are upstream of the γ-secretase cleavage site and determined their inhibitory activity against γ-secretase. We found that Aβ17-20 (LVFF; SEQ ID NO:20), Aβ17-21 (LVFFA; SEQ ID NO:19) and Aβ17-23 (LVFFAED; SEQ ID NO:18) were capable of inhibiting γ-secretase activity with IC50 values of 0.94, 0.28 and 1.50 μM, respectively, whereas Aβ1-7, Aβ1-12, and Aβ1-16 fragments exerted no inhibition on γ-secretase activity.

Taken together, these studies show that a mutation within the core region of the inhibitory domain manifests significant effects on its interaction with γ-secretase. In other words, the disease state associated with the Flemish mutation is associated with the decreased potency of the internal inhibitory domain of the substrate.

7.9 Example 8
Evaluation of Novel γ-Secretase Substrate Using Electrochemi-luminescence Detection Previously published γ-secretase assays have used a truncated APP protein, C100Flag, which requires biotinylated 4G8 antibody directed to the substrate, in addition to G2-10 antibody that binds cleaved substrate, but does not bind to uncleaved substrate (Li Y M, Lai M T, Xu M, et al. Presenilin 1 is linked with gamma-secretase activity in the detergent solubilized state. Proc Natl Acad Sci USA. May 23, 2000; 97(11):6138-6143; Ida N, Hartmann T, Pantel J, et al. Analysis of heterogeneous A4 peptides in human cerebrospinal fluid and blood by a newly developed sensitive Western blot assay. J Biol. Chem. Sep. 13 1996; 271(37):22908-22914). G2-10 specifically recognizes the Aβ40 processed site of the cleaved substrate (Ida et al., 1996).

In order to eliminate the need for a biotinylated antibody for detection of γ-secretase activity, an AviTag (GLN-DIFEAQKIEWHE, amino acids 1-15 of SEQ ID NO:11) label was incorporated directly into the substrate. AviTag, a conserved peptide sequence, is recognized by biotin ligase that specifically catalyzes an attachment of biotin to a lysine residue within the peptide during target protein expression in *E. coli* (Schatz P J. Use of peptide libraries to map the substrate specificity of a peptide-modifying enzyme: a 13 residue consensus peptide specifies biotinylation in *Escherichia coli. Biotechnology* (NY). Oct. 1993;11(10):1138-1143). We constructed a double-tagged (AviTag and maltose binding protein, (MBP; GenBank Acc. No. AAC83813)) recombinant protein that facilitated protein purification and cleaved product detection. This chimeric protein also contains a thrombin cleavage site (Leu-Val-Pro-Arg- -Gly-Ser) between MBP and AviTag (see the schematic diagram in FIG. 14a). A DNA fragment encoding amino acid residues 620-695 of the APP695 substrate, which includes the γ-secretase cleavage sites, was prepared. A maltose-binding protein tag sequence at the N-terminus was cloned into the prokaryotic expression vector pIAD16-Avi vector. The recombinant protein, Sb4 (SEQ ID NO:27), was overproduced in *E. coli* (strain BL21 (DE3)) co-infected with the pACYC184 plasmid containing an IPTG inducible *BirA* gene to express biotin ligase. Expression of Sb4 protein, as well as biotin ligase, was induced using 0.1 mM IPTG for 5 hrs at 20° C. in the presence of 50 μM biotin (Fisher Scientific, BP232-1) to allow biotinylation of Sb4. *E. coli* cells were pelleted at 8,000g for 30 min., mechanically homogenized by French Press (Spectronic Instruments), and supernatants collected following a 30 min. spin at 17,000g. Sb4 was subsequently affinity purified by applying the supernatant to an amylose resin using Amersham Biosciences AKTAprime chromatographic system. Fractions containing the product were collected and thrombin-cleaved to remove the MBP-tag and provide the desired Sb4, biotinylated AviTag-APP695(620-695). The identity and biotinylation of Sb4 has been confirmed by LC-MS analysis and we determined that approximately 90% of Sb4protein is biotinylated (data shown in FIG. 14b). Substrate Sb4 or C100Flag (SEQ ID NO:28) at 1 μM were incubated with γ-secretase in the absence or presence of 1 μM of the potent γ-secretase inhibitor Compound E (Seiffert D, Bradley JD, Rominger CM, et al. Presenilin-1 and -2 are molecular targets for gamma-secretase inhibitors. *J Biol Chem*. Nov. 3 2000;275(44):34086-34091; Beher D, Wrigley JD, Nadin A, et al. Pharmacological knock-down of the presenilin 1 heterodimer by a novel gamma-secretase inhibitor: implications for presenilin biology. *J Biol Chem*. Nov. 30 2001;276(48):45394-45402) (see FIG. 1a). The γ-secretase cleaved Aβ product derived from C100Flag substrate was detected by a pair of antibodies (biotinylated 4G8 and ruthenylated G2-10*) while Sb4 cleaved product was detected by ruthenylated G2-10* alone (FIG. 10a) and quantified using electrochemiluminescence (ECL) technology. The ratio of signal to background for Sb4 and C100Flag were 93 and 7 to 1, respectively (FIG. 10a). Clearly, this newly engineered substrate exhibits significantly increased assay sensitivity for measuring in vitro γ-secretase activity while making use of only one antibody for product detection. However, the ECL γ-secretase assay is heterogeneous in nature and is not amenable to further miniaturization, therefore, it is not suitable for screening large libraries. In order to apply the γ-secretase assay in multi-well plate formats, we incorporated an HTRF detection method.

7.10 Example 9

Development of an HTRF Based Assay for γ-Secretase Activity in 384-Well Format

We set out to transfer the assay conditions obtained with the ECL method to an HTRF detection based format (FIG. 10b). The HTRF detection mixture consisted of mouse G2-10 antibody for recognition of the C-terminal epitope of the cleaved product, a Europium-labeled anti-mouse antibody (commonly, an antibody is conjugated with a cryptate ligand that forms a three dimensional coordination cage structure surrounding a lanthanide such as $Eu^{3+}$), along with Streptavidin conjugated to a trimeric form of the fluorescent protein allophycocyanin referred to as XL665. Cleavage of Sb4 substrate allows G2-10 mouse antibody to bind to the Aβ40-processed site on the cleaved substrate. The Steptavidin-XL665 conjugate binds directly with the biotin moiety on the N-terminal end of the Sb4 derived product. The anti-mouse Europium antibody targets to the G2-10 antibody, bringing all of these entities into close proximity. The Europium and XL665 reagents are a compatible pair of donor-acceptor fluorophores, and excitation of Europium at 337 nm results in fluorescence energy resonance transfer (FRET) to XL665 which fluoresces at 665 nm (FIG. 10b).

Human γ-secretase was prepared from HeLa cell membranes as described previously (Li et al., 2000). Briefly, HeLa cell pellet was resuspended in 1×MES buffer (50 mM MES, pH 6.0, 150 mM KCl, 5 mM CaCl2, 5 mM MgCl2) and treated with 'complete' protease inhibitor (Boehringer Mannheim). The resuspended pellet was mechanically homogenized by passing the cells through the French Press (Spectronic Instruments), and subsequently spun down at 800 g to remove cell debris and nuclei. Next, the supernatants were spun at 100,000 g in order to pellet the membranes. The pelleted membranes were resuspended in 1×MES buffer to approximately 12 mg/ml. This entire procedure was performed at 4° C. HeLa membranes were solubilized using 1% CHAPSO detergent in 1×MES buffer with protease inhibitors. After incubating for 1 hr at 4° C., the membrane was spun down at 100,000 g and the supernatants were collected and stored at −70° C. The collected fraction is defined as solubilized γ-secretase.

HTRF conditions were initially optimized in a 384-well format using a final volume of 20 µl. The high control for this assay was defined as the observed γ-secretase activity in the presence of 1% DMSO (v/v) and the low control as the activity observed when including 100 nM final concentration of Compound E (v/v). First, we determined a tolerable DMSO concentration that would not interfere with γ-secretase activity. Even with 3% DMSO (v/v) present in the assay mixture, there was virtually no effect on the γ-secretase activity (FIG. 11a), which was critical as delivery of library screening compounds required a final concentration of 2% DMSO (v/v) in the γ-secretase reaction. Next, we titrated the HTRF mixture components in an effort to minimize reagent costs for use in high throughput screening. A high signal was witnessed at 1 nM G2-10, however, we chose a final concentration of 0.3 nM that exhibited the desired 4:1 signal to noise ratio (FIG. 11b). Additionally, we varied Europium conjugated anti-mouse antibody and determined that 1 nM of this reagent in the HTRF mixture was sufficient for our assay conditions even though the signal continued to increase with higher concentrations of the anti-mouse antibody (FIG. 11c). Finally, using this optimized assay (2% DMSO (v/v), 0.3 nM G2-10 and 1 nM Europium-conjugated anti-mouse antibody), we examined the IC50 values of the two GSIs (γ-secretase inhibitors) L-685,458 and Compound E and determined that they were 1.4 and 1.1 nM, respectively in our HTRF assay, which is consistent with data using the ECL assay (FIG. 11d).

7.11 Example 10

γ-Secretase Assay Miniaturization to a 1536-Well Format and Pilot Screening

We have further miniaturized the HTRF assay from the established 384-well format to a 1536-well platform enabling more efficient screening of large chemical libraries. We showed that miniaturization did not lead to any apparent discrepancies when comparing biochemical activity from the 384- and 1536-well formats (FIG. 11e), since both formats exhibit similar signal to background ratios. Based on these optimization experiments, we set our final assay conditions at 0.3 nM G2-10, 1 nM anti-mouse antibody, 15 nM Streptavidin-XL665, and proceeded with the assay at 10 µl final volume (5 µl γ-secretase mix+5 µl HTRF mix) in the 1536-well format for screening.

7.12 Example 11

High Throughput Screening Assay for Modulators of γ-Secretase Activity

Following the optimization of assay conditions in a 1536-well format, we proceeded to validate this newly miniaturized γ-secretase assay in a pilot high throughput screen against a library of approximately 3,000 compounds. First, a control run consisting of two 1536-well plates was performed; one as a high control plate representing γ-secretase activity in 1% DMSO (v/v) and the other as a low control plate representing residual activity of fully inhibited γ-secretase using the γ-secretase inhibitor Compound E at 100 nM in 1% DMSO (v/v). FIGS. 12a and 12b depict the control run results and reveal excellent separation between high and low control wells using HTRF resulting in a Z' factor of 0.74 and a signal to noise ratio of 4 to 1. The calculated coefficient of variation (CV) values for the high and low controls were 4.96% and 6.78%, respectively (FIG. 12b). These data demonstrate that the multi-well plate high throughput assay is very stable even when fully automated, and that the assay possesses minimal well-to-well variability. Therefore a validation pilot screen of 3,000 library compounds was undertaken.

The pilot screen was carried out at a single dose of 10 µM for each library compound in 1% DMSO (v/v) using the comparable conditions that would be utilized for a full-scale high throughput screening campaign of uncharacterized candidate compounds (e.g. same robotic platform, readers, reagents, etc.). The pilot assay was performed in duplicate on two separate days to account for any day-to-day variability. This allowed us to obtain field data on assay performance, assay sensitivity for identifying inhibitors, an estimate of the initial hit rate, an overall assessment of compound interference, and most importantly, an evaluation of assay reproducibility by comparing the two individual data sets from each screening. The initial hit rate of the pilot screen was 1.1% and was consistent with previously screened in vitro assay targets at the Memorial Sloan-Kettering Cancer Center High Throughput Screening Core Facility. This similar hit rate was likely because these two validation libraries contain several pan-active compounds that have the potential to act as promiscuous active agents in the assay (Antczak C, Shum D, Escobar S, et al. High-throughput identification of inhibitors of human mitochondrial peptide deformylase. J Biomol Screen. June 2007; 12(4):521-535; Antczak C, Shum D, Radu C, Seshan V E, Djaballah H. Development and validation of a high-density fluorescence polarization-based assay for the *trypanosoma* RNA triphosphatase TbCet1. Comb Chem High Throughput Screen. March 2009; 12(3):258-268).

The chemical library used for the pilot screen combines approximately 3,000 chemicals obtained commercially from Prestwick Chemical (67400 Illkirch, France) and MicroSource Discovery Sytems, Inc. (Gaylordsville, Conn.). Biotin was included in both the Prestwick and MicroSource libraries. The MicroSource library contains 2,000 biologically active and structurally diverse compounds from known drugs, experimental bioactives, and pure natural products. The library includes a reference collection of 160 synthetic and natural toxic substances (inhibitors of DNA/RNA synthesis, protein synthesis, cellular respiration, and membrane integrity), a collection of 80 compounds representing classical and experimental, pesticides, herbicides, and endocrine disruptors, as well as a unique collection of 720 natural products and their derivatives. Additionally, the collection includes simple and complex oxygen-containing heterocycles, alkaloids, sequiterpenes, diterpenes, pentercyclic triterpenes, sterols, and many other diverse representatives. The Prestwick Chemical library is a unique collection of 880 high purity chemical compounds (all off-patent) and carefully selected for: structural diversity, and a broad spectrum covering several therapeutic areas (from neuropsychiatry to cardiology, immunology, anti-inflammatory, analgesia and more), known safety, and bioavailability in humans. Over 85% of its compounds are marketed drugs.

The Z' factor was used to assess assay performance. The Z' factor constitutes a dimensionless parameter that ranges from 1 (infinite separation) to <0. It is defined as: $1-Z'=(3\sigma_{c+}+3\sigma_{c-})/|\mu_{c+}-\mu_{c-}|$ where $\sigma_{c+}$, $\sigma_{c-}$, $\mu_{c+}$ and $\mu_{c-}$ are the standard deviations ($\sigma$) and averages ($\mu$) of the high (c+) and low (c−) controls (Zhang J H, Chung T D, Oldenburg K R. A Simple Statistical Parameter for Use in Evaluation and Validation of High Throughput Screening Assays. J Biomol Screen. 1999; 4(2):67-73). The Z' values per plate were consistent with those obtained during the original control run with Z' values of 0.75 or 0.76 from the four 1536-well duplicate assay plates. The scatter plot of the screen performed on two subsequent days demonstrates excellent reproducibility between the two days (FIG. 12*c*, Quadrants I and III) with the majority of inactive compounds centered on the zero axis and an estimated assay noise of 25%.

FIG. 13 summarizes a few of the active compounds obtained from this pilot screen. Among them, biotin was twice identified as an active hit in the pilot screen because it was present in both the Prestwick chemicals and MicroSource libraries (FIG. 13). The substrate used in our assay is biotinylated and the detection step employs Streptavidin-conjugated fluorophore, therefore, excess biotin disrupts the Streptavidin-XL665 interaction with substrate (FIG. 10*b*). Cisplatin, a platinum-based chemotherapeutic drug used to treat various cancers, results in DNA crosslinking and leads to induction of cell death through apoptosis. It was identified as an active compound in the pilot screen likely due to its ability to quench the Europium fluorescence signal, and is an example of a promiscuous active agent in this γ-secretase assay (FIG. 13). Pepstatin A, a biologically relevant and well-characterized inhibitor of aspartic acid proteases (Li Y M, Lai M T, Xu M, et al. Presenilin 1 is linked with gamma-secretase activity in the detergent solubilized state. Proc Natl Acad Sci USA. May 23, 2000; 97(11):6138-6143; Marciniszyn J, Jr., Hartsuck J A, Tang J. Mode of inhibition of acid proteases by pepstatin. J Biol. Chem. Nov. 25 1976; 251(22):7088-7094), was identified as an active compound by this high throughput assay during the pilot screen (FIG. 13). We subjected pepstatin A to a dose response study in order to establish its potency against γ-secretase in our assay and determined that it inhibits the enzyme with a calculated IC50 of 6.43 μM (FIG. 12*d*).

7.13. Example 12

The Aβ42 HTRF Assay

The Aβ42 HTRF γ-secretase assay is a biochemical assay that provides a means of examining in vitro γ-secretase activity. γ-Secretase cleaves APP in two unique positions to create the β-amyloid species Aβ40 and Aβ42. These protein fragments constitute the characteristic β-amyloid plaques witnessed in Alzheimer's disease and have been implicated in the pathogenesis of this neurodegenerative disease. Furthermore, the Aβ42 species is more hydrophobic and putatively more toxic: Aβ42, being more hydrophobic, more readily forms β-amyloid plaques that are characteristic in the pathogenesis of Alzheimer's disease. Therefore, development of γ-secretase inhibitors that specifically target inhibition of Aβ42 over Aβ40, or other γ-secretase substrates is an attractive therapeutic approach. These inhibitors have been shown to inhibit β-amyloid plaque formation in animal models, yet few developed inhibitors have the ability to specifically target Aβ42 inhibition.

Measuring production of Aβ42 provides a means of quantifying γ-secretase activity. This is a biochemical assay for γ-secretase activity that utilizes a biotinylated, recombinant protein fragment of APP and is suited for high throughput drug screening. The majority of previous γ-secretase biochemical assays are heterogeneous in nature, requiring manual separation of components. This characteristic has prevented many previous assays from being transferred to a high throughput-screening format. Here, a homogeneous, HTRF biochemical assay is presented, which has successfully been moved and miniaturized to a 384-well high throughput platform. This Aβ42 assay can be separated into two portions: 1) γ-secretase activity step, and 2) an HTRF detection step.

Using the CT6-I45F γ-secretase substrate, a novel HTRF assay is presented, which is capable of 384-well screening with a final reaction volume of 20 μl. Solubilized γ-secretase is incubated with substrate and library compounds (10 μl volume) for 2.5 hours, followed by addition of an HTRF detection mixture (10 μl) that is then incubated with the γ-secretase solution for approximately 12 hrs at room temperature. This HTRF mixture included G2-11 antibody that recognizes only γ-secretase-cleaved product (at the Aβ42 cleavage site) and not substrate, in addition to the Europium-labeled anti-mouse antibody and Steptavidin-XL665 fluorophores. Prior to addition of the HTRF mixture, G2-11 antibody is pre-incubated with the Europium-labeled anti-mouse antibody to allow binding of the two entities. CT-6 cleavage by γ-secretase allows G2-11 binding to the product and the Europium-labeled antibody interacts directly with G2-11. The joining of Steptavidin-XL665 to the biotinylated substrate brings the XL-665 and Europium fluorophores into close proximity and FRET takes place upon excitation at 337 nm.

This assay may be advantageously used for screening large libraries of chemical compounds for their potential to inhibit γ-secretase. More specifically, when chemical libraries are screened with both Aβ40 and Aβ42 HTRF assays, it provides a novel means of screening for γ-secretase inhibitors that preferentially inhibit Aβ42 formation. This approach may lead to the discovery and development of novel classes of inhibitors that possess great therapeutic value in Alzheimer's disease.

Among the advantages of this Aβ42 HTRF γ-secretase assay is the construction of the biotinylated, recombinant CT6-I45F substrate, which has provided a highly active substrate allowing for increased sensitivity and detection of γ-secretase activity. This recombinant protein is based on the sequence of APP, but has a truncation that removes an auto-inhibitory domain. This provides markedly increased activity. Furthermore, an AviTag site has been cloned into the vector encoding this substrate. Consequently, overproduction of the CT6-I45F substrate in the presence of biotin ligase and biotin results in direct biotinylation of our substrate. This novel approach further increases the sensitivity of the assay. Other attempts at development of a high throughput γ-secretase assay that screens for Aβ42 have been unsuccessful. This is the first successful development of a biochemical assay that screens for γ-secretase cleavage at the Aβ42-site and is suited for high throughput screening. Other assays have utilized biotinylated antibodies detecting portions of APP and this has prevented the necessary adaptation of assays to a homogeneous platform. As such, another advantage of this assay is the screening capability at 384-format. This assay allows for extremely efficient and cost-effective screening of large libraries of chemical compounds. Another advantage of this assay is related to the other Aβ40 HTRF high throughput assay described supra. When both assays are used to screen chemical libraries, the between the recorded "hits" can be compared, enabling the determination of which compounds inhibit Aβ42 cleavage but do not affect Aβ40 cleavage. An Aβ42-specific γ-secretase inhibitor is a highly sought-after entity in Alzheimer's disease research.

Moreover, the design of the CT6-I45F substrate is novel. An auto-inhibitory domain that was previously unknown has been removed from APP, and the substrate is biotinylated during production. Additionally, a mutation has been engineered into the recombinant substrate that increases γ-secretase preference for cleavage at the Aβ42 site. This provides for a marked increase in Aβ42-site cleaved substrate and results in a concomitant increase in assay signal. These design features have allowed for the creation of a sensitive HTRF γ-secretase assay capable of miniaturization to 384-well format and cost-effective screening. Additionally, this approach has provided a novel miniaturization of a biochemical Aβ42-specific γ-secretase assay to the 384-well platform.

7.14. Example 13
Development of an Exo-Cell γ-Secretase Assay Using a Biotinylated Recombinant APP Substrate We recently demonstrated that it is possible to directly biotinylate a γ-secretase peptide substrate to be utilized in an in vitro assay (Yin Y I, Bassit B, Zhu L, Yang X, Wang C, Li Y M: {gamma}-Secretase Substrate Concentration Modulates the Abeta42/Abeta40 Ratio: IMPLICATIONS FOR ALZHEIMER DISEASE. *J Biol Chem* 2007, 282(32): 23639-23644). Here, we have designed a truncated, recombinant APP protein that is directly biotinylated during overproduction in *E. coli*. This substrate is highly active and offers an advantage to develop an easy and sensitive γ-secretase assay, since it eliminates the need for an exogenous biotinylated binding agent such as a biotinylated antibody. This allows for the elimination of stable transfection of γ-secretase substrate into the cell line of interest or isolation of membrane from large numbers of cells that can then be examined using an in vitro γ-secretase assay.

Preparation of biotinylated γ-secretase substrate Sb4. A DNA fragment encompassing the 76 amino acid residues at positions 620-695 of the 695-aa isoform of APP as well as a maltose binding protein tag was cloned into the pIAD16 prokaryotic vector (McCafferty D G, Lessard I A, Walsh C T: Mutational analysis of potential zinc-binding residues in the active site of the enterococcal D-Ala-D-Ala dipeptidase VanX. Biochemistry 1997, 36(34):10498-10505). Additionally, there was an AviTag also incorporated into this vector. AviTag, a specific 15-residue peptide, is recognized by biotin ligase that specifically catalyzes an attachment of biotin to the lysine residue within the AviTag (See FIG. 14a). The chimeric protein was then co-expressed in *Eschericia coli* with the pACYC184 biotin ligase plasmid. IPTG at 0.1 mM was used to induce expression of biotinylated recombinant substrate Sb4 as well as biotin ligase at 20° C. for 5 hrs in the presence of 50 μM biotin. Biotin ligase directly biotinylates the Avitag during protein expression. Sb4 was ultimately affinity purified using an amylose resin column, eluted with excess maltose and thrombin-cleaved to remove maltose-binding protein from the purified substrate. After the recombinant protein was isolated, the sample was analyzed by LC-MS (FIG. 14b). The analysis showed that there were two species with molecular masses of 12,053 and 12,279, which correlated to nonbiotinylated and biotinylated forms of substrate (calculated molecular masses were 12,050 and 12,276, respectively). LC-MS also shows that approximately 90% of purified Sb4 was biotinylated.

Exo-cell assay for γ-secretase using Sb4. The Sb4 substrate, toward which γ-secretase is highly active was applied to develop an assay capable of quantifying γ-secretase activity directly in cultured cells that eliminates the need for stable transfection of substrate into cells or the isolation of γ-secretase—bearing membranes from the cell line of interest. An exo-cell assay was designed that would allow for the evaluation of γ-secretase in real-time under diverse treatment conditions.

Previously, Li et al. (2000) had determined that in an in vitro γ-secretase assay, CHAPSO was superior to other detergents for promoting activity. Therefore, HeLa cells were first incubated with Sb4 substrate, as well as CHAPSO detergent as depicted in FIG. 14c. Cells were seeded at their indicated concentration in 96-well plates and allowed to attach overnight. The next day, media was removed and cells were washed once with PBS. Fresh media was then added containing 0.25% CHAPSO detergent, Sb4 substrate to a final concentration of 1 μM, and 1% DMSO or γ-secretase inhibitor. This was incubated for 2.5 hours at 37° C. Media was removed and cell debris was pelleted from this media for 5 min. at 3,500 rpm. Supernatant was then added to ruthenylated G2-10* antibody that recognizes cleaved product, but not uncleaved substrate. This was incubated for an additional 2 hours at room temperature. Finally, magnetic streptavidin beads were added to a final concentration of 80 μg/ml and incubated for 30 min. at room temperature. Assay buffer was added to the samples and γ-secretase-mediated cleavage of substrate was monitored using electrochemiluminescence (ECL) (Li et al., 2000). (FIG. 14c).

The concentration of CHAPSO required for assaying activity in cells was first optimized. It was determined that reproducible γ-secretase activity was detected within a range from 0.15% CHAPSO to an upper limit as high as 0.3% detergent. However, the greatest amount of activity was detected by using 0.25% CHAPSO (FIG. 15a), which is consistent with findings in a previously reported in vitro assay (Li et al., 2000). The activity at each of these concentrations could be attributed to γ-secretase in the HeLa cells as treatment with GSI abrogated cleavage of Sb4 (data only shown for 0.25% CHAPSO, FIG. 15a). Next, the sensitivity of the assay was evaluated by determining the lower limit of HeLa cell numbers needed to detect γ-secretase activity. Reproducible protease activity was found from as few as 2,500 HeLa adenocarcinoma cells with a signal to noise ratio greater than 5:1 (FIG. 15b). Activity was cell-number dependent, increasing from 1000 HeLa cells to 10,000 cells with the greatest activity found using 10,000 HeLa cells, which produced a signal to noise ratio of approximately 125:1. The signal reaches its maximal amount at 10,000 HeLa cells and levels off at 20,000 HeLa cells, probably due under the present conditions to the limiting substrate concentration in the assay.

7.15. Example 14

Evaluation of γ-Secretase Inhibitors in the Exo-Cell Assay

Inhibition by various γ-secretase inhibitors was evaluated in the exo-cell assay and the $IC_{50}$ values compared to those from comparable in vitro and whole cell-based assays (Table 3).

is biotinylated additional 6E10 biotinylated antibody used in earlier assays is not required. In the cell-based assay, N2A mouse neuroblastoma cells that stably overexpress amyloid precursor protein were incubated with γ-secretase inhibitors in a final concentration of 1% DMSO for 24 hrs. Following incubation, the supernatant was removed from the cells and assayed for Aβ40, the cleaved APP product, using ruthenylated G2-10* antibody as well as biotinylated 4G8 antibody.

A variety of inhibitors was assayed, including the benzodiazepine Compound E and a sulfonamide-based inhibitor referred to as GSI-34 (see structures in Table 3). It was found that these compounds inhibit γ-secretase in the nanomolar range in our in vitro assay, and that their $IC_{50}$ values are slightly elevated in the exo-cell assay (Table 3). In a comple-

TABLE 3

Potency of γ-Secretase Inhibitors in Various Activity Assays.

| γ-Secretase Inhibitor | Structure | In Vitro (nM) | Cell-based (nM) | Exo-Cell (nM) | Extended Exo-Cell (nM) |
|---|---|---|---|---|---|
| Compound E | [structure] | 1.2 | 4.6 | 3.8 | 2.8 |
| GSI-34 | [structure] | 1.0 | 32.4 | 5.9 | 39.0 |

The potency of two structurally different GSIs was assayed in four unique γ-secretase activity assays. $IC_{50}$ values were determined from the dose response curves using a non-linear regression analysis in the Prism software. An in vitro assay was based on the one previously reported by Li et al. (2000), except we utilized Sb4 substrate that eliminated the need for biotinylated antibody. The cell-based activity assay used N2A mouse neuroblastoma cells stably over-expressing APP and a biotinylated 4G8 antibody that binds the C-terminus of the amyloid beta peptide. The exo-cell assay incubated HeLa cells simultaneously with GSI, Sb4 substrate as well as 0.25% CHAPSO detergent prior to detecting substrate cleavage. Finally, the extended exo-cell assay first incubated HeLa cells with GSI for 24 hrs. Subsequently, the cells were washed 1× in PBS and then incubated with Sb4 substrate and CHAPSO detergent. The assay was then carried out exactly as described for the original exo-cell method. All assays incorporate ruthenylated G2-10* antibody to detect 40-site cleavage of APP or recombinant Sb4 substrate and quantitated activity by measuring ECL. The latter assays were performed as previously described (Li et al., 2000). In the in vitro assay, recombinant Sb4 substrate was incubated for 2.5 hours at 37° C. in pH 7.0 PIPES buffer in the presence of 0.25% CHAPSO detergent and solubilized γ-secretase at a final concentration of 40 ng/ul. The detection of cleaved substrate was determined using ruthenylated G2-10* antibody. Since the Sb4 substrate mentary assay, homogeneous time-resolved fluorescence (HTRF) technology detected cleaved substrate in the exo-cell assay. The calculated $IC_{50}$ values for Compound E and GSI-34 were 3.8 nM and 5.9 nM, respectively, using ECL, whereas they were 5.4 nM and 5.4 nM, respectively, using HTRF.

7.16. Example 15

Detection of Real-Time γ-Secretase Inhibition Using an Extended Exo-Cell Assay

The exo-cell assay was adapted to monitor real-time γ-secretase activity and inhibition over extended times of pretreatment regimens. After HeLa cells were incubated with varying concentrations of GSI-34 or Compound E for 24 hrs, media was removed and the cells were washed to remove excess unbound inhibitor. Fresh media containing only CHAPSO detergent and Sb4 substrate were placed back onto the cells and the exo-cell assay was then conducted as previously described. HeLa cells that were treated in this manner with GSI-34 show a dose-dependent inhibition of γ-secretase activity (FIG. 15c). This modified, extended treatment exo-cell assay is capable of quantifying remaining γ-secretase activity following drug treatment on virtually any cell type. The $IC_{50}$ values for Compound E and GSI-34 were calculated using the extended exo-cell assay (Table 3 and FIG. 15d). Comparing the potency of these unique GSIs in currently established in vitro and cell-based assays reveals that the extended exo-cell assay more closely mimics that witnessed in a cell-based γ-secretase assay that uses N2A mouse neuroblastoma cells stably expressing the APP substrate (Table 3 and FIG. 15d). The $IC_{50}$ values for Compound E and GSI-34 in the extended exo-cell assay were 2.83 nM and 38.7 nM respectively (FIG. 15d) as compared to 4.6 nM and 32.4 nM, respectively, in the cell-based assay (Table 3)—both GSIs exhibited decreased potency in the cell-based and extended exo-cell assays as compared to their respective in vitro values. Regardless, the trend of decreasing potencies of GSIs in the extended exo-cell assay is similar to that witnessed in the stable N2A-APP cell-based system and this is likely due to the GSIs being incubated for 24 hours in the presence of a cellular environment that can affect compound half-life amongst other factors. These data show that our exo-cell assay can be used to evaluate the real-time status of γ-secretase activity in cell lines in a simple and sensitive manner. This validation of a real-time exo-cell screening assay for identifying γ-secretase inhibitors means that the present screen may be applied to identify potential therapeutics for use in treating Alzheimer's disease as well as various neoplasms like T-cell acute lymphoblastic leukemia where γ-secretase-mediated Notch signaling is tumorigenic.

7.17. Example 16

Correlation of Exo-Cell γ-Secretase Activity Assay with Cell Growth

Clearly, the extended exo-cell assay can be applied to quickly and efficiently quantitate the γ-secretase activity from any cultured cells in real-time. As such, we set out to utilize this novel assay to ascertain whether there exists a correlation between inhibition of γ-secretase and inhibition of cellular proliferation in a γ-secretase-dependent lymphoma line. Notch receptors require γ-secretase processing to release an intracellular fragment that translocates into the nucleus to transmit its signal. Multiple lymphoma lines have been shown to be dependent upon γ-secretase activity (Kogoshi H, Sato T, Koyama T, Nara N, Tohda S: Gamma-secretase inhibitors suppress the growth of leukemia and lymphoma cells. Oncol Rep 2007, 18(1):77-80; He F, Wang L, Hu X B, Yin D D, Zhang P, Li G H, Wang Y C, Huang S Y, Liang Y M, Han H: Notch and BCR signaling synergistically promote the proliferation of Raji B lymphoma cells. Leuk Res 2008).

For a lymphoma cell proliferation assay, A20 mouse lymphoma cells were seeded in a 96-well plate at a concentration of $5 \times 10_5$ cells/ml in 100 μl RPMI media containing 2% fetal bovine serum. An additional 100 μl of media containing DMSO or γ-secretase inhibitor was added and incubated for 48 hours at 37° C. After this incubation, the cells were incubated for 5 hours with 2 μCi/ml [$^3$H]thymidine at 37° C. Proliferative response was then evaluated by harvesting the tritiated DNA from cells using a Skatron cell harvester and proliferation assessed as a function of [$^3$H]thymidine incorporation measured on a β-counter.

We found that the A20 mouse lymphoma line is sensitive to γ-secretase inhibition by GSI compounds (FIG. 16a) following 48 hours of pretreatment. Furthermore, we established that there is a detectable correlation between this inhibition of cellular proliferation in A20 cells and inhibition of γ-secretase. Treatment of the A20 cell line with the three structurally unique, small molecule GSIs L-685,458, Compound E, and GSI-34 were all able to inhibit cellular proliferation (FIG. 16a for GSI-34; L-685,458 and Compound E data not shown) likely eliminating the possibility of an off-target, non-γ-secretase related effect. Interestingly, the data in FIG. 16a suggests that a small amount of remaining γ-secretase activity is sufficient to maintain cellular proliferation in this particular model system. For instance, 300 nM GSI-34 is able to inhibit approximately 80% of γ-secretase activity, yet this concentration only reduces cellular proliferation by 30% in the A20 mouse lymphoma model system. This data may help to explain the common finding that therapeutic levels of GSIs required to inhibit proliferation of Notch-dependent neoplastic cell lines are often far greater than in vitro IC50 values. The results in this Example show that extended exo-cell screening assays to identify inhibitors of γ-secretase may provide potential therapeutic agents of use in treating γ-secretase-dependent tumors.

7.18. Example 17

Quantification of Real-Time γ-Secretase Activity in Primary Tumor Samples

It was not known whether this exo-cell method could be used to measure activity in primary samples from patients. Peripheral primary B-cell chronic lymphocytic leukemia cells (B-CLL) are arrested in the G0 phase of the cell cycle (Reed J C: Molecular biology of chronic lymphocytic leukemia. Semin Oncol 1998, 25(1):11-18). This condition makes it very difficult to assay γ-secretase activity in these primary cell samples. Additionally, it has been shown that Notch2 plays a role in the overexpression of CD23 in B-CLL and this may be related to the development of this neoplasm (Hubmann R, Schwarzmeier J D, Shehata M, Hilgarth M, Duechler M, Dettke M, Berger R: Notch2 is involved in the overexpression of CD23 in B-cell chronic lymphocytic leukemia. Blood 2002, 99(10):3742-3747). Therefore, the study of γ-secretase and Notch with regard to B-CLL biology has recently become an urgent issue.

Stable transfection of substrate into a non-proliferating cell line is not a practical option and isolating enough B-CLL cells from a patient to prepare membrane fractions for use in in vitro assays is not feasible. However, the exo-cell assay now allows for the determination of protease activity quite easily. Primary B-CLL patient samples were obtained from patients diagnosed with B-cell chronic lymphocytic leukemia who were untreated. Written informed consent was obtained from each patient in accordance with the guidelines of the Institutional Review Board of Memorial Sloan Kettering Cancer Center and the Declaration of Helsinki Peripheral blood mononuclear cells (PBMCs) were isolated using standard Ficoll-Hypaque density gradient and subsequently stored in liquid nitrogen. Prior to use in assay, samples were thawed and resuspended in RPMI media and allowed to attach overnight at 37° C. The extended exo-cell assay was then performed as described above.

We quantitated activity from three separate B-CLL patient samples and defined background activity for the assay in the presence of 1 μM Compound E (FIG. 16b) from 50,000 total B-CLL cells. Using the exo-cell assay we have been able to characterize γ-secretase activity in B-CLL patient samples for the first time. This previously would have been nearly impossible, but this assay makes it simple to detect protease activity in troublesome B-CLL patient samples in a few hours. The present results, taken together with those presented in the immediately preceding Examples, clearly demonstrate that the detection of real-time activity is a significant development due to the central role of γ-secretase in numerous biological signaling pathways as well as in various disease states. In addition, these results clearly demonstrate that extended exo-cell screening assays permit the discovery of inhibitors of γ-secretase, which in turn may provide potential therapeutic agents of use in treating γ-secretase-dependent tumors. Furthermore the results in these Examples indicate that real-time γ-secretase assays can be readily carried across a wide range of cell lines and tissues, including tissue samples obtained from patients suffering from a variety of cancers.

We claim:

1. A method of screening for an inhibitor of γ-secretase activity comprising the steps of:
   a) providing a container comprising a composition comprising γ-secretase activity;
   b) contacting the composition with a mixture comprising a candidate compound and a polypeptide substrate for γ-secretase, wherein the polypeptide substrate comprises modified APP polypeptide, wherein the modified APP polypeptide comprises at least one amino acid substitution, deletion, or insertion, in the γ-secretase inhibitory domain Leu-Val-Phe-Phe-Ala (SEQ ID NO:19) and a detectable label bound thereto, wherein the detectable label is a chimeric peptide sequence attached to the amino terminus of the modified APP, wherein cleavage of the modified APP polypeptide by γ-secretase provides a labeled product that is detectable;
   c) incubating the candidate compound, the polypeptide substrate, and the γ-secretase; and
   d) determining whether the candidate compound inhibits formation of the labeled product.

2. The method described in claim 1 wherein the chimeric peptide sequence comprises an avidin, a maltose binding protein, a FLAG epitope, a glutathione dehydrogenase, or a horse radish peroxidase.

3. The method described in claim 1 wherein the determining comprises assaying for the labeled product, wherein assaying for the labeled product comprises assaying for a detectable complex comprising the labeled product and at least one detectable probe.

4. The method described in claim 3 wherein the detectable complex comprises a specific binding member that comprises the detectable probe, wherein the specific binding member specifically binds the labeled product to form a binary complex.

5. The method described in claim 4 wherein the detectable probe comprises ruthenium.

6. The method described in claim 1 wherein the determining further comprises
   d) contacting the labeled product with
      1) a first ligand bearing a first tag wherein the first ligand specifically binds the detectable label, and
      2) a second ligand bearing a second tag wherein the second ligand specifically binds the labeled product;
      3) a third ligand bearing a third tag wherein the third ligand specifically binds the second ligand; and
   e) determining the presence or the amount of the labeled product bound to the first ligand, the second ligand, and the third ligand.

7. The method described in claim 6 wherein the first ligand comprises a biotin and the first tag comprises a detectable fluorescence acceptor.

8. The method described in claim 7 wherein the second ligand comprises a first antibody that specifically binds a C-terminus of the labeled product, the first antibody being bound to a second antibody bearing a fluorescence donor that excites the fluorescence acceptor tag bound to the first ligand.

9. The method described in claim 1 wherein the container is a well in a multi-well assay plate, thereby providing a high throughput method of screening.

10. The method described in claim 9 wherein the plate contains at least 96 wells, or at least 384 wells, or at least 1536 wells.

11. The method described in claim 1 wherein the modified APP polypeptide comprises a deletion of the γ-secretase inhibitory domain.

12. The method described in claim 1 wherein the modified APP polypeptide comprises an amino acid sequence chosen from SEQ ID NO:9, 10, 13, 14, 25, or 6.

13. The method described in claim 1 wherein the γ-secretase inhibitory domain comprises an amino acid residue that is not phenylalanine at position 3 of SEQ ID NO:4, position 4 of SEQ ID NO:4, or both position 3 and position 4 of SEQ ID NO:4.

14. The method described in claim 1 wherein each residue of the γ-secretase inhibitory domain comprises a substitution.

15. The method described in claim 1 wherein the modified APP polypeptide comprises amino acid residues 620-695 of APP695 (SEQ ID NO:1).

16. The method described in claim 4 wherein the specific binding member comprises an anti-Aβ antibody.

17. The method described in claim 16 wherein the anti-Aβ antibody binds the C-terminus of the modified APP that is exposed after (i) γ-secretase mediated cleavage at the Aβ38 γ-secretase cleavage and does not bind an uncleaved modified APP, (ii) γ-secretase mediated cleavage at the Aβ40 γ-secretase cleavage and does not bind an uncleaved modified APP, or (iii) γ-secretase mediated cleavage at the Aβ42 γ-secretase cleavage and does not bind an uncleaved modified APP.

18. The method described in claim 6 wherein the second ligand comprises an anti-Aβ antibody, wherein the anti-Aβ antibody binds the C-terminus of the modified APP that is exposed after (i) gamma-secretase mediated cleavage at the Aβ38 gamma-secretase cleavage and does not bind an uncleaved modified APP, (ii) gamma-secretase mediated cleavage at the Aβ40 gamma-secretase cleavage and does not bind an uncleaved modified APP, or (iii) gamma-secretase mediated cleavage at the Aβ42 gamma-secretase cleavage and does not bind an uncleaved modified APP.

19. The method described in claim 6 wherein the third ligand comprises a rare earth metal ion.

\* \* \* \* \*

UNITED STATES PATENT AND TRADEMARK OFFICE
CERTIFICATE OF CORRECTION

| | | Page 1 of 1 |
|---|---|---|
| PATENT NO. | : 9,023,767 B2 | |
| APPLICATION NO. | : 12/776141 | |
| DATED | : May 5, 2015 | |
| INVENTOR(S) | : Christopher Chad Shelton, Yuan Tian and Yueming Li | |

It is certified that error appears in the above-identified patent and that said Letters Patent is hereby corrected as shown below:

In the Specification

At Column 1, line 7, delete

"The disclosures of the present application were developed with support from the U.S. Government (NIH grant AG026660), and the Government has certain rights in any patents granted on such disclosures."

and replace with

--This invention was made with government support under AG026660 awarded by the National Institutes of Health. The government has certain rights in the invention.--

Signed and Sealed this
Twenty-fifth Day of August, 2015

Michelle K. Lee
*Director of the United States Patent and Trademark Office*

SEQUENCE LISTING

<160> NUMBER OF SEQ ID NOS: 28

<210> SEQ ID NO 1
<211> LENGTH: 695
<212> TYPE: PRT
<213> ORGANISM: Homo sapiens

<400> SEQUENCE: 1

Met Leu Pro Gly Leu Ala Leu Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Val Ala Glu Val Glu Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Glu Ser Val Glu Glu Val Val Arg
        275                 280                 285

Val Pro Thr Thr Ala Ala Ser Thr Pro Asp Ala Val Asp Lys Tyr Leu
    290                 295                 300

Glu Thr Pro Gly Asp Glu Asn Glu His Ala His Phe Gln Lys Ala Lys
305                 310                 315                 320

Glu Arg Leu Glu Ala Lys His Arg Glu Arg Met Ser Gln Val Met Arg
                325                 330                 335

Glu Trp Glu Glu Ala Glu Arg Gln Ala Lys Asn Leu Pro Lys Ala Asp
            340                 345                 350

Lys Lys Ala Val Ile Gln His Phe Gln Glu Lys Val Glu Ser Leu Glu
        355                 360                 365

```
Gln Glu Ala Ala Asn Glu Arg Gln Gln Leu Val Glu Thr His Met Ala
370                 375                 380

Arg Val Glu Ala Met Leu Asn Asp Arg Arg Leu Ala Leu Glu Asn
385                 390                 395                 400

Tyr Ile Thr Ala Leu Gln Ala Val Pro Pro Arg Pro Arg His Val Phe
                405                 410                 415

Asn Met Leu Lys Lys Tyr Val Arg Ala Glu Gln Lys Asp Arg Gln His
                420                 425                 430

Thr Leu Lys His Phe Glu His Val Arg Met Val Asp Pro Lys Lys Ala
                435                 440                 445

Ala Gln Ile Arg Ser Gln Val Met Thr His Leu Arg Val Ile Tyr Glu
450                 455                 460

Arg Met Asn Gln Ser Leu Ser Leu Leu Tyr Asn Val Pro Ala Val Ala
465                 470                 475                 480

Glu Glu Ile Gln Asp Glu Val Asp Glu Leu Leu Gln Lys Glu Gln Asn
                485                 490                 495

Tyr Ser Asp Asp Val Leu Ala Asn Met Ile Ser Glu Pro Arg Ile Ser
                500                 505                 510

Tyr Gly Asn Asp Ala Leu Met Pro Ser Leu Thr Glu Thr Lys Thr Thr
                515                 520                 525

Val Glu Leu Leu Pro Val Asn Gly Glu Phe Ser Leu Asp Asp Leu Gln
530                 535                 540

Pro Trp His Ser Phe Gly Ala Asp Ser Val Pro Ala Asn Thr Glu Asn
545                 550                 555                 560

Glu Val Glu Pro Val Asp Ala Arg Pro Ala Ala Asp Arg Gly Leu Thr
                565                 570                 575

Thr Arg Pro Gly Ser Gly Leu Thr Asn Ile Lys Thr Glu Glu Ile Ser
                580                 585                 590

Glu Val Lys Met Asp Ala Glu Phe Arg His Asp Ser Gly Tyr Glu Val
                595                 600                 605

His His Gln Lys Leu Val Phe Phe Ala Glu Asp Val Gly Ser Asn Lys
610                 615                 620

Gly Ala Ile Ile Gly Leu Met Val Gly Gly Val Val Ile Ala Thr Val
625                 630                 635                 640

Ile Val Ile Thr Leu Val Met Leu Lys Lys Lys Gln Tyr Thr Ser Ile
                645                 650                 655

His His Gly Val Val Glu Val Asp Ala Ala Val Thr Pro Glu Glu Arg
                660                 665                 670

His Leu Ser Lys Met Gln Gln Asn Gly Tyr Glu Asn Pro Thr Tyr Lys
                675                 680                 685

Phe Phe Glu Gln Met Gln Asn
690                 695

<210> SEQ ID NO 2
<211> LENGTH: 751
<212> TYPE: PRT
<213> ORGANISM: Homo sapiens

<400> SEQUENCE: 2

Met Leu Pro Gly Leu Ala Leu Leu Leu Leu Ala Ala Trp Thr Ala Arg
1               5                   10                  15

Ala Leu Glu Val Pro Thr Asp Gly Asn Ala Gly Leu Leu Ala Glu Pro
                20                  25                  30

Gln Ile Ala Met Phe Cys Gly Arg Leu Asn Met His Met Asn Val Gln
                35                  40                  45
```

```
Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Glu Ser Val Glu Glu Val Val Arg
        275                 280                 285

Glu Val Cys Ser Glu Gln Ala Glu Thr Gly Pro Cys Arg Ala Met Ile
    290                 295                 300

Ser Arg Trp Tyr Phe Asp Val Thr Glu Gly Lys Cys Ala Pro Phe Phe
305                 310                 315                 320

Tyr Gly Gly Cys Gly Gly Asn Arg Asn Asn Phe Asp Thr Glu Glu Tyr
                325                 330                 335

Cys Met Ala Val Cys Gly Ser Ala Ile Pro Thr Thr Ala Ala Ser Thr
            340                 345                 350

Pro Asp Ala Val Asp Lys Tyr Leu Glu Thr Pro Gly Asp Glu Asn Glu
        355                 360                 365

His Ala His Phe Gln Lys Ala Lys Glu Arg Leu Glu Ala Lys His Arg
    370                 375                 380

Glu Arg Met Ser Gln Val Met Arg Glu Trp Glu Glu Ala Glu Arg Gln
385                 390                 395                 400

Ala Lys Asn Leu Pro Lys Ala Asp Lys Lys Ala Val Ile Gln His Phe
                405                 410                 415

Gln Glu Lys Val Glu Ser Leu Glu Gln Glu Ala Ala Asn Glu Arg Gln
            420                 425                 430

Gln Leu Val Glu Thr His Met Ala Arg Val Glu Ala Met Leu Asn Asp
        435                 440                 445

Arg Arg Arg Leu Ala Leu Glu Asn Tyr Ile Thr Ala Leu Gln Ala Val
    450                 455                 460
```

```
Pro Pro Arg Pro Arg His Val Phe Asn Met Leu Lys Lys Tyr Val Arg
465                 470                 475                 480

Ala Glu Gln Lys Asp Arg Gln His Thr Leu Lys His Phe Glu His Val
            485                 490                 495

Arg Met Val Asp Pro Lys Lys Ala Ala Gln Ile Arg Ser Gln Val Met
        500                 505                 510

Thr His Leu Arg Val Ile Tyr Glu Arg Met Asn Gln Ser Leu Ser Leu
    515                 520                 525

Leu Tyr Asn Val Pro Ala Val Ala Glu Glu Ile Gln Asp Glu Val Asp
530                 535                 540

Glu Leu Gln Lys Glu Gln Asn Tyr Ser Asp Asp Val Leu Ala Asn
545                 550                 555                 560

Met Ile Ser Glu Pro Arg Ile Ser Tyr Gly Asn Asp Ala Leu Met Pro
                565                 570                 575

Ser Leu Thr Glu Thr Lys Thr Thr Val Glu Leu Leu Pro Val Asn Gly
            580                 585                 590

Glu Phe Ser Leu Asp Asp Leu Gln Pro Trp His Ser Phe Gly Ala Asp
        595                 600                 605

Ser Val Pro Ala Asn Thr Glu Asn Glu Val Glu Pro Val Asp Ala Arg
    610                 615                 620

Pro Ala Ala Asp Arg Gly Leu Thr Thr Arg Pro Gly Ser Gly Leu Thr
625                 630                 635                 640

Asn Ile Lys Thr Glu Glu Ile Ser Glu Val Lys Met Asp Ala Glu Phe
                645                 650                 655

Arg His Asp Ser Gly Tyr Glu Val His His Gln Lys Leu Val Phe Phe
            660                 665                 670

Ala Glu Asp Val Gly Ser Asn Lys Gly Ala Ile Ile Gly Leu Met Val
        675                 680                 685

Gly Gly Val Val Ile Ala Thr Val Ile Val Ile Thr Leu Val Met Leu
    690                 695                 700

Lys Lys Lys Gln Tyr Thr Ser Ile His His Gly Val Val Glu Val Asp
705                 710                 715                 720

Ala Ala Val Thr Pro Glu Glu Arg His Leu Ser Lys Met Gln Gln Asn
                725                 730                 735

Gly Tyr Glu Asn Pro Thr Tyr Lys Phe Phe Glu Gln Met Gln Asn
            740                 745                 750

<210> SEQ ID NO 3
<211> LENGTH: 770
<212> TYPE: PRT
<213> ORGANISM: Homo sapiens

<400> SEQUENCE: 3

Met Leu Pro Gly Leu Ala Leu Leu Leu Leu Ala Ala Trp Thr Ala Arg
 1               5                  10                  15

Ala Leu Glu Val Pro Thr Asp Gly Asn Ala Gly Leu Leu Ala Glu Pro
             20                  25                  30

Gln Ile Ala Met Phe Cys Gly Arg Leu Asn Met His Met Asn Val Gln
         35                  40                  45

Asn Gly Lys Trp Asp Ser Asp Pro Ser Gly Thr Lys Thr Cys Ile Asp
     50                  55                  60

Thr Lys Glu Gly Ile Leu Gln Tyr Cys Gln Glu Val Tyr Pro Glu Leu
 65                  70                  75                  80

Gln Ile Thr Asn Val Val Glu Ala Asn Gln Pro Val Thr Ile Gln Asn
                 85                  90                  95
```

```
Trp Cys Lys Arg Gly Arg Lys Gln Cys Lys Thr His Pro His Phe Val
            100                 105                 110
Ile Pro Tyr Arg Cys Leu Val Gly Glu Phe Val Ser Asp Ala Leu Leu
            115                 120                 125
Val Pro Asp Lys Cys Lys Phe Leu His Gln Glu Arg Met Asp Val Cys
130                 135                 140
Glu Thr His Leu His Trp His Thr Val Ala Lys Glu Thr Cys Ser Glu
145                 150                 155                 160
Lys Ser Thr Asn Leu His Asp Tyr Gly Met Leu Leu Pro Cys Gly Ile
                165                 170                 175
Asp Lys Phe Arg Gly Val Glu Phe Val Cys Cys Pro Leu Ala Glu Glu
            180                 185                 190
Ser Asp Asn Val Asp Ser Ala Asp Ala Glu Glu Asp Asp Ser Asp Val
            195                 200                 205
Trp Trp Gly Gly Ala Asp Thr Asp Tyr Ala Asp Gly Ser Glu Asp Lys
210                 215                 220
Val Val Glu Val Ala Glu Glu Glu Val Ala Glu Val Glu Glu Glu Glu
225                 230                 235                 240
Glu Ala Asp Asp Asp Glu Asp Asp Glu Asp Gly Asp Glu Val Glu Glu
                245                 250                 255
Glu Ala Glu Glu Pro Tyr Glu Glu Ala Thr Glu Arg Thr Thr Ser Ile
            260                 265                 270
Ala Thr Thr Thr Thr Thr Thr Thr Glu Ser Val Glu Glu Val Val Arg
            275                 280                 285
Glu Val Cys Ser Glu Gln Ala Glu Thr Gly Pro Cys Arg Ala Met Ile
            290                 295                 300
Ser Arg Trp Tyr Phe Asp Val Thr Glu Gly Lys Cys Ala Pro Phe Phe
305                 310                 315                 320
Tyr Gly Gly Cys Gly Gly Asn Arg Asn Asn Phe Asp Thr Glu Glu Tyr
                325                 330                 335
Cys Met Ala Val Cys Gly Ser Ala Met Ser Gln Ser Leu Leu Lys Thr
                340                 345                 350
Thr Gln Glu Pro Leu Ala Arg Asp Pro Val Lys Leu Pro Thr Thr Ala
            355                 360                 365
Ala Ser Thr Pro Asp Ala Val Asp Lys Tyr Leu Glu Thr Pro Gly Asp
370                 375                 380
Glu Asn Glu His Ala His Phe Gln Lys Ala Lys Glu Arg Leu Glu Ala
385                 390                 395                 400
Lys His Arg Glu Arg Met Ser Gln Val Met Arg Glu Trp Glu Glu Ala
                405                 410                 415
Glu Arg Gln Ala Lys Asn Leu Pro Lys Ala Asp Lys Lys Ala Val Ile
            420                 425                 430
Gln His Phe Gln Glu Lys Val Glu Ser Leu Glu Gln Glu Ala Ala Asn
            435                 440                 445
Glu Arg Gln Gln Leu Val Glu Thr His Met Ala Arg Val Glu Ala Met
            450                 455                 460
Leu Asn Asp Arg Arg Arg Leu Ala Leu Glu Asn Tyr Ile Thr Ala Leu
465                 470                 475                 480
Gln Ala Val Pro Pro Arg Pro Arg His Val Phe Asn Met Leu Lys Lys
            485                 490                 495
Tyr Val Arg Ala Glu Gln Lys Asp Arg Gln His Thr Leu Lys His Phe
            500                 505                 510
```

-continued

```
Glu His Val Arg Met Val Asp Pro Lys Lys Ala Ala Gln Ile Arg Ser
            515                 520                 525

Gln Val Met Thr His Leu Arg Val Ile Tyr Glu Arg Met Asn Gln Ser
    530                 535                 540

Leu Ser Leu Leu Tyr Asn Val Pro Ala Val Ala Glu Glu Ile Gln Asp
545                 550                 555                 560

Glu Val Asp Glu Leu Leu Gln Lys Glu Gln Asn Tyr Ser Asp Asp Val
                565                 570                 575

Leu Ala Asn Met Ile Ser Glu Pro Arg Ile Ser Tyr Gly Asn Asp Ala
                580                 585                 590

Leu Met Pro Ser Leu Thr Glu Thr Lys Thr Thr Val Glu Leu Leu Pro
            595                 600                 605

Val Asn Gly Glu Phe Ser Leu Asp Asp Leu Gln Pro Trp His Ser Phe
        610                 615                 620

Gly Ala Asp Ser Val Pro Ala Asn Thr Glu Asn Glu Val Glu Pro Val
625                 630                 635                 640

Asp Ala Arg Pro Ala Ala Asp Arg Gly Leu Thr Thr Arg Pro Gly Ser
                645                 650                 655

Gly Leu Thr Asn Ile Lys Thr Glu Glu Ile Ser Glu Val Lys Met Asp
            660                 665                 670

Ala Glu Phe Arg His Asp Ser Gly Tyr Glu Val His His Gln Lys Leu
        675                 680                 685

Val Phe Phe Ala Glu Asp Val Gly Ser Asn Lys Gly Ala Ile Ile Gly
690                 695                 700

Leu Met Val Gly Gly Val Val Ile Ala Thr Val Ile Val Ile Thr Leu
705                 710                 715                 720

Val Met Leu Lys Lys Lys Gln Tyr Thr Ser Ile His His Gly Val Val
                725                 730                 735

Glu Val Asp Ala Ala Val Thr Pro Glu Glu Arg His Leu Ser Lys Met
            740                 745                 750

Gln Gln Asn Gly Tyr Glu Asn Pro Thr Tyr Lys Phe Phe Glu Gln Met
        755                 760                 765

Gln Asn
    770

<210> SEQ ID NO 4
<211> LENGTH: 612
<212> TYPE: PRT
<213> ORGANISM: Homo sapiens

<400> SEQUENCE: 4

Met Leu Pro Gly Leu Ala Leu Leu Leu Ala Ala Trp Thr Ala Arg
  1               5                  10                  15

Ala Leu Glu Val Pro Thr Asp Gly Asn Ala Gly Leu Leu Ala Glu Pro
                20                  25                  30

Gln Ile Ala Met Phe Cys Gly Arg Leu Asn Met His Met Asn Val Gln
            35                  40                  45

Asn Gly Lys Trp Asp Ser Asp Pro Ser Gly Thr Lys Thr Cys Ile Asp
        50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
                100                 105                 110
```

```
Ile Pro Tyr Arg Cys Leu Val Gly Glu Phe Val Ser Asp Ala Leu Leu
        115                 120                 125
Val Pro Asp Lys Cys Lys Phe Leu His Gln Glu Arg Met Asp Val Cys
130                 135                 140
Glu Thr His Leu His Trp His Thr Val Ala Lys Glu Thr Cys Ser Glu
145                 150                 155                 160
Lys Ser Thr Asn Leu His Asp Tyr Gly Met Leu Leu Pro Cys Gly Ile
                165                 170                 175
Asp Lys Phe Arg Gly Val Glu Phe Val Cys Cys Pro Leu Ala Glu Glu
                180                 185                 190
Ser Asp Asn Val Asp Ser Ala Asp Ala Glu Glu Asp Asp Ser Asp Val
                195                 200                 205
Trp Trp Gly Gly Ala Asp Thr Asp Tyr Ala Asp Gly Ser Glu Asp Lys
210                 215                 220
Val Val Glu Val Ala Glu Glu Glu Val Ala Glu Val Glu Glu Glu
225                 230                 235                 240
Glu Ala Asp Asp Asp Glu Asp Asp Glu Asp Gly Asp Glu Val Glu Glu
                245                 250                 255
Glu Ala Glu Glu Pro Tyr Glu Glu Ala Thr Glu Arg Thr Thr Ser Ile
                260                 265                 270
Ala Thr Thr Thr Thr Thr Thr Thr Glu Ser Val Glu Glu Val Val Arg
        275                 280                 285
Val Pro Thr Thr Ala Ala Ser Thr Pro Asp Ala Val Asp Lys Tyr Leu
        290                 295                 300
Glu Thr Pro Gly Asp Glu Asn Glu His Ala His Phe Gln Lys Ala Lys
305                 310                 315                 320
Glu Arg Leu Glu Ala Lys His Arg Glu Arg Met Ser Gln Val Met Arg
                325                 330                 335
Glu Trp Glu Glu Ala Glu Arg Gln Ala Lys Asn Leu Pro Lys Ala Asp
                340                 345                 350
Lys Lys Ala Val Ile Gln His Phe Gln Glu Lys Val Glu Ser Leu Glu
                355                 360                 365
Gln Glu Ala Ala Asn Glu Arg Gln Gln Leu Val Glu Thr His Met Ala
                370                 375                 380
Arg Val Glu Ala Met Leu Asn Asp Arg Arg Arg Leu Ala Leu Glu Asn
385                 390                 395                 400
Tyr Ile Thr Ala Leu Gln Ala Val Pro Pro Arg Pro Arg His Val Phe
                405                 410                 415
Asn Met Leu Lys Lys Tyr Val Arg Ala Glu Gln Lys Asp Arg Gln His
                420                 425                 430
Thr Leu Lys His Phe Glu His Val Arg Met Val Asp Pro Lys Lys Ala
                435                 440                 445
Ala Gln Ile Arg Ser Gln Val Met Thr His Leu Arg Val Ile Tyr Glu
                450                 455                 460
Arg Met Asn Gln Ser Leu Ser Leu Leu Tyr Asn Val Pro Ala Val Ala
465                 470                 475                 480
Glu Glu Ile Gln Asp Glu Val Asp Glu Leu Leu Gln Lys Glu Gln Asn
                485                 490                 495
Tyr Ser Asp Asp Val Leu Ala Asn Met Ile Ser Glu Pro Arg Ile Ser
                500                 505                 510
Tyr Gly Asn Asp Ala Leu Met Pro Ser Leu Thr Glu Thr Lys Thr Thr
                515                 520                 525
```

```
Val Glu Leu Leu Pro Val Asn Gly Glu Phe Ser Leu Asp Asp Leu Gln
            530                 535                 540

Pro Trp His Ser Phe Gly Ala Asp Ser Val Pro Ala Asn Thr Glu Asn
545                 550                 555                 560

Glu Val Glu Pro Val Asp Ala Arg Pro Ala Asp Arg Gly Leu Thr
            565                 570                 575

Thr Arg Pro Gly Ser Gly Leu Thr Asn Ile Lys Thr Glu Glu Ile Ser
            580                 585                 590

Glu Val Lys Met Asp Ala Glu Phe Arg His Asp Ser Gly Tyr Glu Val
            595                 600                 605

His His Gln Lys
        610

<210> SEQ ID NO 5
<211> LENGTH: 596
<212> TYPE: PRT
<213> ORGANISM: Homo sapiens

<400> SEQUENCE: 5

Met Leu Pro Gly Leu Ala Leu Leu Leu Ala Ala Trp Thr Ala Arg
  1               5                  10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
 50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
            85                  90                  95

Trp Cys Lys Arg Gly Arg Lys Gln Cys Lys Thr His Pro His Phe Val
        100                 105                 110

Ile Pro Tyr Arg Cys Leu Val Gly Glu Phe Val Ser Asp Ala Leu Leu
    115                 120                 125

Val Pro Asp Lys Cys Lys Phe Leu His Gln Glu Arg Met Asp Val Cys
130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
            165                 170                 175

Asp Lys Phe Arg Gly Val Glu Phe Val Cys Cys Pro Leu Ala Glu Glu
        180                 185                 190

Ser Asp Asn Val Asp Ser Ala Asp Ala Glu Glu Asp Asp Ser Asp Val
    195                 200                 205

Trp Trp Gly Gly Ala Asp Thr Asp Tyr Ala Asp Gly Ser Glu Asp Lys
210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
            245                 250                 255

Glu Ala Glu Glu Pro Tyr Glu Glu Ala Thr Glu Arg Thr Thr Ser Ile
        260                 265                 270

Ala Thr Thr Thr Thr Thr Thr Thr Glu Ser Val Glu Glu Val Val Arg
    275                 280                 285
```

Val Pro Thr Thr Ala Ala Ser Thr Pro Asp Ala Val Asp Lys Tyr Leu
            290                 295                 300

Glu Thr Pro Gly Asp Glu Asn Glu His Ala His Phe Gln Lys Ala Lys
305                 310                 315                 320

Glu Arg Leu Glu Ala Lys His Arg Glu Arg Met Ser Gln Val Met Arg
                325                 330                 335

Glu Trp Glu Glu Ala Glu Arg Gln Ala Lys Asn Leu Pro Lys Ala Asp
            340                 345                 350

Lys Lys Ala Val Ile Gln His Phe Gln Glu Lys Val Glu Ser Leu Glu
        355                 360                 365

Gln Glu Ala Ala Asn Glu Arg Gln Gln Leu Val Glu Thr His Met Ala
    370                 375                 380

Arg Val Glu Ala Met Leu Asn Asp Arg Arg Arg Leu Ala Leu Glu Asn
385                 390                 395                 400

Tyr Ile Thr Ala Leu Gln Ala Val Pro Pro Arg Pro Arg His Val Phe
                405                 410                 415

Asn Met Leu Lys Lys Tyr Val Arg Ala Glu Gln Lys Asp Arg Gln His
            420                 425                 430

Thr Leu Lys His Phe Glu His Val Arg Met Val Asp Pro Lys Lys Ala
        435                 440                 445

Ala Gln Ile Arg Ser Gln Val Met Thr His Leu Arg Val Ile Tyr Glu
    450                 455                 460

Arg Met Asn Gln Ser Leu Ser Leu Leu Tyr Asn Val Pro Ala Val Ala
465                 470                 475                 480

Glu Glu Ile Gln Asp Glu Val Asp Glu Leu Leu Gln Lys Glu Gln Asn
                485                 490                 495

Tyr Ser Asp Asp Val Leu Ala Asn Met Ile Ser Glu Pro Arg Ile Ser
            500                 505                 510

Tyr Gly Asn Asp Ala Leu Met Pro Ser Leu Thr Glu Thr Lys Thr Thr
        515                 520                 525

Val Glu Leu Leu Pro Val Asn Gly Glu Phe Ser Leu Asp Asp Leu Gln
    530                 535                 540

Pro Trp His Ser Phe Gly Ala Asp Ser Val Pro Ala Asn Thr Glu Asn
545                 550                 555                 560

Glu Val Glu Pro Val Asp Ala Arg Pro Ala Ala Asp Arg Gly Leu Thr
                565                 570                 575

Thr Arg Pro Gly Ser Gly Leu Thr Asn Ile Lys Thr Glu Glu Ile Ser
            580                 585                 590

Glu Val Lys Met
        595

<210> SEQ ID NO 6
<211> LENGTH: 690
<212> TYPE: PRT
<213> ORGANISM: Homo sapiens

<400> SEQUENCE: 6

Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
                20                  25                  30

Gln Ile Ala Met Phe Cys Gly Arg Leu Asn Met His Met Asn Val Gln
            35                  40                  45

Asn Gly Lys Trp Asp Ser Asp Pro Ser Gly Thr Lys Thr Cys Ile Asp

-continued

```
            50                  55                  60
Thr Lys Glu Gly Ile Leu Gln Tyr Cys Gln Glu Val Tyr Pro Glu Leu
 65                  70                  75                  80

Gln Ile Thr Asn Val Val Glu Ala Asn Gln Pro Val Thr Ile Gln Asn
                 85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
            115                 120                 125

Val Pro Asp Lys Cys Lys Phe Leu His Gln Glu Arg Met Asp Val Cys
130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
            195                 200                 205

Trp Trp Gly Gly Ala Asp Thr Asp Tyr Ala Asp Gly Ser Glu Asp Lys
210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Glu Ser Val Glu Glu Val Val Arg
            275                 280                 285

Val Pro Thr Thr Ala Ala Ser Thr Pro Asp Ala Val Asp Lys Tyr Leu
            290                 295                 300

Glu Thr Pro Gly Asp Glu Asn Glu His Ala His Phe Gln Lys Ala Lys
305                 310                 315                 320

Glu Arg Leu Glu Ala Lys His Arg Glu Arg Met Ser Gln Val Met Arg
                325                 330                 335

Glu Trp Glu Glu Ala Glu Arg Gln Ala Lys Asn Leu Pro Lys Ala Asp
            340                 345                 350

Lys Lys Ala Val Ile Gln His Phe Gln Glu Lys Val Glu Ser Leu Glu
            355                 360                 365

Gln Glu Ala Ala Asn Glu Arg Gln Gln Leu Val Glu Thr His Met Ala
370                 375                 380

Arg Val Glu Ala Met Leu Asn Asp Arg Arg Arg Leu Ala Leu Glu Asn
385                 390                 395                 400

Tyr Ile Thr Ala Leu Gln Ala Val Pro Pro Arg Pro Arg His Val Phe
                405                 410                 415

Asn Met Leu Lys Lys Tyr Val Arg Ala Glu Gln Lys Asp Arg Gln His
            420                 425                 430

Thr Leu Lys His Phe Glu His Val Arg Met Val Asp Pro Lys Lys Ala
            435                 440                 445

Ala Gln Ile Arg Ser Gln Val Met Thr His Leu Arg Val Ile Tyr Glu
450                 455                 460

Arg Met Asn Gln Ser Leu Ser Leu Leu Tyr Asn Val Pro Ala Val Ala
465                 470                 475                 480
```

```
Glu Glu Ile Gln Asp Glu Val Asp Leu Leu Gln Lys Glu Gln Asn
            485                 490                 495

Tyr Ser Asp Asp Val Leu Ala Asn Met Ile Ser Glu Pro Arg Ile Ser
        500                 505                 510

Tyr Gly Asn Asp Ala Leu Met Pro Ser Leu Thr Glu Thr Lys Thr Thr
        515                 520                 525

Val Glu Leu Leu Pro Val Asn Gly Glu Phe Ser Leu Asp Asp Leu Gln
    530                 535                 540

Pro Trp His Ser Phe Gly Ala Asp Ser Val Pro Ala Asn Thr Glu Asn
545                 550                 555                 560

Glu Val Glu Pro Val Asp Ala Arg Pro Ala Ala Asp Arg Gly Leu Thr
                565                 570                 575

Thr Arg Pro Gly Ser Gly Leu Thr Asn Ile Lys Thr Glu Glu Ile Ser
                580                 585                 590

Glu Val Lys Met Asp Ala Glu Phe Arg His Asp Ser Gly Tyr Glu Val
                595                 600                 605

His His Gln Lys Glu Asp Val Gly Ser Asn Lys Gly Ala Ile Ile Gly
            610                 615                 620

Leu Met Val Gly Gly Val Val Ile Ala Thr Val Ile Val Ile Thr Leu
625                 630                 635                 640

Val Met Leu Lys Lys Lys Gln Tyr Thr Ser Ile His His Gly Val Val
                645                 650                 655

Glu Val Asp Ala Ala Val Thr Pro Glu Glu Arg His Leu Ser Lys Met
                660                 665                 670

Gln Gln Asn Gly Tyr Glu Asn Pro Thr Tyr Lys Phe Phe Glu Gln Met
            675                 680                 685

Gln Asn
    690

<210> SEQ ID NO 7
<211> LENGTH: 83
<212> TYPE: PRT
<213> ORGANISM: Homo sapiens

<400> SEQUENCE: 7

Leu Val Phe Phe Ala Glu Asp Val Gly Ser Asn Lys Gly Ala Ile Ile
1               5                   10                  15

Gly Leu Met Val Gly Gly Val Val Ile Ala Thr Val Ile Val Ile Thr
                20                  25                  30

Leu Val Met Leu Lys Lys Lys Gln Tyr Thr Ser Ile His His Gly Val
            35                  40                  45

Val Glu Val Asp Ala Ala Val Thr Pro Glu Glu Arg His Leu Ser Lys
    50                  55                  60

Met Gln Gln Asn Gly Tyr Glu Asn Pro Thr Tyr Lys Phe Phe Glu Gln
65                  70                  75                  80

Met Gln Asn

<210> SEQ ID NO 8
<211> LENGTH: 99
<212> TYPE: PRT
<213> ORGANISM: Homo sapiens

<400> SEQUENCE: 8

Asp Ala Glu Phe Arg His Asp Ser Gly Tyr Glu Val His Gln Lys
1               5                   10                  15
```

```
Leu Val Phe Phe Ala Glu Asp Val Gly Ser Asn Lys Gly Ala Ile Ile
             20                  25                  30

Gly Leu Met Val Gly Gly Val Val Ile Ala Thr Val Ile Val Ile Thr
         35                  40                  45

Leu Val Met Leu Lys Lys Lys Gln Tyr Thr Ser Ile His His Gly Val
 50                  55                  60

Val Glu Val Asp Ala Ala Val Thr Pro Glu Glu Arg His Leu Ser Lys
 65                  70                  75                  80

Met Gln Gln Asn Gly Tyr Glu Asn Pro Thr Tyr Lys Phe Phe Glu Gln
                 85                  90                  95

Met Gln Asn

<210> SEQ ID NO 9
<211> LENGTH: 43
<212> TYPE: PRT
<213> ORGANISM: Homo sapiens

<400> SEQUENCE: 9

Gly Leu Asn Asp Ile Phe Glu Ala Gln Lys Ile Glu Trp His Glu Lys
 1               5                  10                  15

Gly Ala Ile Ile Gly Leu Met Val Gly Gly Val Val Ile Ala Thr Val
             20                  25                  30

Ile Val Ile Thr Leu Val Met Leu Lys Lys Lys
         35                  40

<210> SEQ ID NO 10
<211> LENGTH: 54
<212> TYPE: PRT
<213> ORGANISM: Homo sapiens

<400> SEQUENCE: 10

Gly Leu Asn Asp Ile Phe Glu Ala Gln Lys Ile Glu Trp His Glu Leu
 1               5                  10                  15

Val Phe Phe Ala Glu Asp Val Gly Ser Asn Lys Gly Ala Ile Ile Gly
             20                  25                  30

Leu Met Val Gly Gly Val Val Ile Ala Thr Val Ile Val Ile Thr Leu
         35                  40                  45

Val Met Leu Lys Lys Lys
 50

<210> SEQ ID NO 11
<211> LENGTH: 106
<212> TYPE: PRT
<213> ORGANISM: Homo sapiens

<400> SEQUENCE: 11

Gly Leu Asn Asp Ile Phe Glu Ala Gln Lys Ile Glu Trp His Glu Leu
 1               5                  10                  15

Val Phe Phe Ala Glu Asp Val Gly Ser Asn Lys Gly Ala Ile Ile Gly
             20                  25                  30

Leu Met Val Gly Gly Val Val Ile Ala Thr Val Ile Val Ile Thr Leu
         35                  40                  45

Val Met Leu Lys Lys Lys Gln Tyr Thr Ser Ile His His Gly Val Val
 50                  55                  60

Glu Val Asp Ala Ala Val Thr Pro Glu Glu Arg His Leu Ser Lys Met
 65                  70                  75                  80

Gln Gln Asn Gly Tyr Glu Asn Pro Thr Tyr Lys Phe Phe Glu Gln Met
                 85                  90                  95
```

Gln Asn Asp Tyr Lys Asp Asp Asp Lys
            100             105

<210> SEQ ID NO 12
<211> LENGTH: 99
<212> TYPE: PRT
<213> ORGANISM: Homo sapiens

<400> SEQUENCE: 12

Gly Leu Asn Asp Ile Phe Glu Ala Gln Lys Ile Glu Trp His Glu Val
1               5                   10                  15

Gly Ser Asn Lys Gly Ala Ile Ile Gly Leu Met Val Gly Gly Val Val
            20                  25                  30

Ile Ala Thr Val Ile Val Ile Thr Leu Val Met Leu Lys Lys Lys Gln
        35                  40                  45

Tyr Thr Ser Ile His His Gly Val Val Glu Val Asp Ala Ala Val Thr
    50                  55                  60

Pro Glu Glu Arg His Leu Ser Lys Met Gln Gln Asn Gly Tyr Glu Asn
65                  70                  75                  80

Pro Thr Tyr Lys Phe Phe Glu Gln Met Gln Asn Asp Tyr Lys Asp Asp
                85                  90                  95

Asp Asp Lys

<210> SEQ ID NO 13
<211> LENGTH: 106
<212> TYPE: PRT
<213> ORGANISM: Homo sapiens

<400> SEQUENCE: 13

Gly Leu Asn Asp Ile Phe Glu Ala Gln Lys Ile Glu Trp His Glu Tyr
1               5                   10                  15

Glu Val His His Gln Lys Val Gly Ser Asn Lys Gly Ala Ile Ile Gly
            20                  25                  30

Leu Met Val Gly Gly Val Val Ile Ala Thr Val Ile Val Ile Thr Leu
        35                  40                  45

Val Met Leu Lys Lys Lys Gln Tyr Thr Ser Ile His His Gly Val Val
    50                  55                  60

Glu Val Asp Ala Ala Val Thr Pro Glu Glu Arg His Leu Ser Lys Met
65                  70                  75                  80

Gln Gln Asn Gly Tyr Glu Asn Pro Thr Tyr Lys Phe Phe Glu Gln Met
                85                  90                  95

Gln Asn Asp Tyr Lys Asp Asp Asp Lys
            100             105

<210> SEQ ID NO 14
<211> LENGTH: 106
<212> TYPE: PRT
<213> ORGANISM: Homo sapiens

<400> SEQUENCE: 14

Gly Leu Asn Asp Ile Phe Glu Ala Gln Lys Ile Glu Trp His Glu Val
1               5                   10                  15

Ala Gly Ala Gly Gly Asn Val Gly Ser Asn Lys Gly Ala Ile Ile Gly
            20                  25                  30

Leu Met Val Gly Gly Val Val Ile Ala Thr Val Ile Val Ile Thr Leu
        35                  40                  45

Val Met Leu Lys Lys Lys Gln Tyr Thr Ser Ile His His Gly Val Val

```
                50             55               60
Glu Val Asp Ala Ala Val Thr Pro Glu Glu Arg His Leu Ser Lys Met
 65                  70                  75                  80

Gln Gln Asn Gly Tyr Glu Asn Pro Thr Tyr Lys Phe Phe Glu Gln Met
                 85                  90                  95

Gln Asn Asp Tyr Lys Asp Asp Asp Lys
                100             105
```

```
<210> SEQ ID NO 15
<211> LENGTH: 38
<212> TYPE: PRT
<213> ORGANISM: Homo sapiens

<400> SEQUENCE: 15

Asp Ala Glu Phe Arg His Asp Ser Gly Tyr Glu Val His His Gln Lys
 1               5                  10                  15

Leu Val Phe Phe Ala Glu Asp Val Gly Ser Asn Lys Gly Ala Ile Ile
            20                  25                  30

Gly Leu Met Val Gly Gly
            35
```

```
<210> SEQ ID NO 16
<211> LENGTH: 40
<212> TYPE: PRT
<213> ORGANISM: Homo sapiens

<400> SEQUENCE: 16

Asp Ala Glu Phe Arg His Asp Ser Gly Tyr Glu Val His His Gln Lys
 1               5                  10                  15

Leu Val Phe Phe Ala Glu Asp Val Gly Ser Asn Lys Gly Ala Ile Ile
            20                  25                  30

Gly Leu Met Val Gly Gly Val Val
            35                  40
```

```
<210> SEQ ID NO 17
<211> LENGTH: 42
<212> TYPE: PRT
<213> ORGANISM: Homo sapiens

<400> SEQUENCE: 17

Asp Ala Glu Phe Arg His Asp Ser Gly Tyr Glu Val His His Gln Lys
 1               5                  10                  15

Leu Val Phe Phe Ala Glu Asp Val Gly Ser Asn Lys Gly Ala Ile Ile
            20                  25                  30

Gly Leu Met Val Gly Gly Val Val Ile Ala
            35                  40
```

```
<210> SEQ ID NO 18
<211> LENGTH: 7
<212> TYPE: PRT
<213> ORGANISM: Homo sapiens

<400> SEQUENCE: 18

Leu Val Phe Phe Ala Glu Asp
 1               5
```

```
<210> SEQ ID NO 19
<211> LENGTH: 5
<212> TYPE: PRT
<213> ORGANISM: Homo sapiens
```

```
<400> SEQUENCE: 19

Leu Val Phe Phe Ala
1               5

<210> SEQ ID NO 20
<211> LENGTH: 4
<212> TYPE: PRT
<213> ORGANISM: Homo sapiens

<400> SEQUENCE: 20

Leu Val Phe Phe
1

<210> SEQ ID NO 21
<211> LENGTH: 8
<212> TYPE: PRT
<213> ORGANISM: Homo sapiens

<400> SEQUENCE: 21

Leu Val Phe Phe Ala Glu Asp Val
1               5

<210> SEQ ID NO 22
<211> LENGTH: 8
<212> TYPE: PRT
<213> ORGANISM: Homo sapiens

<400> SEQUENCE: 22

Lys Leu Val Phe Phe Ala Glu Asp
1               5

<210> SEQ ID NO 23
<211> LENGTH: 7
<212> TYPE: PRT
<213> ORGANISM: Homo sapiens
<220> FEATURE:
<223> OTHER INFORMATION: Glu(6)-methyl ester
<223> OTHER INFORMATION: Asp(7)-methyl ester
<223> OTHER INFORMATION: C-terminal amide

<400> SEQUENCE: 23

Leu Val Phe Phe Ala Glu Asp
1               5

<210> SEQ ID NO 24
<211> LENGTH: 7
<212> TYPE: PRT
<213> ORGANISM: Homo sapiens
<220> FEATURE:
<223> OTHER INFORMATION: All D- amino acids
<223> OTHER INFORMATION: N-terminal glycylurethane
<223> OTHER INFORMATION: Asp(1)-methyl ester
<223> OTHER INFORMATION: Glu(2)-methyl ester
<223> OTHER INFORMATION: C-terminal amide

<400> SEQUENCE: 24

Asp Glu Ala Phe Phe Val Leu
1               5

<210> SEQ ID NO 25
<211> LENGTH: 104
<212> TYPE: PRT
<213> ORGANISM: Homo sapiens

<400> SEQUENCE: 25

Gly Ser His Met Asp Ala Glu Phe Arg His Asp Ser Gly Tyr Glu Val
```

```
                1               5                  10                 15
            His His Gln Lys Val Gly Ser Asn Lys Gly Ala Ile Ile Gly Leu Met
                            20                  25                  30

Val Gly Gly Val Val Ile Ala Thr Val Ile Val Ile Thr Leu Val Met
                            35                  40                  45

Leu Lys Lys Lys Gln Tyr Thr Ser Ile His His Gly Val Val Glu Val
                        50                  55                  60

Asp Ala Ala Val Thr Pro Glu Glu Arg His Leu Ser Lys Met Gln Gln
             65                 70                  75                  80

Asn Gly Tyr Glu Asn Pro Thr Tyr Lys Phe Phe Glu Gln Met Gln Asn
                            85                  90                  95

Asp Tyr Lys Asp Asp Asp Asp Lys
                        100
```

<210> SEQ ID NO 26
<211> LENGTH: 99
<212> TYPE: PRT
<213> ORGANISM: Homo sapiens

<400> SEQUENCE: 26

```
            Asp Ala Glu Phe Arg His Asp Ser Gly Tyr Glu Val His Gln Lys
             1               5                  10                  15

Val Ala Gly Ala Gly Gly Asn Val Gly Ser Asn Lys Gly Ala Ile Ile
                            20                  25                  30

Gly Leu Met Val Gly Gly Val Val Ile Ala Thr Val Ile Val Ile Thr
                            35                  40                  45

Leu Val Met Leu Lys Lys Lys Gln Tyr Thr Ser Ile His His Gly Val
                        50                  55                  60

Val Glu Val Asp Ala Ala Val Thr Pro Glu Glu Arg His Leu Ser Lys
             65                 70                  75                  80

Met Gln Gln Asn Gly Tyr Glu Asn Pro Thr Tyr Lys Phe Phe Glu Gln
                            85                  90                  95

Met Gln Asn
```

<210> SEQ ID NO 27
<211> LENGTH: 91
<212> TYPE: PRT
<213> ORGANISM: Homo sapiens

<400> SEQUENCE: 27

```
            Gly Leu Asn Asp Ile Phe Glu Ala Gln Lys Ile Glu Trp His Glu Val
             1               5                  10                  15

Gly Ser Asn Lys Gly Ala Ile Ile Gly Leu Met Val Gly Gly Val Val
                            20                  25                  30

Ile Ala Thr Val Ile Val Ile Thr Leu Val Met Leu Lys Lys Lys Gln
                            35                  40                  45

Tyr Thr Ser Ile His His Gly Val Val Glu Val Asp Ala Ala Val Thr
                        50                  55                  60

Pro Glu Glu Arg His Leu Ser Lys Met Gln Gln Asn Gly Tyr Glu Asn
             65                 70                  75                  80

Pro Thr Tyr Lys Phe Phe Glu Gln Met Gln Asn
                            85                  90
```

<210> SEQ ID NO 28
<211> LENGTH: 108
<212> TYPE: PRT
<213> ORGANISM: Homo sapiens

```
<400> SEQUENCE: 28

Met Asp Ala Glu Phe Arg His Asp Ser Gly Tyr Glu Val His His Gln
1               5                   10                  15

Lys Leu Val Phe Phe Ala Glu Asp Val Gly Ser Asn Lys Gly Ala Ile
                20                  25                  30

Ile Gly Leu Met Val Gly Gly Val Val Ile Ala Thr Val Ile Val Ile
            35                  40                  45

Thr Leu Val Met Leu Lys Lys Lys Gln Tyr Thr Ser Ile His His Gly
    50                  55                  60

Val Val Glu Val Asp Ala Ala Val Thr Pro Glu Glu Arg His Leu Ser
65                  70                  75                  80

Lys Met Gln Gln Asn Gly Tyr Glu Asn Pro Thr Tyr Lys Phe Phe Glu
                85                  90                  95

Gln Met Gln Asn Asp Tyr Lys Asp Asp Asp Lys
                100                 105
```